United States Patent
McFetridge et al.

(10) Patent No.: US 10,300,091 B2
(45) Date of Patent: *May 28, 2019

(54) SUSTAINED RELEASE ANGIOGENESIS MODULATING COMPOSITIONS AND METHODS FOR INDUCTION AND MODULATION OF ANGIOGENESIS

(71) Applicant: University of Florida Research Foundation, Inc., Gainesville, FL (US)

(72) Inventors: Peter S. McFetridge, Gainesville, FL (US); Marc C. Moore, Gainesville, FL (US)

(73) Assignee: UNIVERSITY OF FLORIDA RESEARCH FOUNDATION, INC., Gainesville, FL (US)

(*) Notice: Subject to any disclaimer, the term of this patent is extended or adjusted under 35 U.S.C. 154(b) by 28 days.

This patent is subject to a terminal disclaimer.

(21) Appl. No.: 15/309,306

(22) PCT Filed: May 7, 2015

(86) PCT No.: PCT/US2015/029666
§ 371 (c)(1),
(2) Date: Nov. 7, 2016

(87) PCT Pub. No.: WO2015/171880
PCT Pub. Date: Nov. 12, 2015

(65) Prior Publication Data
US 2017/0209497 A1 Jul. 27, 2017

Related U.S. Application Data

(63) Continuation-in-part of application No. 14/243,123, filed on Apr. 2, 2014, now Pat. No. 9,821,013.

(60) Provisional application No. 61/990,256, filed on May 8, 2014, provisional application No. 61/807,401, filed on Apr. 2, 2013.

(51) Int. Cl.
| | |
|---|---|
| *A61K 35/50* | (2015.01) |
| *A61K 9/16* | (2006.01) |
| *A61L 27/36* | (2006.01) |
| *C12N 5/071* | (2010.01) |
| *A61K 38/18* | (2006.01) |
| *A61K 38/19* | (2006.01) |
| *A61L 27/38* | (2006.01) |
| *A61L 27/54* | (2006.01) |

(52) U.S. Cl.
CPC ............ *A61K 35/50* (2013.01); *A61K 9/1647* (2013.01); *A61K 9/1658* (2013.01); *A61K 38/18* (2013.01); *A61K 38/19* (2013.01); *A61L 27/3604* (2013.01); *A61L 27/3683* (2013.01); *A61L 27/3808* (2013.01); *A61L 27/54* (2013.01); *C12N 5/069* (2013.01); *C12N 5/0691* (2013.01); *A61L 2300/252* (2013.01); *A61L 2300/426* (2013.01); *A61L 2300/602* (2013.01); *C12N 2502/1347* (2013.01); *C12N 2502/28* (2013.01); *C12N 2503/04* (2013.01); *C12N 2533/92* (2013.01)

(58) Field of Classification Search
None
See application file for complete search history.

(56) References Cited

U.S. PATENT DOCUMENTS

| | | | |
|---|---|---|---|
| 4,829,000 A | 5/1989 | Kleinman et al. | |
| 4,994,559 A | 2/1991 | Moscatelli et al. | |
| 5,976,782 A | 11/1999 | Parish et al. | |
| 8,637,309 B2* | 1/2014 | Oh ........................ | C12N 5/0062 |
| | | | 435/363 |
| 2005/0002915 A1 | 1/2005 | Atala et al. | |
| 2005/0203636 A1 | 9/2005 | McFetridge | |
| 2007/0071828 A1 | 3/2007 | Tseng et al. | |
| 2007/0128171 A1 | 6/2007 | Tranquillo et al. | |
| 2008/0131522 A1 | 6/2008 | Liu et al. | |
| 2009/0263359 A1* | 10/2009 | Ferreira ............... | C12N 5/0619 |
| | | | 424/93.7 |
| 2010/0226895 A1 | 9/2010 | Boruch | |
| 2012/0129775 A1 | 5/2012 | Zudaire et al. | |
| 2013/0195992 A1 | 8/2013 | Tseng et al. | |
| 2014/0151623 A1 | 6/2014 | Jeon et al. | |
| 2014/0294780 A1 | 10/2014 | McFetridge | |

FOREIGN PATENT DOCUMENTS

EP 0218065 * 4/1987 ............... C12N 5/00

OTHER PUBLICATIONS

Chu et al, "Therapeutic angiogenesis: controlled delivery of angiogenic factors" Therapeutic Delivery, Jun. 2012; 3 (6): 693-714 (34 page author manuscript included) (Year: 2012).*
International Search Report from PCT/US2015/029666 dated Jul. 27, 2015.
Daniel et al. "Development of the Human Umbilical Vein Scaffold for Cardiovascular .Tissue Engineering Applications," ASAIO Journal, May 1, 20Q5 (May 1, 2005), vol. 51, pp. 252-261.
International Search Report from PCT/US2014/032696 dated Aug. 27, 2014.
Thiex et al. "Tissue-specific cytokine release from human extraplacental membranes stimulated by lipopolysaccharide in a two-compartment tissue culture system." Reprod Bioi Endocrinol. Oct. 26, 2009 (Oct. 26, 2009), vol. 7, No. 117, pp. 1-10.
Miyagami et al. "Physiological changes in the pattern of placental gene expression early in the first trimester," Reprod Sci. Dec. 10, 2012 (Dec. 10, 2012), vol. 20, No. 6, pp. 710-714.

(Continued)

*Primary Examiner* — Allison M Fox
(74) *Attorney, Agent, or Firm* — Thomas Horstemeyer, LLP

(57) ABSTRACT

The present disclosure provides compositions including a human placental extract and biodegradable microparticles, sustained release angiogenesis-modulating compositions, compositions and methods for releasing a placental extract to a target over a period of time, and methods for inducing and/or modulating angiogenesis and identifying modulators of angiogenesis. The present disclosure also provides methods of making a composition, including a placental extract that can induce and/or modulate angiogenesis.

29 Claims, 28 Drawing Sheets

(56) References Cited

OTHER PUBLICATIONS

Presta et al. "Human placental tissue stimulates bovine capillary endothelial cell growth, migration and protease production." Biosci Rep. Sep. 1, 1985 (Sep. 1, 1985), vol. 5, No. 9, pp. 783-790.
Auerbach, R., Lewis, R., Shinners, B., Kubai, L. & Akhtar, N. Angiogenesis assays: a critical overview. Clinical chemistry 49, 32-40 (2003).
Auerbach, R., Akhtar, N., Lewis, R.L. & Shinners, B.L. Angiogenesis assays: problems and pitfalls. Cancer metastasis reviews 19, 167-172 (2000).
Bose, B. Burn wound dressing with human amniotic membrane. Annals of the Royal College of Surgeons of England 61, 444 (1979).
Burri, P.H. & Djonov, V. Intussusceptive angiogenesis—the alternative to capillary sprouting. Molecular aspects of medicine 23, S1-27 (2002).
Daniel, J., Abe, K. & McFetridge, P.S. Development of the human umbilical vein scaffold for cardiovascular tissue engineering applications. ASAIO J 51, 252-261 (2005).
Djonov, V., Baum, O. & Burri, P.H. Vascular remodeling by intussusceptive angiogenesis. Cell and tissue research 314, 107-117 (2003).
Epstein, S.E, Fuchs, S., Zhou, Y.E, Baffour, R. & Kornowski, R. Therapeutic interventions for enhancing collateral development by administration of growth factors: basic principles, early results and potential hazards. Cardiovascular Research 49, 532-542 (2001).
Febbraio, M., Hajjar, D.P. & Silverstein, R.L. CD36: a class B scavenger receptor involved in angiogenesis, atherosclerosis, inflammation, and lipid metabolism. Journal of Clinical Investigation 108, 785-791 (2001).
Ferrara, N. & Alitalo, K. Clinical applications of angiogenic growth factors and their inhibitors. Nature medicine 5 (1999).
Fett, J.W. et al. Isolation and characterization of angiogenin, an angiogenic protein from human carcinoma cells. Biochemistry 24, 5480-5486 (1985).
Folkman, J. Angiogenesis in cancer, vascular, rheumatoid and other disease. Nature medicine 1, 27-31 (1995).
Hariawala, M.D. et al. VEGF improves myocardial blood flow but produces EDRF-mediated hypotension in porcine hearts. Journal of Surgical Research 63, 77-82 (1996).
Iozzo, R. V. & San Antonio, J.D. Heparan sulfate proteoglycans: heavy hitters in the angiogenesis arena. Journal of Clinical Investigation 108, 349-355 (2001).
Jain, R.K., Schlenger, K., Hockel, M. & Yuan, F. Quantitative angiogenesis assays: progress and problems. Nature medicine 3, 1203-1208 (1997).
Jin, C.Z. et al. Human amniotic membrane as a delivery matrix for articular cartilage repair. Tissue engineering 13, 693-702 (2007).
Kalluri, R. Basement membranes: structure, assembly and role in tumour angiogenesis. Nature reviews. Cancer 3, 422-433 (2003).
Kleinman, H.K. & Martin, G.R. Matrigel: basement membrane matrix with biological activity. Seminars in cancer biology 15, 378-386 (2005).
Kurz, H., Burri, P.H. & Djonov, V.G. Angiogenesis and vascular remodeling by intussusception: from form to function. News in physiological sciences : an international journal of physiology produced jointly by the International Union of Physiological Sciences and the American Physiological Society 18, 65-70 (2003).
Laschke, M.W. et al. Angiogenesis in tissue engineering: breathing life into constructed tissue substitutes. Tissue engineering 12, 2093-2104 (2006).
Lawler, J. Thrombospondin-1 as an endogenous inhibitor of angiogenesis and tumor growth. J Cell Mol Med 6, 1-12 (2002).
Les, S.-H. & Tseng, S. Amniotic membrane transplantation for persistent epithelial defects with ulceration. American journal of ophthalmology 123, 303-312 (1997).
Lee, R.J. et al. VEGF gene delivery to myocardium deleterious effects of unregulated expression. Circulation 102, 898-901 (2000).
Lokmic, Z. & Mitchell, G.M. Engineering the microcirculation. Tissue Eng Part B Rev 14, 87-103 (2008).
Montesano, R., Vassalli, J.-D., Baird, A., Guillemin, R. & Orci, L. Basic fibroblast growth factor induces angiogenesis in vitro. Proceedings of the National Academy of Sciences 83, 7297-7301 (1986).
O'Byrne, K.J., Dalgleish, A., Browning, M., Steward, W. & Harris, A. The relationship between angiogenesis and the immune response in carcinogenesis and the progression of malignant disease. European journal of cancer 36, 151-169 (2000).
Paslakis, G. et al. The Putative Role of Human Peritoneal Adipocytes in the Fight against Bacteria: Synthesis of the Antimicrobial Active Peptide DEFA1-3. Nephron Experimental Nephrology 115, e96-e100 (2010).
Pepper, M., Ferrara, N., Orci, L. & Montesano, R. Potent synergism between vascular endothelial growth factor and basic fibroblast growth factor in the induction of angiogenesis in vitro. Biochemical and biophysical research communications 189, 824-831 (1992).
Perretti, M. et al. Endogenous lipid-and peptide-derived anti-inflammatory pathways generated with glucocorticoid and aspirin treatment activate the lipoxin A4 receptor. Nature medicine 8, 1296-1302 (2002).
Risau, W. Mechanisms of angiogenesis. Nature 386, 671-674 (1997).
Rundhaug, J.E. Matrix metalloproteinases and angiogenesis. J Cell Mol Med 9, 267-285 (2005).
Kim, S. Bell, K. Mousa, S.A. & Varner, J.A. Regulation of Angiogenesis<i> in Vivo</i> by Ligation of Integrin $\alpha 5\beta 1$ with the Central Cell-Binding Domain of Fibronectin. The American journal of pathology 156, 1345-1362 (2000).
Sullivan, D.C. & Bicknell, R. New molecular pathways in angiogenesis. British journal of cancer 89, 228-231 (2003).
Thurston, G., Murphy, T.J., Baluk, P., Lindsey, J.R. & McDonald, D.M. Angiogenesis in mice with chronic airway inflammation: strain-dependent differences. Am J Pathol 153, 1099-1112 (1998).
Vailhe, B. Vittet, D. & Feige, J.J. In vitro models of vasculogenesis and angiogenesis. Laboratory investigation; a journal of technical methods and pathology 81, 439-452 (2001).
Warren, M.S. et al. Comparative gene expression profiles of ABC transporters in brain microvessel endothelial cells and brain in five species including human. Pharmacological Research 59, 404-413 (2009).
Zisch, A.H., Lutolf, M.P. & Hubbell, J.A. Biopolymeric delivery matrices for angiogenic growth factors. Cardiovascular Pathology 12, 295-310 (2003).
Patarroyo, M., Tryggvason, K. & Virtanen, I. in Seminars in cancer biology, vol. 12 197-207 (Elsevier, 2002).
Xu et al. Proteolytic exposure of a cryptic site within collagen type IV is required for angiogenesis and tumor growth in vivo. The Journal of cell biology 154, 1069-1080 (2001).
Adair, T. In Integrated systems physiology, from molecule to function to disease (Morgan & Claypool, 2011).
Wang, Y. & Zhao, S. In Vascular Biology of the Placenta (San Rafael (CA); 2010).
Cristofanilli, M., Charnsangavej, C. & Hortobagyi, G.N. Angiogenesis modulation in cancer research: novel clinical approaches. Nature reviews. Drug discovery 1, 415-426 (2002).
Gao et al "Mechanisms of action of angiogenin" Acta Biochim Biophys Sin (2008) vol. 40, Issue 7, pp. 619-624.
Drake, C. J., et al., Vascular Morphogenesis: In Vivo, In Vitro, In Mente—The Morphogenesis of Primordial Vascular Networks 3-19 (Birkhäuser, 1996).
Ye, M., et al., "Issues in long-term protein delivery using biodegradable microparticles". J. Control. Release 146, 241-260 (2010).
Kirchner, L., et al., "Quantitation of Angiogenesis in the Chick Chorioallantoic Membrane Model Using Fractal Analysis," Microvascular Research 51, 2-14 (1996).
Moore, M.C., et al., "Novel human-derived extracellular matrix induces in vitro and in vivo vascularization and inhibits fibrosis". Biomaterials 49 (2015) 37-46.
Cockerill, G.W., et al., "Angiogenesis: models and modulators". International review of cytology 159, 113-160 (1995).
Stein, I., et al., "Stabilization of vascular endothelial growth factor mRNA by hypoxia and hypoglycemia and coregulation with other ischemia-induced genes". Molecular and Cellular Biology 15(10), 5363-5368 (1995).

(56) References Cited

OTHER PUBLICATIONS

Pardali, E., et al., "Signaling by members of the TGF-β family in vascular morphogenesis and disease". Trends in Cell Biology 20, 556-567 (2010).
Largo, R. A., et al., "Angiogenesis and Vascularity for Tissue Engineering Applications". Regenerative Medicine and Tissue Engineering—Cells and Biomaterials, 433-448(2010).
Carmeliet, P., "Angiogenesis in health and disease". Nature medicine 9, 6, 653-660 (2003).
Achen, M.G., et al., "The vascular endothelial growth factor family; proteins which guide the development of the vasculature". International Journal of Experimental Pathology 79, 255-265 (1998).
Carmeliet, P., "Mechanisms of angiogenesis and arteriogenesis". Nature medicine 6(3), 389-395 (2000).
Formiga, F. R., et al., "Angiogenic therapy for cardiac repair based on protein delivery systems". Heart failure reviews 17, 449-473 (2012).
Iruela-Arispe, M., et al., "Angiogenesis: a Dynamic Balance of Stimulators and Inhibitors". Thrombosis and Haemostasis 78(1), 672-677 (1997).
Vasir, J. K., et al., "Bioadhesive microspheres as a controlled drug delivery system". International Journal of Pharmaceutics 255,13-32 (2003).
Sather, S., et al., "Sustanined release theophylline tablets by direct compression Part 1: formulation and in vitro testing". International Journal of Pharmaceutics 164, 1-10 (1998).
Determan, A. S., et al., "Encapsulation, stabilization, and release of BSA-FITC from polyanhydride microspheres". Journal of controlled release 100, 97-109 (2004).
Narayani, R., et al., "Gelatin microsphere cocktails of different sizes for controlled release of anticancer drugs". International journal of pharmaceutics 143, 255-258 (1996).
Tamizharasi, S., et al., "Formulation and Evaluation of Pentoxifylline-Loaded Poly ( – caprolactone) microspheres". Indian J Pharm Sci 70(3), 333-337: 1-12 (2008).
Staton, C. A., et al., "A critical analysis of current in vitro and in vivo angiogenesis assays". International journal of experimental pathology 90, 195-221 (2009).
Liu, L.X., et al., "Stabilization of Vascular Endothelial Growth Factor mRNA by Hypoxia-Inducible Factor 1". Biochemical and Biophysical Research Communications 291, 908-914 (2002).
Chaturvedi, G., "A Review on Microspheres technology and its application". Birla Institute of Technology and Science (2009), 11 pages.
Acharya, G., et al., "A study of drug release from homogeneous PLGA microstructures". Journal of Controlled Release 146, 201-206 (2010).
Rowley, J. A., et al., "Alginate hydrogels as synthetic extracellular matrix materials". Biomaterials 20, 45-53 (1999).
Román, B. S., et al. "Co-encapsulation of an antigen and CpG oligonucleotides into PLGA microparticles by TROMS technology". European Journal of Pharmaceutics and Biopharmaceutics 70, 98-108 (2008).
Acharya, A. P., et al., "Combinatorial co-encapsulation of hydrophobic molecules in poly(lactide-co-glycolide) microparticles". Biomaterials 34, 3422-3430 (2013).
Jay, S. M., et al., "Engineering of multifunctional gels integrating highly efficient growth factor delivery with endothelial cell transplantation". The FASEB Journal 22(8), 2949-2956 (2008).
Cohen, S., et al., "Controlled Delivery Systems for Proteins Based on Poly(Lactic/Glycolic Acid) Microspheres". Pharmaceutical Research 8, 6, 713-720 (1991).
Wang, Y., et al., "Degradable PLGA scaffolds with basic fibroblast growth factor: experimental studies in myocardial revascularization". PLGA Scaffolds with bFGF for Revascularization—Tex Heart Inst J 36(2), 89-97, (2009).
Ravi, S., et al., "Development and characterization of polymeric microspheres for controlled release protein loaded drug delivery system". Indian J Pharm Sci. 70(3), 303-309 (2008).
Shi, H., et al., "Enhanced angiogenesis in porous collagen-chitosan scaffolds loaded with angiogenin". Tissue Eng Part A, 14, 1775-1785 (2008).
Lee, W., L. et al., "Fabrication and drug release study of double-layered microparticles of various sizes". Journal Pharmaceutical Sci 101, 8, 2787-2797 (2012).
CShan, O. C. M., et al., "Fabrication of nano-fibrous collagen microspheres for protein delivery and effects of photochemical crosslinking on release kinetics". Journal of Controlled Release 129, 135-143 (2008).
Giteau, A., et al., "How to achieve sustained and complete protein release from PLGA-based microparticles?", International Journal of Pharmaceutics 350, 14-26 (2008).
Hughes, C. S., et al., "Matrigel: a complex protein mixture required for optimal growth of cell culture". Proteomics 10, 1886-1890 (2010).
Goodwin A. M., et al., "In vitro assays of angiogenesis for assessment of angiogenic and anti-angiogenic agents". Microvascular Research 74(2-3), 172-183 (2007).
Xie, J., et al. "Induction of angiogenesis by controlled delivery of vascular endothelial growth factor using nanoparticles". Cardiovasc Ther 31, e12-e18 (2013).
Lassalle, V., et al., "PLA nano- and microparticles for drug delivery: an overview of the methods of preparation". Macromolecular Bioscience—Macromolecular Journals 7, 767-783 (2007).
Lee, W. L, et al., "Modeling of drug release from biodegradable triple-layered microparticles". J Biomed Mater Res A 100, 3353-3362 (2012).
Carmeliet, P., et al., "Molecular mechanisms and clinical applications of angiogenesis". Nature 473, 298-307, (2011).
Chung, J., et al., "Neovascularization in Tissue Engineering". Cells 1, 1246-1260 (2012).
Pan, S. C., et al., "Angiogenin expression in burn blister fluid: implications for its role in burn wound neovascularization". Wound Repair and Regeneration 20, 731-739 (2012).
Simón-Yarza, T., et al., "PEGylated-PLGA microparticles containing VEGF for long term drug delivery". International Journal of Pharmaceutics 440, 13-18 (2013).
Chan, B.P., et al., "Photochemical cross-linking for collagen-based scaffolds: a study on optical properties, mechanical properties, stability, and hematocompatibility". Tissue Engineering 13, 1, 73-85 (2007).
Klose, D., et al., "PLGA-based drug delivery systems: Importance of the type of drug and device geometry". International Journal of Pharmaceutics 354, 95-103 (2008).
Kirby, G., et al., "PLGA-Based Microparticles for the Sustained Release of BMP-2". Polymers 3(1):571-586, (2011).
Bouyer, E., et al., "Proteins, polysaccharides, and their complexes used as stabilizers for emulsions: alternatives to synthetic surfactants in the pharmaceutical field?". Int J Pharm 436, 359-378 (2012).
Igartua, M., et al., "Stability of BSA encapsulated into PLGA microspheres using PAGE and capillary electrophoresis". International Journal of Pharmaceutics 169, 45-54 (1998).
Chu, H., et al., "Therapeutic angiogenesis: controlled delivery of angiogenic factors". Ther Deliv. 03(6): 693-714, 2012.
European Search Report, dated Jan. 26, 2018, Application 15810294.7, The Hague, 10 pages.
Suri, M., et al., "Bio-Inspired Stochastic Computing Using Binary CBRAM Synapses". IEEE Transactions on Electron Devices, vol. 60, No. 7, 2402-2409, 2013.
Gandhi, J. K., et al. "Alginate-based strategies for therapeutic vascularization". Therapeutic Delivery 4(3), 327-341 (2013).
Jay, S. M., et al., "Controlled delivery of VEGF via modulation of alginate microparticle ionic crosslinking". Journal of Controlled Release 134, 26-34 (2009).
http://www.donatelifeny.org/about-donation/data/. 10 pages.
Kim, B.S., et al., "Development of biocompatible synthetic extracellular matrices for tissue engineering". TIBTECH 16, 224-230 (1998).
Bach, F. H., "Xenotransplantation: problems and prospects". Annu. Rev. Med. 49, 301-310 (1998).
Dvir, T., et al., "Nanotechnological strategies for engilex tissues". Nat. Nanotechnology 6, 13-22 (2011).

(56) References Cited

OTHER PUBLICATIONS

Langer, R., et al. "Tissue Engineering". Science 260, 920-926 (1993).
Martin, Y., et al., "Bioreactors for tissue mass culture: Design, characterization, and recent advances". Biomaterials 26, 7481-7503 (2005).
Muschler, G. F., et al., "Engineering Principles of Clinical Cell-Based Tissue Engineering". The Journal of Bone & Joint Surgery JB & JS 1541-1558 (2004).
Soker, S., et al., "Systems for therapeutic angiogenesis in tissue engineering". World J. Urol. 18, 10-8 (2000).
Adair, T. H., et al., Angiogenesis—Colloquium Series in Integrated Systems Physiology: from Molecule to Function, http://books.google.com/books?id=ykn66NeaPakC, https://www.ncbi.nlm.nih.gov/books/NBK53242, Morgan & Claypool Life Sciences, 75 pages (2010).
Vernon, R. B., et al., "A Novel , Quantitative Model for Study of Endothelial Cell Migration and Sprout Formation within Three-Dimensional Collagen Matrices". Microvascular Research 57, 118-133 (1999).
Montesano, R., et al., Vascular Morphogenesis: In Vivo, In Vitro, In Mente—Three-Dimensional In Vitro Assay of Endothelial Cell Invasion and Capillary Tube Morphogenesis 79-110 (Birkhäuser, 1996).
Lee, K., et al., "Growth factor delivery-based tissue engineering: general approaches and a review of recent developments". Journal of the Royal Society Interface 8, 153-170 (2011).
Moore, M. C. "Modulation of nutrient deficiencies occurring in engineered ex vivo tissue scaffolds".J. Crayton Pruitt Family Department of Biomedical Engineering. 1 page, (2013).
Jaffe, E. A., et al., "Culture of Human Endothelial Cells Derived from Umbilical Veins. Identification by Morphologic and Immunologic Criteria". J Clin Invest. 52(11), 2745-2756 (1973).
Tabata, Y., et al., "Neovascularization effect of biodegradable gelatin microspheres incorporating basic fibroblast growth factor". Journal of Biomaterials Science, 10(1), 79-94 (1999).
Guidolin, D., "A new image analysis method based on topological and fractal parameters to evaluate the angiostatic activity of docetaxel by using the Matrigel assay in vitro". Microvascular Research 67, 117-24 (2004).
Brey, E. M., et al., "A technique for quantitative three-dimensional analysis of microvascular structure". Microvascular Research 63, 279-94 (2002).
Vico, P. G., et al. "Dynamic study of the extraembryonic vascular network of the chick embryo by fractal analysis". J. Theor. Biol. 195, 525-532 (1998).

\* cited by examiner

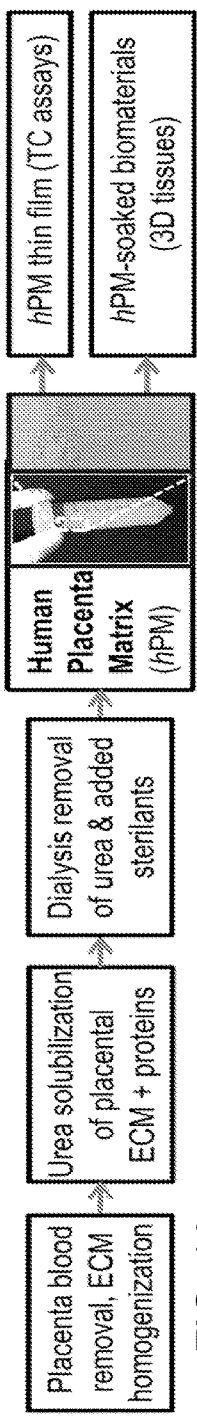
FIG. 1A
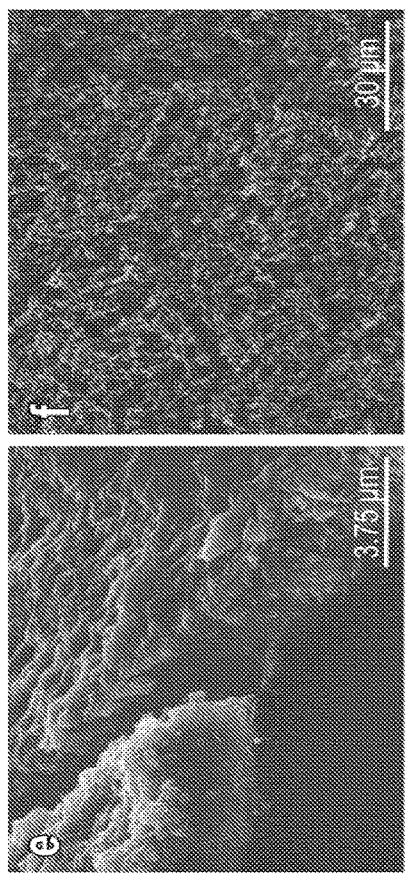
FIG. 1B
FIG. 1C
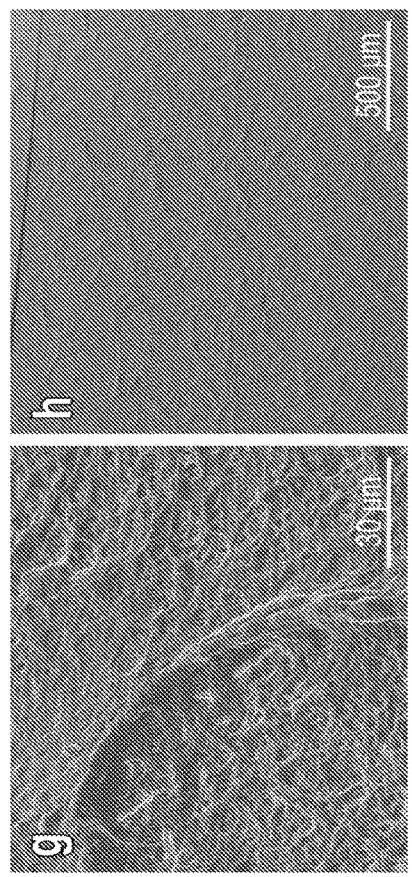
FIG. 1D
FIG. 1E

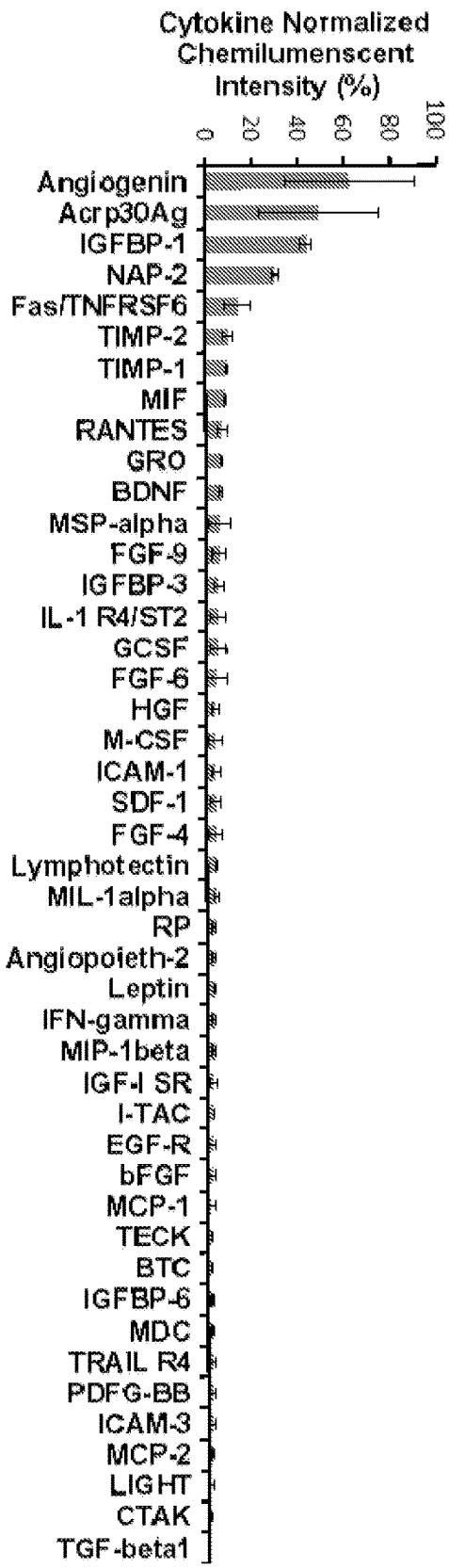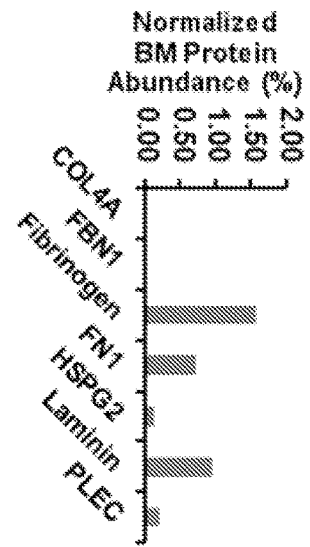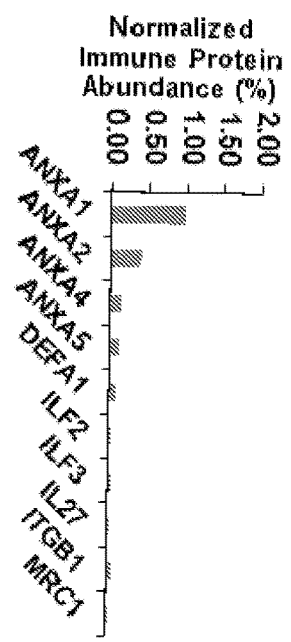
FIG. 2A
FIG. 2B
FIG. 2C

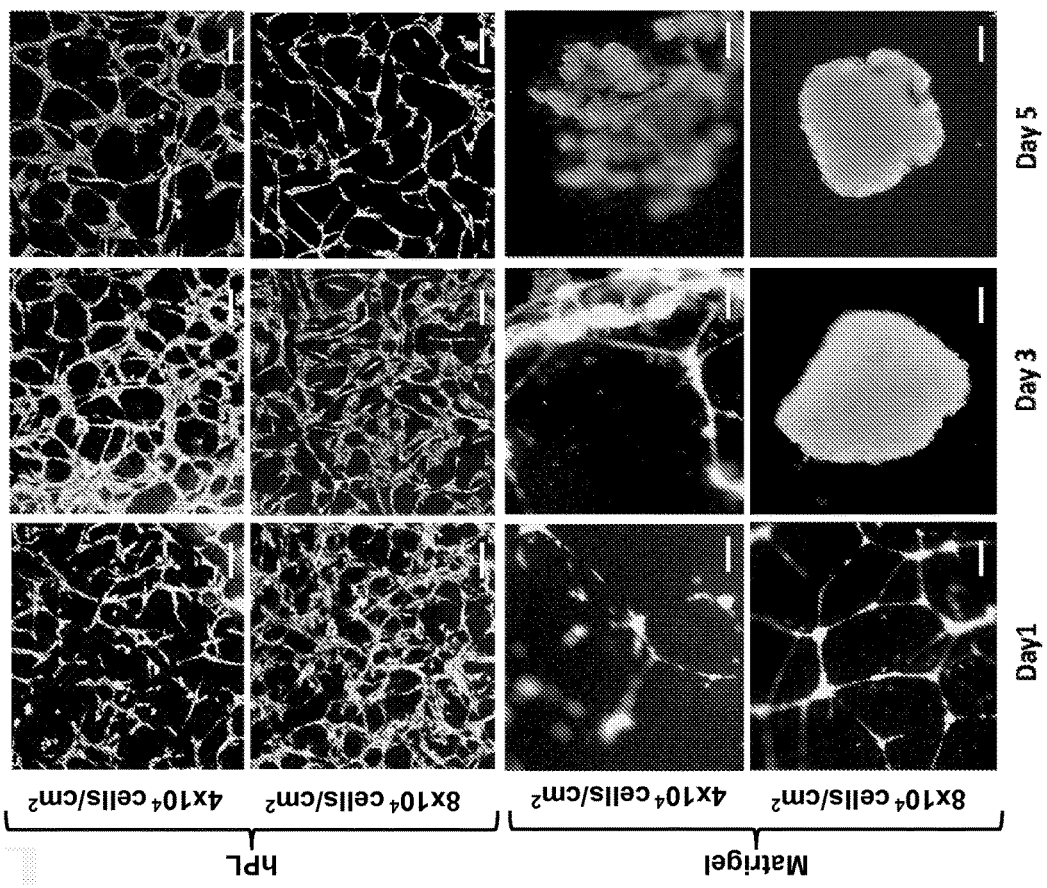

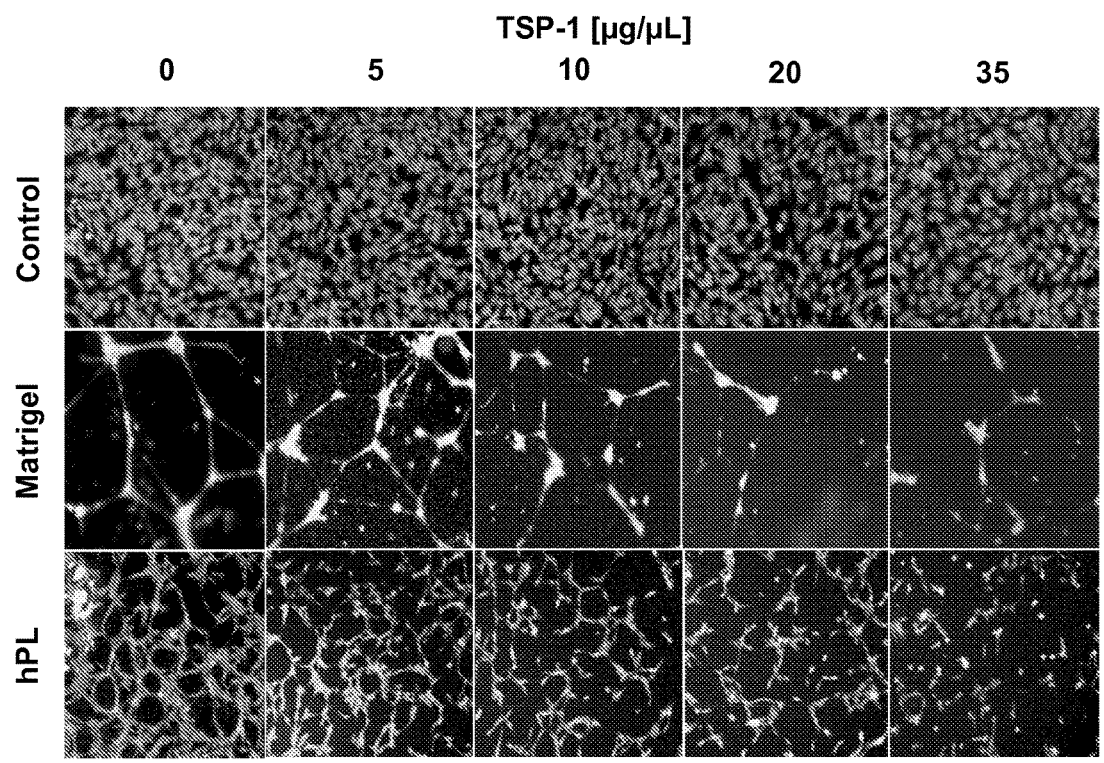
FIG. 4A
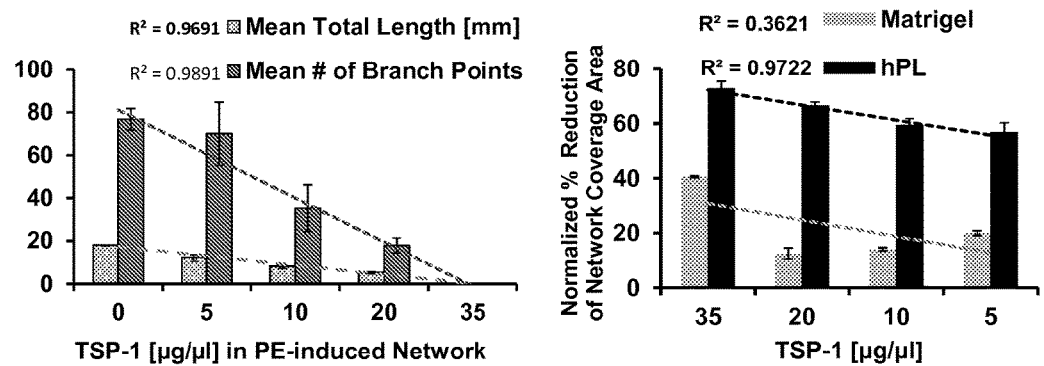
FIG. 4B
FIG. 4C

FIG. 7A
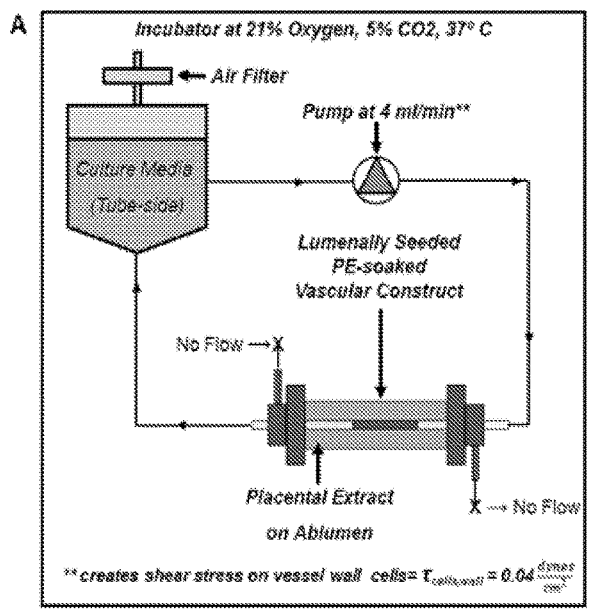
FIG. 7B
FIG. 7C
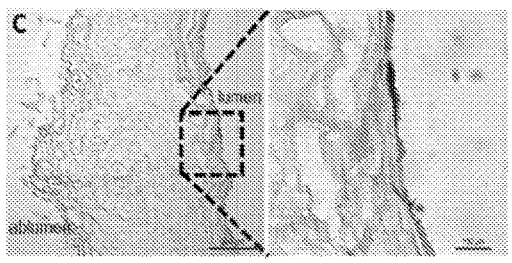
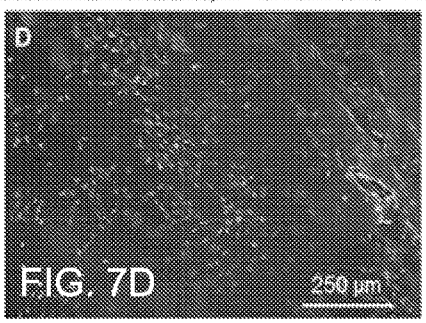
FIG. 7D
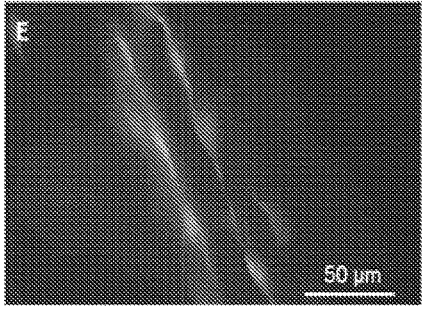
FIG. 7E

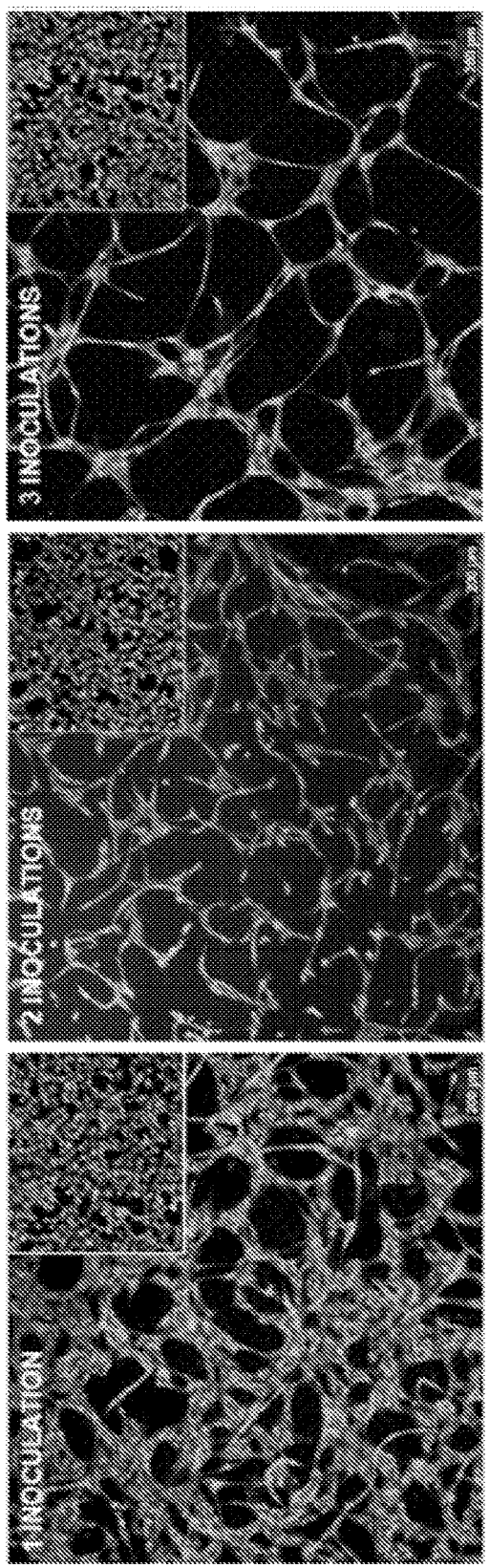
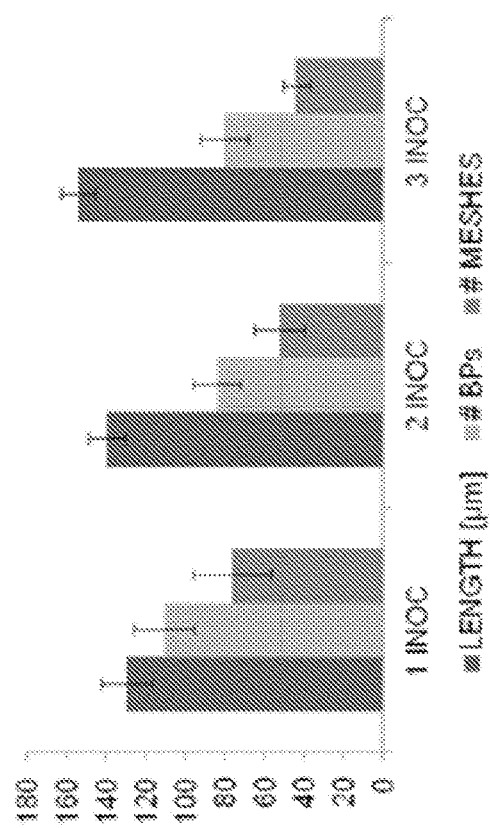
FIG. 10A
FIG. 10B

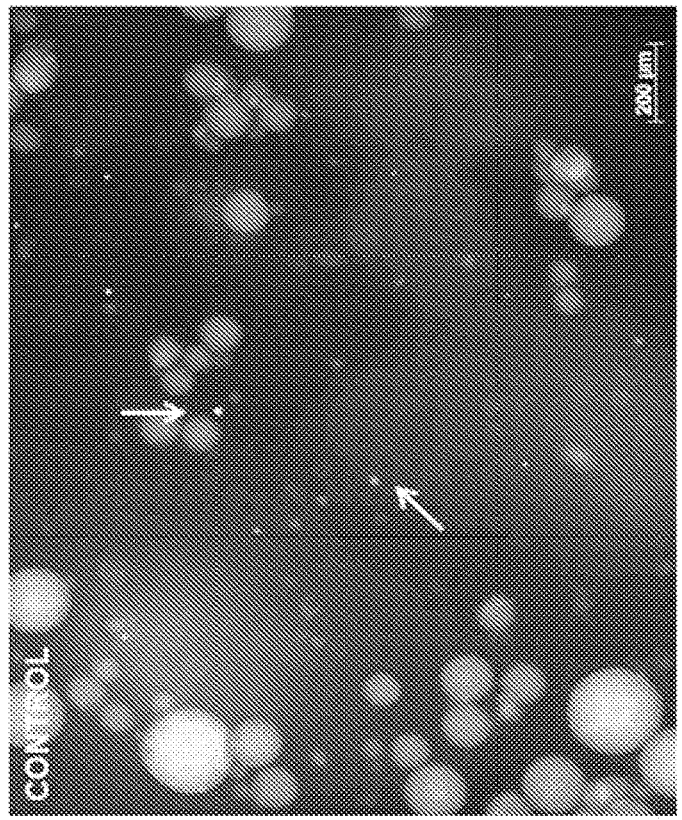
FIG. 15

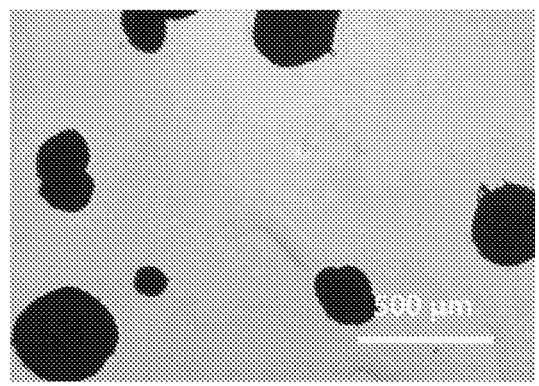
Single homogenization (2 min)
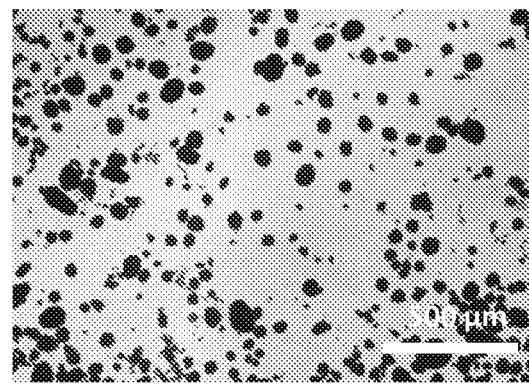
Dual homogenization (2 min / 1 min)
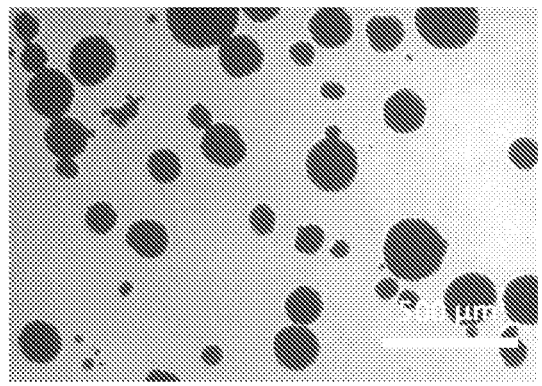
Dual homogenization (2 min / 20 sec)
FIG. 17A
FIG. 17B
FIG. 17C

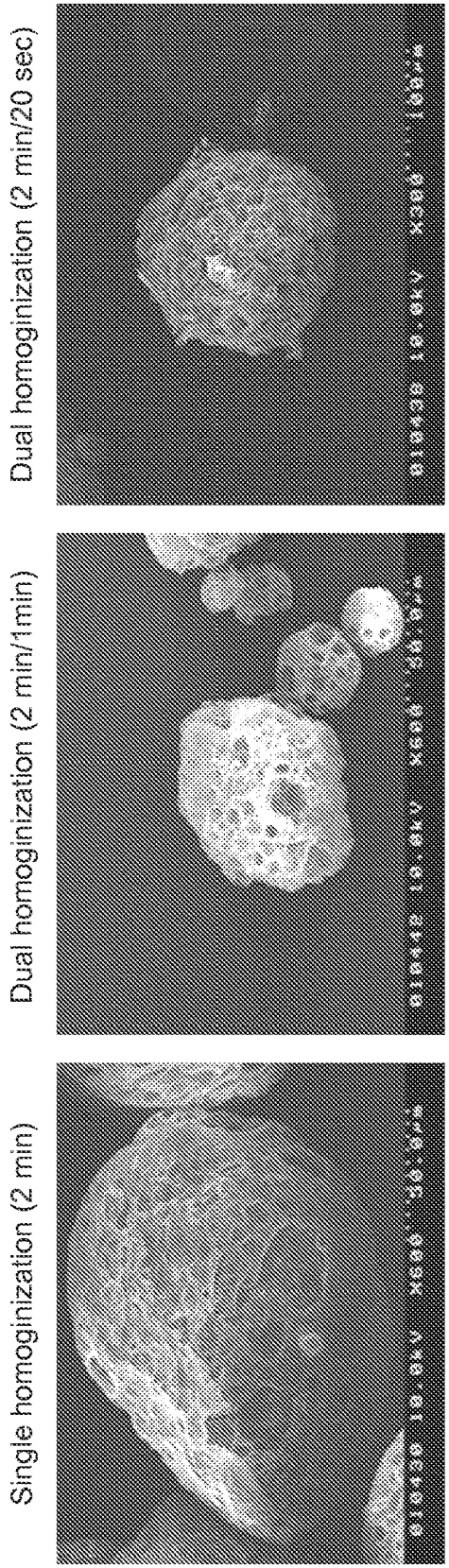
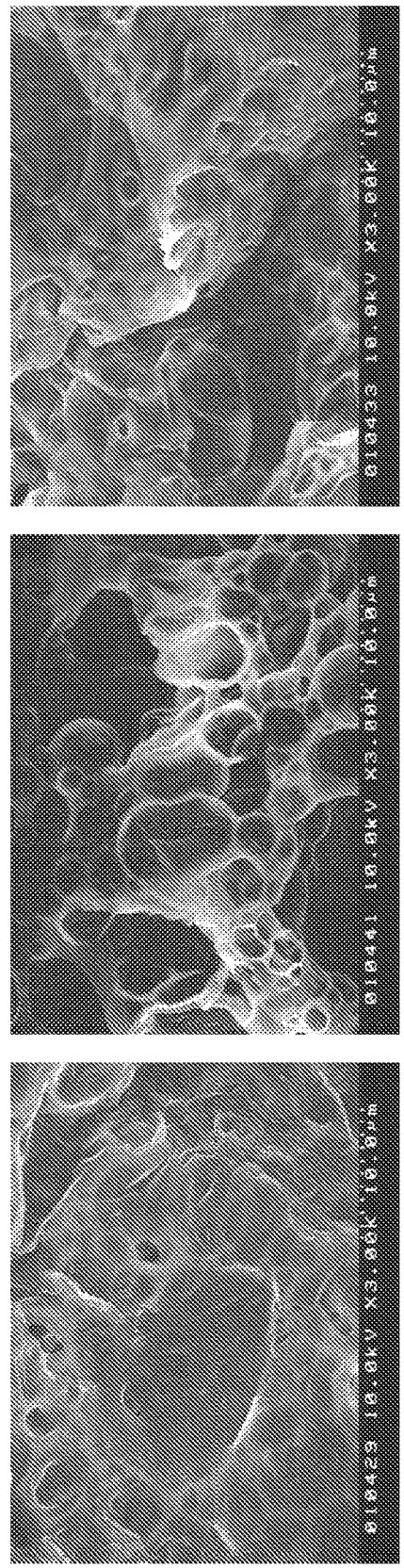
FIG. 18A  FIG. 18B  FIG. 18C
FIG. 18D  FIG. 18E  FIG. 18F

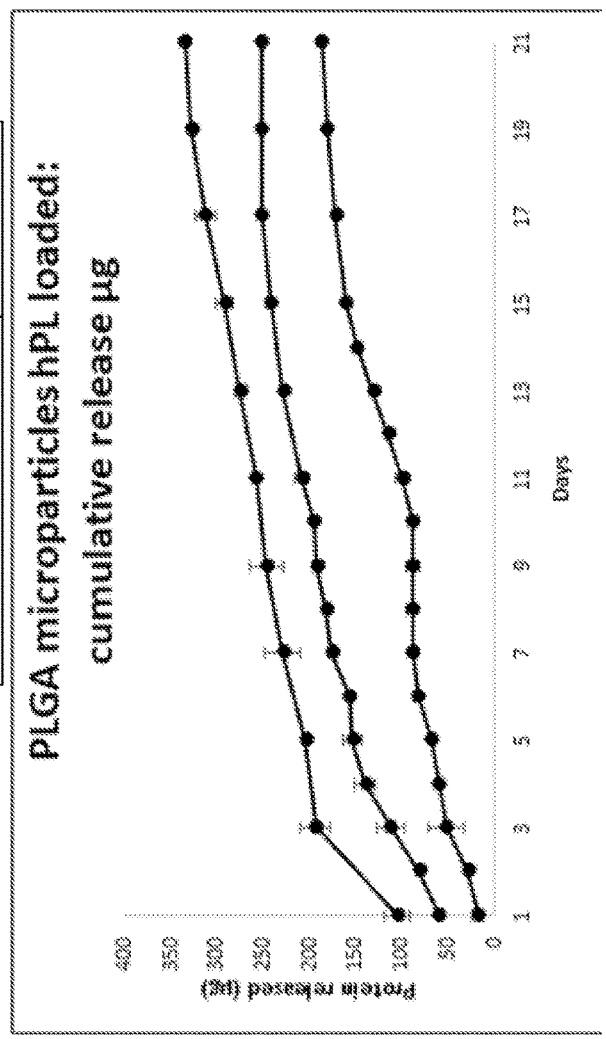

SUSTAINED RELEASE ANGIOGENESIS MODULATING COMPOSITIONS AND METHODS FOR INDUCTION AND MODULATION OF ANGIOGENESIS

CROSS-REFERENCE TO RELATED APPLICATIONS

This application is the 35 U.S.C. § 371 national stage application of PCT Application No. PCT/US2015/029666, filed May 7, 2015, where the PCT claims priority to U.S. provisional application titled "Compositions and Methods for Induction and Modulation of Angiogenesis and Methods and Assays for Identifying Angiogenesis Modulators," having Ser. No. 61/990,256, filed on May 8, 2014, and a continuation-in-part of U.S. application titled "Compositions and Methods for Induction and Modulation of Angiogenesis and Methods and Assays for Identifying Angiogenesis Modulators," having Ser. No. 14/243,123, filed on Apr. 2, 2014 and issued on Nov. 21, 2017 as U.S. Pat. No. 9,821,013, which claims priority to U.S. provisional application titled "Compositions and Methods for Induction and Modulation of Angiogenesis and Methods and Assays for Identifying Angiogenesis Modulators," having Ser. No. 61/807,401, filed on Apr. 2, 2013, all of which are entirely incorporated herein by reference.

STATEMENT REGARDING FEDERALLY SPONSORED RESEARCH OR DEVELOPMENT

This invention was made with Government support under grant number HL088207 awarded by the National Institutes Health. The Government has certain rights in this invention.

BACKGROUND

Angiogenesis enables the formation of blood vessels in physiological and pathological states ranging from wound healing to cancer. Angiogenesis modulation is both location and stimuli dependent, and each instance may involve a unique combination of regulatory molecules.

The inability to vascularize engineered organs and to revascularize areas of infarction has been a major roadblock to delivering successful regenerative medicine therapies to the clinic. The ability to modulate angiogenesis in a determinant fashion would have a significant impact in a wide range of clinical applications from defining normal and pathological vascular physiology, regeneration of tissues/organs, wound healing, infarct tissue repair and the inhibition of cancer. A variety of different approaches have been taken to initiate angiogenesis and drive larger vessel formation, including direct cell seeding (mono and co-cultures), use of stem cells, and combinations of human-derived modulators/growth factors. To date there has been little success translating these in vitro approaches, which typically use non-human animal compounds, to the clinic due to their discrete protein makeup, non-human derivation, tumor-derivation, or lack of genetic regulation in the case of methods to control gene expression.

Current methods to induce in vitro angiogenesis are made of simple combinations of human-derived modulators, use animal-derived stimulators, or are entirely dependent on the use of live animals for evaluation. Using these current in vitro models made of simple combinations of human-derived and/or animal derived modulators to test potential angiogenesis inhibiting drugs constrains the screening process because they fail to represent the broad set of human in vivo molecular interactions. Regulation of only selected molecular pathways also confines attempts to prevascularize engineered organs since modulating angiogenesis requires induction of many metabolic pathways. Also, currently, the most popular and successful approach employs Matrigel™, a material derived from Engelbreth-Holm-Swarm mouse sarcoma cells, which is considered inappropriate for human therapies. Thus, an improved human-based method to induce and modulate angiogenesis could spur both pharmaceutical development and regenerative medicine.

SUMMARY

Briefly described, embodiments of the present disclosure provide human placental extract compositions comprising the human placental extract, sustained-release angiogenesis-modulating compositions, methods of inducing angiogenesis, and anti-inflammatory compositions and methods.

The present disclosure provides a composition including a human placental extract coupled to biodegradable microparticles, such that the human placental extract is released from the microparticles after exposure to cells in vivo or in vitro. The human placental extract is obtained from a human placental sample where blood and solids have been substantially removed from the extract and the extract includes placental proteins including cytokines and growth factors that were present in the placental sample.

Embodiments of methods for inducing angiogenesis of the present disclosure include contacting cells with a sustained release angiogenesis-modulating composition, where the sustained release angiogenesis-modulating composition includes biodegradable microparticles coupled to the human placental extract of the present disclosure such that the human placental extract is released from the microparticles over a period of time after exposure of the microparticles to cells in vitro or in vivo. In embodiments, the method further includes coupling the sustained release angiogenesis-modulating composition to a biomaterial to induce vascularization of the biomaterial.

The present disclosure also provides methods of reducing inflammation in a subject by administering the human placental extract of the present disclosure or the sustained release/human placental extract composition of the present disclosure to a subject in need of treatment for inflammation.

Other methods, compositions, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1A-1K illustrate the formation of a human placental extract (hPE) (also referred to herein as a human placenta matrix or hPM), characterization of hPE thin films, and characterization of angiogenic networks formed on hPE thin films. FIG. 1A illustrates an embodiment of steps for obtaining hPM by homogenization of placental ECM followed by urea solubilization and dialysis. FIGS. 1B-1C are SEM images showing the surface morphology of the hPE, and FIGS. 1D-1E are SEM images of vasculogenic network formation when HUVECS were seeded at $4 \times 10^4$ cells/cm$^2$ onto hPm thin films and cultured for 3 days. FIG. 1F illustrates Rhodamine Phalloidin ("red"—shown as grey branching pathways) and DAPI ("blue"—shown as lighter gray spots within branching pathways) showing branched cell filopodia during angiogenic sprouting after 1 day on placenta extract. FIG. 1G illustrates Rhodamine Phalloidin ("red"—shown as grey branching pathways) and DAPI ("blue"—shown as lighter gray spots within branching pathways) showing a maturing angiogenic network with extensive cell cording after 3 days. FIG. 1H shows Calcein ("green"—shown as grey branches) and DAPI ("blue"—shown as lighter grey spots within branches) stained HUVECs during the initial stages cell cording and angiogenic network formation after 1 day on placenta extract. FIG. 1I illustrates DAPI ("blue"—shown as grey dashed pathway) staining showing cell cording of HUVECS after 3 days on placenta extract. FIG. 1J illustrates HUVECs seeded onto a tissue culture plate at $4 \times 10^4$ cells/cm$^2$ and cultured in endothelial cell medium for 3 days. FIG. 1K illustrates formation of angiogenic networks by HUVECs seeded at $4 \times 10^4$ cells/cm$^2$ onto placenta extract that was adhered to the surface of a tissue culture plate at 100 μL PE/cm$^2$ and then cultured in endothelial cell medium for 3 days.

FIGS. 2A-2C illustrate biochemical analysis of hPE and genetic analysis of HUVECs seeded on hPE. FIG. 2A is a bar graph illustrating cytokines analysis as performed using a sandwich-based human angiogenesis antibody array; data was normalized on a scale ranging from negative control values (0%) to positive control values (100%) (data are representative of three biological replicates). FIGS. 2B and 2C are a bar graphs illustrating the normalized spectral abundance factor (%) of immune related (2B) and angiogenesis related (2C) BM related proteins as determined using LC-MS/MS. Fibrinogen normalized spectral abundance factor value is given as the sum of FGA and FGG values, and Laminin is given as the sum of LAMA2, LAMA4, LAMA5, LAMB1, LAMB2, LAMB3, and LAMC1 values.

FIGS. 3A-3D illustrate in vitro angiogenic networks formed on hPE and Matrigel coated tissue culture flasks. FIG. 3A illustrates calcein stained HUVECS on hPE and Matrigel at variable cell seeding densities after 1 d, 3 d, and 5 d. The rate of angiogenic network maturation, defined as the time until maximum number of tubules/mm$^2$, was modulated in hPE samples by varying cell seeding densities. Quantitative analysis revealed that at 40,000 cells/cm$^2$ angiogenic networks took until day 3 to reach their maximum tubule density (tubules/mm$^2$), but at 80,000 cells/cm$^2$ networks reach their maximum tubule density in 1 day (data not shown). In Matrigel samples, angiogenic networks were not well defined after day 1. Scale bars, 200 microns. FIG. 3B illustrates that WPMY-1 myofibroblasts did not have angiogenic formations when seeded on placenta extract (FIG. 3B.i) but did when seeded on Matrigel (FIG. 3B.ii). FIG. 3C illustrates quantitative image analysis (masking) to determine angiogenic network parameters including mean tubule length (mm), tubule density, number of branch points, number of meshes, and tubule width. FIG. 3C is a series of bar graphs showing a comparison of hPE and Matrigel® induced vasculogenic network parameters, showing that by day 1, in samples seeded at 80,000 cells/cm2, Matrigel samples had reached their maximum mean tubule length, tubule density, branch points, and number of meshes, with apoptotic ball formation by day 3, while the hPM network parameters were more stable over 5 days of culture.

FIGS. 4A-4C illustrate screening of anti-antiangiogenic tumor suppressive protein Thrombospondin-1 using hPE-based angiogenesis screening assay. FIG. 4A illustrates HUVECS seeded onto hPE, Matrigel, and control culture flasks (not coated) for 1 day with TSP-1 added to the culture media were then stained using Calcein AM. Scale Bars a, 200 μm. The graph of FIG. 4B shows, in hPE-coated flasks, mean total tubule length [mm] and mean number of branch points both decreased linearly with increasing TSP-1 concentrations. The graph of FIG. 4C illustrates a comparison of normalized percent reduction of angiogenic network coverage area; hPE-coated culture plates had significantly higher sensitivity to TSP-1 concentration than Matrigel-coated culture plates, with R$^2$ values being 0.97 and 0.36, respectively.

FIG. 5A is a schematic drawing illustrating placental derived cells, scaffolds, and cytokines, to induce angiogenesis in vitro in a hPE-soaked (human umbilical vein) bioscaffold after seeding and culturing for 3 days. FIG. 5B illustrates HUVEC seeded tissue scaffolds without hPE soaking did not form angiogenic networks. FIG. 5C shows a series of representative images of hPE-soaked bioscaffolds illustrating occurrences of both sprouting and intussusceptive mechanisms of angiogenesis after 3 days of culture. At a HUVEC cell seeding density of 20,000 cells/cm$^2$ sprouting angiogenesis was most prevalent (FIGS. 5C.i.-5C.ii.). At a seeding density of 40,000 cells/cm$^2$, occurrences of both sprouting and intussusceptive angiogenesis were observed (FIGS. 5C.iii.-5C.iv.), whereas at a density of 60,000 cells/cm$^2$ (FIGS. 5C.v.-5C.vi.) angiogenic tubules formed via intussusception.

FIG. 6A is a schematic drawing illustrating decellularized HUV scaffolds incubated in PE, Matrigel, or phosphate buffered saline (control) for 2 hr prior to implantation into a rat model between the fascia and muscle layers. FIG. 6B shows a series of images illustrating scaffolds removed for analysis after 5 d implantation. Significantly more fibrotic capsule formation occurred in control and Matrigel-incubated bioscaffolds in comparison to hPE incubated scaffolds (FIGS. 6B.i.-6B.iii.). Brightfield images taken through the frontal plane of the semi-translucent bioscaffold sheets show that in comparison to controls, Matrigel and hPE-incubated scaffolds (FIGS. 6B.iv.-6B.vi.) had significantly improved capillary network formation, with the most mature capillary beds in hPE scaffolds, showing formation of vascular structures with connected arteriole to capillary to venule blood flow (FIG. 6B.vi. (circled in dashed line)). Hematoxylin and Eosin staining revealed that hPE-incubated scaffolds (FIGS. 6B.vii.-6B.vi.) had the most scaffold remodeling in comparison to control and Matrigel scaffolds. Control scaffolds (FIG. 6B.vi.) had little remodeling of their original fiber orientation and also the least cell migration into the scaffold from the ablumenal surface of the HUV bioscaffold (indicated by italicized 7). Matrigel-incubated scaffold had slightly less cell migration from the ablumen surface of the HUV in comparison to hPE-scaffolds (FIGS. 6B.vii.-6B.ix.); when compared to controls, Matrigel-incubated scaffolds also had less uniform cell distribution and less scaffold remodeling than hPE-incubated scaffolds, which had new collagen fiber orientation and a more uniform cell distribution.

FIGS. 7A-7E illustrate an embodiment for formation of angiogenic networks on human umbilical vein scaffolds (HUV) cultured using dynamic cell-culture conditions. As illustrated by the schematic drawings in FIGS. 7A and 7B, tubular HUV scaffolds were incubated in placenta extract for 2 hours before cell-seeding, and constructs were cultured for 5 days in a dual-perfusion bioreactor under standard cell culture conditions. Cells remained on the lumen of the scaffold and did not migrate (FIG. 7C). Cell-cording, an initial stage of tubule formation, was sporadic (FIGS. 7D and 7E).

FIGS. 10A-9B illustrate the cell morphologies of a microvessel network formed by HUVECs seeded onto PE and cultured for 5 days compared with HUVECs seeded onto a tissue culture plate (control). Controls are shown in the inset images in the top right corners of the images in FIG. 10A; from top left: only one inoculation of PE on day 1, two inoculations on day 1 and 3 and three inoculations on day 1, 3 and 4. It is possible to notice that increasing the number of inoculations (from 1 to 3), the capillary network evolved to a more mature and long lasting configuration. Tubule length, number of BPs and of meshes between day 1 and day 5 are compared in the histogram in FIG. 10B. A statistical difference (indicated with asterisks) in all three parameters has been found between cells which received 1 inoculation (1 INOC) and cells which received 3 (3 INOC). The statistical analysis has been performed with a double tailed t-test with unequal variance at p<0.05.

In FIG. 12A, the top row shows SEM images of a blank particle with a size of 40 μm approximately. It has a regular shape and a smooth surface. The bottom row of FIG. 12A shows SEM images of a PE-loaded particle. The change in the surface morphology and the increase in size are likely due to PE sorption. The graph in FIG. 12B shows the size distribution analysis of gelatin microparticles by light microscopy.

FIG. 14A illustrates the in vitro cumulative percent release from blank (NO PE) and loaded (PE) microparticles as a function of their dry and loaded weight respectively. Total percent cumulative release was 4.65%±0.11 and 4.65%±0.07 respectively after 22 days. Error bars represent mean±standard deviation with n=3. FIG. 14B illustrates in vitro difference in percent of release between loaded and blank microparticles. The first peak indicates the release of PE from the surface of the particles whereas the second one is likely due to bulk erosion.

FIG. 15 illustrates delivery of PE using gelatin microparticles. The images show the response of HUVECs, seeded with a density of 20,000 cell/$cm^2$, to PE-loaded microparticles after 5 days of culture (D5) compared with HUVECs seeded with blank microparticles (control). The arrows point cells in different conditions: illustrating the difference in shape. After 5 days of culture with PE-loaded particles some sprouts were present but network formation was not observed. The bigger spheres are microparticles.

FIG. 16A illustrates the control with HUVECs cultured at 20,000 cells/$cm^2$ in Angiogenic media; FIG. 16B-16D illustrate HUVECs with, respectively, a single inoculation of hPM occurring on day 1 (FIG. 16B), two inoculations on day 1 and 3 (FIG. 16 C), and three inoculations on days 1, 3, and 5 (FIG. 16D). FIGS. 16E-16G are bar graphs representing the quantification of angiogenesis performed on the images in FIGS. 16B-16D after the staining. Results are shown as the average between measurement on triplicate samples for each condition plus or minus to mean standard error.

FIGS. 17A-17F illustrate evaluation of microparticles. FIGS. 17A-17C illustrate optical microscope images for three protocols evaluated: single (2 min) homogenization (FIG. 17A), dual (2 min/1 min) homogenization (FIG. 17B), and dual (2 min/20 sec) homogenization (FIG. 17C). The histograms of FIGS. 17D-17F illustrate the distribution of the size in microns for the particles formed in each of the 3 protocols, respectively (each batch prepared in triplicate).

FIGS. 18A-18F are scanning electronic microscope (SEM) images of PLGA microparticles loaded with hPM for each of the three protocols: single (FIGS. 18A, 18D), 2/1 dual (FIGS. 18B, 18E), and the 2/20 dual (FIGS. 18C, 18D). FIGS. 18A-18C illustrate the microparticle shape, and FIGS. 18D-18F illustrate the surface porosity.

FIGS. 19A and 19F provide a table (FIG. 19A) of loading efficiency and a graph (FIG. 19B) of the evaluation of the release rate from the particles for each protocol (P2: single, P3: 2/1 dual, and P4 2/20 dual). The curves represent the cumulative release rate up to 21 days for each protocol.

DESCRIPTION

Figure 1F:
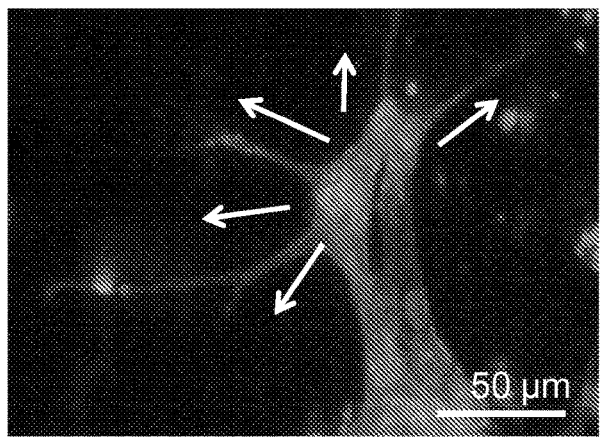

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Any publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, biochemistry, molecular biology, biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent.

Prior to describing the various embodiments, the following definitions are provided and should be used unless otherwise indicated.

Definitions

In describing the disclosed subject matter, the following terminology will be used in accordance with the definitions set forth below.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides, and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The term "gene" or "genes" as used herein refers to nucleic acid sequences (including both RNA or DNA) that encode genetic information for the synthesis of a whole RNA, a whole protein, or any portion of such whole RNA or whole protein. A "gene" typically refers to a hereditary unit corresponding to a sequence of DNA that occupies a specific location on a chromosome and that contains the genetic instruction for a characteristic(s) or trait(s) in an organism. The term "gene product" refers to RNAs or proteins that are encoded by the gene.

The terms "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, delaying or slowing of disease progression, substantially preventing spread of disease, amelioration or palliation of the disease state, and remission (partial or total) whether detectable or undetectable. In addition, "treat", "treating", and "treatment" can also be therapeutic in terms of a partial or complete cure for a disease and/or adverse effect attributable to the disease. As used herein, the terms "prophylactically treat" or "prophylactically treating" refers completely, substantially, or partially preventing a disease/ condition or one or more symptoms thereof in a host. Similarly, "delaying the onset of a condition" can also be included in "prophylactically treating", and refers to the act of increasing the time before the actual onset of a condition in a patient that is predisposed to the condition.

By "administration" is meant introducing a compound of the present disclosure into a subject; it may also refer to the act of providing a composition of the present disclosure to a subject (e.g., by prescribing).

The term "organism," "subject," or "host" refers to any living entity in need of treatment, including humans, mammals (e.g., cats, dogs, horses, mice, rats, pigs, hogs, cows, and other cattle), birds (e.g., chickens), and other living species that are in need of treatment. In particular, the term "host" includes humans. As used herein, the term "human host" or "human subject" is generally used to refer to human hosts. In the present disclosure the term "host" typically refers to a human host, so when used alone in the present disclosure, the word "host" refers to a human host unless the context clearly indicates the intent to indicate a non-human host. Hosts that are "predisposed to" condition(s) can be defined as hosts that do not exhibit overt symptoms of one or more of these conditions but that are genetically, physiologically, or otherwise at risk of developing one or more of these conditions.

The term "expression," as used herein, describes the process undergone by a structural gene to produce a polypeptide. It is a combination of transcription and translation. Expression generally refers to the "expression" of a nucleic acid to produce a polypeptide, but it is also generally acceptable to refer to "expression" of a polypeptide, indicating that the polypeptide is being produced via expression of the corresponding nucleic acid.

"Angiogenesis" is a physiological process involving the growth of new blood vessels. Angiogenesis is an important part of biological processes, such as growth and development, wound healing, embryogenesis, and the like. Excessive angiogenesis can occur when diseased cells produce abnormal amounts of angiogenic growth factors, overwhelming the effects of natural angiogenesis inhibitors. Imbalances between the production of angiogenic growth factors and angiogenesis inhibitors can cause improperly regulated growth or suppression of vascular vessels. Angiogenesis-dependent or related diseases result when new blood vessels either grow excessively or insufficiently. The angiogenesis related disease can include diseases such as, but not limited to, cancer, precancerous tissue, tumors, cardiac infarction, and stroke. Excessive angiogenesis can include: cancer, diabetic blindness, age-related macular degeneration, rheumatoid arthritis, psoriasis, and more than 70 other conditions. Insufficient angiogenesis can include: coronary artery disease, stroke, and delayed wound healing, and is also a factor in tissue engineering as discussed in greater detail in the present disclosure.

As used herein, the term "modulate" and/or "modulator" generally refers to the act of directly or indirectly promoting/activating/inducing/increasing or interfering with/inhibiting/decreasing a specific function and/or trait in a cell/organism. In some instances a modulator may increase or decrease a certain activity or function relative to its natural state or relative to the average level of activity that would generally be expected. Modulation includes causing the overexpression or underexpression of a peptide (e.g., by acting to upregulate or downregulate expression of the peptide), or it may directly interact with the subject peptide to increase and/or decrease activity. Modulation also includes causing the increase or decrease of a specific biological activity or biological event, such as angiogenesis or biological events related to angiogenesis As used herein "upregulate" refers to the act of increasing the expression and/or activity of a protein or other gene product. "Downregulation" refers to decreasing the expression and/or activity of a protein or other gene product.

The term "isolated cell or population of cells" as used herein refers to an isolated cell or plurality of cells excised from a tissue or grown in vitro by tissue culture techniques. The term "a cell or population of cells" may refer to isolated cells as described above or may also refer to cells in vivo in a tissue of an animal or human.

The term "tissue" generally refers to a grouping of cells organized to cooperatively carry out a biological function and/or serve a biological purpose, such as forming all or part of an organ in an organism (e.g., connective tissue, endothelial tissue). While a "tissue" generally includes a grouping of similar cells, or cells of all the same type, a tissue may also include cells of more than one type where the group of cells as a whole serve a common purpose.

As used herein the term "biocompatible" refers to the ability to co-exist with a living biological substance and/or biological system (e.g., a cell, cellular components, living tissue, organ, etc.) without exerting undue stress, toxicity, or adverse effects on the biological substance or system.

The term "bioscaffold" refers to any biocompatible substrate (naturally derived or synthetic) with sufficient structural stability to support the growth of a living biological substance (e.g., living cells). In embodiments of the present disclosure the biocompatible scaffold material is a naturally derived substrate (e.g., procured from a living organism, but that may have undergone additional processing and treatment; or produced from materials derived from a natural source), such as, but not limited to, decellularized human umbilical vein scaffolds, In embodiments, the bioscaffolds of the present disclosure have a three-dimensional structure (rather than a planer, 2-dimensional structure) to support three-dimensional growth of living cells.

As used herein, the term "biodegradable" refers to a material that, over time in a natural environment (e.g., within a living organism or living culture), dissolves, deteriorates, or otherwise degrades and loses its structure integrity and ceases to exist in its original structural form. In embodiments of the present disclosure, biodegradable materials dissolve/degrade over a period of time within a host organism.

As used herein, the term "engineered" indicates that the engineered object is created and/or altered by man. An engineered object may include naturally derived substances, but the object itself is altered in some way by human intervention and design.

As used herein the term "test compound" may include peptides, peptidomimetics, small molecules, nucleic acid sequences, or other compounds that may have an effect on a living cell or organism. In some embodiments the "test compound" may be a compound, such as a chemical or peptide that is suspected of having a modulating effect on a biological activity, function or response to another compound. For instance, in the present disclosure, a "test compound" may be a compound suspected of having a modulating effect on angiogenesis, such as increasing angiogenic activity, decreasing angiogenic activity, and/or modulating the effect of a different angiogenesis modulator.

As used herein, the term "removed" or "substantially removed" indicates that an amount of a substance or compound has been separated from another composition, but does not require that absolutely all traces of the removed substance be absent from the remaining composition, such that the removed substance is completely undetectable. For instance, if blood has been "removed" or "substantially removed" from a composition, this indicates that a substantial proportion of the blood in the composition has been removed, but that some blood or blood components might still be detected in trace amounts upon rigorous screening (e.g., "substantially removed" does not require that a composition be 100% free of the component that has been "removed"; instead, a composition or substance can be about 99% free, about 95% free, or about 90% free of the "removed" component, or any percentage or range within the exemplary percentages, given above).

Discussion

The embodiments of the present disclosure encompass methods and compositions for inducing angiogenesis and methods and compositions for modulating angiogenesis, and methods of making compositions for modulating angiogenesis. The present disclosure also includes methods of identifying modulators of angiogenesis and assays for identifying modulators of angiogenesis. Embodiments of the present disclosure further include methods and compositions for delivering compositions for modulating angiogenesis. In embodiments, the present disclosure includes a placental extract that can be used to induce and/or modulate angiogenesis in vitro and/or in vivo in a tissue construct and/or in natural tissue and methods and compositions for delivering a placental extract to cells in a tissue construct and/or natural tissue. The present disclosure also includes a placental extract that can be used in an assay to identify compounds that modulate angiogenesis. Furthermore, the present disclosure includes a composition of delivery vehicle loaded with placental extract for controlled release of the extract to in vivo or in vitro cell populations to induce angiogenesis.

Angiogenesis is a complex process that is both location and stimuli dependent, and in each instance the capacity to modulate these processes may involve a complex combination of regulatory molecules. Control of vessel formation is further complicated by different mechanisms of formation, with the two most understood being intussusception and sprouting. Intussusception is characterized by the insertion of interstitial cellular columns into the lumen of preexisting vessels, and sprouting is characterized by endothelial cells sprouting toward an angiogenic stimulus in tissue previously devoid of microvessels. Many molecules have been found to modulate angiogenesis, with more likely to be discovered. This diversity of angiogenesis inducers has driven the continued search and development of angiogenesis modulators for use in studies of vascular development, drug screening, and regenerative medicine therapies.

Conventional models to study angiogenesis use either animal-derived stimulators or are entirely dependent on the use of live animals for evaluation. In vivo animal studies provide a more accurate model to compare the complexity of biomolecular pathways and mechanisms that occur during human blood vessel formation. Standard in vivo angiogenesis models include the rabbit corneal neovascularization assay, the in vivo/in vitro chick chorioallantoic membrane assay, and the rat mesentery window assay. When possible, in vitro angiogenesis models are chosen to better control complex biological phenomena; however, this often limits studies to a limited number of molecular species, e.g., VEGF. The outcomes of using a single molecule (or several) for this complex cascade maybe limiting in itself, where a more complex or multifactorial 'mix' may be needed promote competent vascularization.

For in vitro angiogenesis models, the murine derived basement membrane matrix (BMM) or 'Matrige' assay has been the preferred model, as it brings a degree of in vivo complexity to an in vitro model and results appear to be more comparable to in vivo results. It is not suitable for clinical use, however, due to its derivation from Engelbreth-Holm-Swarm (EHS) mouse sarcoma cells and that it requires the sacrifice of large numbers of animals[11]. A number of in vitro human-derived modulators have been used to model angiogenesis. Historically, these have been based on single modulators (FGF, TGF-ß, VEGF) and lack the variety of cytokines and chemical gradients that are native in vivo[12]. Given interspecies differences associated with animal-derived models[13,14] and the complexity of deriving multi-protein formulations from human recombinant proteins, a robust human derived approach (including a more complex mix of multiple proteins at near physiological ratios) would have significant impact for mechanistic studies, screening angiogenesis drugs and the potential to enhance the clinical translation of regenerative medicine therapies. In addition, the capacity to modulate the angiogenic process to represent the different mechanisms and stages of formation would provide an improved platform to characterize key molecules and molecular pathways during vascularization.

The present disclosure provides methods to induce and modulate angiogenesis in vitro and in vivo. In addition to inducing in vitro and in vivo angiogenesis, this model enables modulation of the rate of microvessel network maturation as well as selectively modeling sprouting and intussusceptive angiogenesis. In vivo the human placental extract (PE) was shown to significantly enhance capillary formation while eliminating fibrosis using dosed collagen based bioscaffolds.

The present disclosure describes such methods to induce and modulate angiogenesis in vitro and in vivo using a complex set of tunable, fully-human biomolecules derived from the human placenta. The approach uses directed fractionation and separation techniques to derive a complex of active human biomolecules isolated from the human placenta. In addition to inducing and modulating in vitro angiogenesis and in vivo angiogenesis, the methods and compositions of the present disclosure enable modulation of the rate of microvessel network maturation as well as selectively modeling sprouting and intussusceptive angiogenesis. In embodiments, the methods and compounds of the present disclosure also induce and modulate angiogenesis in both polymeric and ex vivo derived tissue scaffolds. These methods enable modulation of the rate of microvessel network maturation. In vivo, the human placental extract of the present disclosure was shown to significantly enhance capillary formation while eliminating fibrosis using dosed collagen based bioscaffolds.

Sustained delivery of growth factors effecting angiogenesis is also a challenge facing successful modulation of angiogenesis to promote vascularization for tissue engineering approaches. The present disclosure also provides methods and compositions for controlled release of the compositions of the present disclosure for modulating angiogenesis both in vitro and in vivo.

Human Placental Extract

The present disclosure provides a composition and methods for induction and/or modulation of angiogenesis that includes a human placental extract (PE or hPE). In embodiments of the present disclosure, the PE is made by obtaining a sample from a human placenta, removing blood from the placental sample to produce a crude placental extract (crude PE), mixing the crude PE with urea or other protein solubilization agent to solubilize the proteins present in the extract, removing remaining solids from the crude extract; dialyzing the urea-placental extract mixture to remove a substantial amount of the urea from the mixture to produce the human PE. The human PE is a matrix-like compound, and is sometimes referred to herein as a human placental matrix (hPM).

In embodiments, the process to make the human PE is performed at temperatures between about −86° C. and about 5° C. In embodiments, the human placental extract is made at temperatures at or below about 4° C.

In embodiments, the process of removing blood from the placental sample to make a crude placental extract includes homogenizing the human placenta sample with a buffer, centrifuging the homogenized sample, and discarding the supernatant containing blood. This process can be repeated multiple times (e.g., 2, 3 or more times) until substantially all of the blood has been removed from the sample (e.g., the sample is about 99% free of blood, about 95% free of blood, about 90 percent free of blood, etc.) to produce a crude PE. In an embodiment, the buffer is a Sodium Chloride solution (NaCl).

In embodiments, the proteins in the crude placental extract are solubilized by mixing the crude placental extract with a protein solubilization agent. In embodiments, the protein solubilization agent can be any compound or mixture of compounds capable of solubilizing (e.g., denaturing) proteins without permanently destroying the proteins or otherwise permanently rendering them inactive (e.g., the solubilization should reversibly denature the proteins, such that the proteins are capable of refolding, such as upon removal of the protein solubilization agent). In embodiments the protein solubilization agent can be, but is not limited to, urea, guanidine-HCl, or other similar compounds. In embodiments, the protein solubilization agent is urea, and the crude extract is mixed with a urea composition by homogenizing the crude extract with urea. In embodiments, the urea is mixed with the crude extract for a period of time between about 12 and about 36 hours. In embodiments, the urea is mixed with the crude extract for about 24 hours. In embodiments the urea solution is a urea buffer having about 0.5M concentration of urea or greater. In embodiments, the urea is about 2M or greater, about 4M urea, or greater, up to about 15M. In embodiments, the urea solution can have a concentration of about 0.5M to about 15M. In other embodiments the protein solubilization agent is guanidine-HCl having a concentration of about 0.5M to about 15M. In embodiments the guanidine-HCL has a concentration of about 6M. Although the methods and compositions described below are described using urea as the solubilization agent, it is to be understood that other suitable solubilization agents, such as, but not limited to, those discussed above, can be substituted for urea.

In embodiments, after mixing with urea, or other protein solubilization agent, solids are removed from the solubilized protein-crude extract mixture (e.g., urea-crude extract mixture). In embodiments, the solids are removed by centrifuging the PE mixture and discarding the pellet (containing the solids). This step can be repeated multiple times. After removal of the solids, the PE mixture (e.g., the supernatant) is dialyzed to remove urea, or other protein solubilization agent, from the placental extract. In embodiments, the dialysis solution is TBS. In embodiments, the dialysis solution is changed after a period of time (e.g., 1 hour, 2 hours, 3 hours, etc.) and dialysis is repeated a number of times (e.g., 2, 3, 4, etc.) to remove substantially all urea from the PE (e.g., the placental extract is about 99% free of urea, about 95% free of urea, etc.). In embodiments, the PE may be centrifuged again to remove remaining solids (e.g., polymerized proteins, and the like). In embodiments, the remaining PE is a clear to pinkish viscous substance. Additional details about embodiments of the process of the present disclosure of making the placental extract of the present disclosure can be found in the Examples below.

Thus, embodiments of the present disclosure also include a PE made by the methods of the present disclosure. In embodiments, the present disclosure includes a PE made by removing blood from a sample obtained from a human placenta sample to produce a crude PE; mixing the crude placental extract with a protein solubilization agent (such as, but not limited to urea, guanidine-HCl, etc.) to solubilize proteins in the crude extract; separating solid materials from the solubilized protein-PE mixture; and performing dialysis on the PE mixture to remove the protein solubilization agent (e.g., urea) from the mixture to produce the human PE.

The present disclosure thus includes a human placental extract including an extract obtained from a human placenta (e.g., from a human placental sample) having the blood and solids substantially removed and retaining (some or all) of the placental proteins that were present in the placental sample. In embodiments, the placental proteins include cytokines and growth factors.

Analysis of the PE of the present disclosure reveals that the PE includes many proteins including many cytokines and growth factors. In embodiments of the placental extract of the present disclosure, the extract includes at least 20 different cytokines. In some embodiments it contains up to 40 different cytokines. Other embodiments include at least 50 cytokines. Some cytokines that can be present in the PE of the present disclosure include those listed in the example below. For instance, some of the cytokines that can be present in the PE of the present disclosure include, but are not limited to, angiogenin, Acrp30Ag, IGFBP-1, NAP-2, and Fas/TNFGSF6, and RANTES, and MIF.

The cytokines and growth factors and other placental compounds present in the placental extract of the present disclosure can induce angiogenesis in a culture of endothelial cells, a tissue, a tissue construct, an engineered bioscaffold, and the like. The placental extract of the present disclosure can induce angiogenesis in vitro and in vivo. The placental extract of the present disclosure is capable of stimulating growth of endothelial cells. In embodiments the human PE of the present disclosure is capable of modulating angiogenesis. Compared to other conventional compounds used for inducing angiogenesis, such as BMM (compounds including single purified angiogenesis modulators (such as purified VEGF-alpha or SDF-1) and purified fibrin) the PE of the present disclosure stimulates increased angiogenic growth of endothelial cells (e.g., tubule and network formation) and decreased angiogenic-type growth of myofibroblasts (e.g., tubule formation) as compared to BMM. The PE of the present disclosure also stimulates different growth and/or differentiation patterns for various cell lines (e.g., stem cells, smooth muscle cells, etc.) as compared to BMM, such that the growth/differentiation patterns of such cells are distinguishable from growth with BMM.

The PE of the present disclosure is also capable of upregulation of various genes in endothelial cells in comparison to endothelial cells grown in the absence of the PE. Some such genes include angiogenesis related genes, extracellular matrix remodeling genes, and vascular development genes. Some angiogenesis related genes include, but are not limited to: ANGPTL4, CXCL3, human growth factor (HGF), ANGPT2, PGF, TYMP, VEGFA, HIF1A, and FGF1. Some extracellular matrix remodeling genes that can be induced by the placental extract of the present disclosure include, but are not limited to: MMP2, MMP9, COL4A3, and LAMA5. Vascular development genes include, but are not limited to: CDH2, HAND2, LECT1, and MDK.

Methods for Modulating Angiogenesis

The present disclosure also includes methods for inducing angiogenesis in a cell culture, wherein the method includes growing endothelial cells in the presence of a human placental extract of the present disclosure. In embodiments the cell culture is grown in the presence of a placental extract of the present disclosure obtained from a human placenta sample that was treated to remove blood and solids, mixed with urea, and dialyzed to remove urea, wherein the placental extract comprises placental proteins including cytokines and growth factors. In embodiments, the endothelial cells are human endothelial cells; in yet other embodiments, the cells are human umbilical vein endothelial cells (HUVECs). In embodiments of the methods of inducing angiogenesis in cell culture, the cells are seeded at a density of at least about 40,000 cells/cm$^2$. In embodiments they are seeded at a density of at least about 80,000 cells/cm$^2$. In embodiments, the cell cultures can be grown on a plate containing growth media and the placental extract of the present disclosure.

The present disclosure also include methods for inducing vascularization of a biomaterial in vivo including incubating a biomaterial in a composition including the human placental extract of the present disclosure and implanting the biomaterial in the host. In embodiments, the biomaterial includes naturally derived materials and/or cells. In embodiments the biomaterial includes an engineered bioscaffold including human derived substrate material. In embodiments, the engineered bioscaffold includes human umbilical vein scaffold. In embodiments the human umbilical vein scaffold is decellularized. In some embodiments, the biomaterial is seeded with endothelial cells, such as, but not limited to, human endothelial cells (e.g., HUVECs). In embodiments of the present disclosure the biomaterial includes an engineered scaffolding material including a human umbilical vein scaffold seeded with HUVECs). In some embodiments, the HUVECs are seeded on the bioscaffold at a cell density of at least about 40,000 cells/cm$^2$. In embodiments they are seeded at a density of at least about 80,000 cells/cm$^2$. In embodiments the biomaterial is incubated in the placental extract for at least about 2 hours.

Vascularization of Biomaterials and Engineered Bioscaffolds

The present disclosure also includes methods of vascularizing biomaterials, including but not limited to, engineered biomaterials, naturally derived biomaterials, and other biomaterials to be implanted in a host. In addition to vascularization of biomaterials, treatment of biomaterials with the placental extract of the present disclosure can also be used to pre-treat biomaterials for use in-vivo to aid in bio-acceptance, reduce inflammation, reduce rejection and scarring, etc. Thus, the placental extract of the present disclosure and compositions including the placental extract of the present disclosure can be used to "dose" any number of biomaterials in order to improve the outcome of such implant.

The present disclosure also includes specifically engineered biomaterials, such as implantable, engineered bioscaffolds including a human derived substrate material incubated in a composition including a human placental extract of the present disclosure. The bioscaffolds of the present disclosure can be implanted in a mammal, such as a human. Bioscaffolds of the present disclosure can include any biomaterial suitable for implantation in a host. Examples of bioscaffolds for use in the present disclosure include, but are not limited to, engineered bioscaffolds including tissue, matrix materials, any number of naturally derived biomaterials, and the like. In embodiments, the bioscaffolds are 2D or 3D bioscaffolds. In embodiments, the bioscaffolds includes human derived substrate material. In embodiments, the bioscaffold includes decellularized human umbilical vein scaffold. In embodiments, the bioscaffold is seeded with cells, such as, but not limited to human cells, human endothelial cells (e.g., human umbilical vein endothelial cells (HUVECs)), stem cells, other pluripotent cells, and the like.

As described in the Examples below, the bioscaffolds of the present disclosure incubated in the placental extract of the present disclosure induce more vascularization (e.g., angiogenesis) and less fibrosis that bioscaffolds incubated in the angiogenesis inducing compound BMM or a control compound. The bioscaffolds incubated in the placental extract of the present disclosure also had a higher ratio of immune suppressive and pro-angiogenic positive macrophages (e.g., CD205(M2)) versus proinflammatory positive macrophages e.g., (CD86(M1)) as opposed to bioscaffolds incubated in BMM or a control.

Angiogenesis Screening Assays

Since the placental extract of the present disclosure induces angiogenesis in cell culture it provides a good assay for identifying and screening for angiogenesis modulators. Thus, the present disclosure also includes methods and assays for identifying angiogenesis modulators.

In embodiments, a method includes growing a culture of human endothelial cells in the presence of a compound including a human placental extract of the present disclosure and contacting the human endothelial cell culture with a test compound. Since the placental extract induces angiogenesis in the cell culture, if angiogenesis is less than or more than expected, the test compound can be identified as an angiogenesis modulator. Thus, the method also includes determining an amount of angiogenesis in the culture and identifying the test compound as an angiogenesis modulator when the amount of angiogenesis in the cell culture is greater or less than the amount of angiogenesis is a culture growth in the absence of the test compound. In embodiments an increase in the amount of angiogenesis relative to a culture grown in the absence of the test compound indicates the test compound induces angiogenesis. A decrease in the amount of angiogenesis relative to a culture grown in the absence of the test compound indicates the test compound inhibits angiogenesis. As described in the examples below, a screen of the compound Thrombospondin-1 (TSP-1) according to the methods of the present disclosure identified the compound as an inhibitor of angiogenesis. The present disclosure also provides assays for screening test compounds to identify modulators of angiogenesis including a culture of endothelial cells grown in the presence of a human placental extract of the present disclosure. The assays of the present disclosure can be used with the methods of the present disclosure to identify modulators of angiogenesis.

Sustained Delivery Methods and Compositions

Since the angiogenic effects of the placental extract may not be sustained in vivo or in a biomaterial (e.g., tissue, cell culture, bioscaffold, etc.) for a prolonged period of time, compositions and methods for sustained release of the PE of the present disclosure are also provided in the present disclosure.

Embodiments of the present disclosure include a composition including the human PE (hPE) of the present disclosure coupled to biodegradable microparticles to provide a sustained-release/human PE composition. The PE loaded biodegradable microparticles provide a sustained release angiogenesis-modulating composition. Thus, in embodiments, the sustained-release angiogenesis-modulating composition includes, a human PE of the present disclosure and biodegradable microparticles, where the human PE is coupled to the microparticles such that the human PE is released from the microparticles. In embodiments, the human PE is obtained from a human placental sample and having the blood and solids substantially removed from the extract, where the extract includes placental proteins that were present in the placental sample, including cytokines and growth factors. The human PE used in the sustained-release angiogenesis-modulating composition can be any embodiment of the human PE as described above.

In embodiments, the human PE is released from the microparticles after exposure to cells in vivo or in vitro. In embodiments, when the biodegradable microparticles are placed in a host in vivo or in contact with cell culture or cell seeded bioscaffold in vitro, the biodegradable microparticles begin to degrade and release the PE to the surrounding cells, tissues, etc. over time. In embodiments the biodegradable microparticles release an initial "burst" of the PE and then slowly release PE over a sustained period of time (e.g., several days, weeks, etc.). The release profile of the microparticles can be controlled by varying the size of the microparticles and the degree of crosslinking. In embodiments, the microparticles are crosslinked and the degree of crosslinking can be controlled to modify the release parameters of the particles.

In embodiments, the biodegradable microparticles are made of gelatin. Further details about embodiments of gelatin biodegradable microparticles are described in Example 2, below. In embodiments, the biodegradable microparticles include a mixture of different sizes of microparticles. It is believed that including various sizes of microparticles provides sustained release of PE since different size particles release PE at different rates.

In embodiments, the biodegradable microparticles are poly(lactic-co-glycolic acid) (PLGA) microparticles. In embodiments, the hPE is loaded into (e.g., encapsulated) in the PLGA microparticles. In embodiments the PLGA microparticles loaded with the hPE of the present disclosure have an average particle size of about 10 to about 1000 μm. In embodiments, the PLGA microparticles are made by an oil in water emulsion process including a dual homogenization step. In embodiments, the PLGA microparticles are made by mixing a PLGA oil solution with a first water solution (W1) including the hPE of the present disclosure, preparing a first emulsion by homogenizing the PLGA and W1 in a first homogenization step, and adding the first emulsion to a second water solution (W2) including a solvent (e.g., and alcohol, such as, but not limited to, polyvinyl alcohol) in water to form a second emulsion (a water-in-oil-in-water emulsion), and then the solvent is evaporated. In embodiments, a second homogenization step is used to homogenize the secondary emulsion. In embodiments, the first homogenization is from about 1 to about 2 minutes. In some embodiments, no other homogenization step is used. In other embodiments, a second homogenization step is added. In embodiments, the second homogenization is from about 20 seconds to about 1 minute. Additional details about embodiments of methods of preparing the hPE loaded PLGA microparticles are provided in Example 3, below. In embodiments, hPE loaded PLGA microparticles made with a single homogenization step have size of about 100 to about 1000 μm in diameter. In embodiments where the single homogenization step is about 2 min, the resulting microparticles have sizes ranging from about 50 to about 500 μm in diameter, with an average of about 260 to about 290 μm in diameter. In embodiments, hPE loaded PLGA microparticles made with a second homogenization step of about 1 min range in size from about less than 20 to about 100 μm in diameter, with an average of about 36 to about 40 μm in diameter. In embodiments, hPE loaded PLGA microparticles made with a second homogenization step of about 20 sec range in size from less than 20 to about 200 μm, with an average of about 85 to about 95 μm in diameter.

The present disclosure also includes methods of using the sustained release angiogenesis-modulating composition described above for sustained release of PE. In embodiments methods include using the sustained release composition to obtain sustained release of human PE in vivo or in vitro, such as, but not limited to, sustained release of human PE to a biomaterial (e.g., cell culture, tissue, tissue construct, bioscaffold, etc.) in vivo or in vitro, over time. In embodiments a method of the present disclosure includes contacting a cells (e.g., cells in culture, cells in vivo, cells in a biomaterial or cells in contact with an engineered biomaterial, etc.) with a sustained release angiogenesis-modulating composition described above including biodegradable microparticles coupled to a placental extract of the present disclosure, such that the human placental extract is released from the microparticles into the biomaterial over a period of time after exposure of the microparticles to the cells. In embodiments the cells are endothelial cells, such as, but not limited to, human umbilical vein endothelial cells (HUVECs).

In embodiments, the sustained release angiogenesis-modulating composition is coupled to a biomaterial. In embodiments, the biomaterial is a cell culture. In embodiments, the biomaterial is a tissue construct and/or tissue matrix including a cell culture. In embodiments, the biomaterial is an alginate matrix including cells (e.g., human cells, e.g., HUVECs) embedded in the alginate matrix and the sustained release angiogogeneisis-modulating composition (e.g., hPE loaded biodegradable microparticles) is also embedded or contacted with the alginate matrix. In embodiments, the biomaterial coupled to the sustained release angiogenesis-modulating composition is implanted in a subject and induces vascularization of the biomaterial. In embodiments, the biomaterial is an engineered bioscaffold including human derived substrate material, such as, but not limited to, decellularized human umbilical vein scaffold seeded with human endothelial cells. In embodiments, the subject is a mammal; in embodiments, the subject is a human. Other variations of the method of inducing angiogenesis with the sustained release angiogenesis-modulating composition of the present disclosure are possible, and exemplary embodiments of the method are described in greater detail in the examples below.

Anti-Inflammatory Compositions and Methods of Use

As described in the examples below, it was also found that the human PE of the present disclosure and the sustained release/human PE compositions of the present disclosure had anti-inflammatory effects on surrounding cells and tissues. Thus, compositions of the present disclosure also include anti-inflammatory compositions including the human PE or the sustained-release/human PE composition of the present disclosure. Methods of the present disclosure also include methods of treating (e.g., reducing, ameliorating, counteracting, preventing, etc.) inflammation in a subject, or a tissue of a subject by exposing a subject or a tissue to the human PE or the sustained-release human/PE composition of the present disclosure.

Additional details regarding the tests and methods of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Induction and Modulation of Angiogenesis in Ex Vivo Derived Bioscaffolds Using Placenta Derived Extracts Introduction The present example describes methods to induce vascularization using a complex human placental extract (PE). The PE is derived from the human placenta and is capable of inducing angiogenesis in 2D and 3D in vitro models, as well as in vivo within bioengineered tissue implants. This example also describes using the placental extract to positively screen thrombospondin-1 as an angiogenesis inhibiting protein with increased sensitivity relative to current in vitro models. Notably, this model allows for modulation over the rate and type (intussusceptive vs. sprouting) of angiogenesis and presents many advantages over conventional approaches as well as broad applications in the fields of regenerative medicine and pharmaceutics.

Mass transfer limitations within tissues represent one roadblock to producing effective biomaterials. Even if this can be temporarily overcome to allow improved cell migration within a human bioscaffold, the creation of an effective vasculature remains the primary goal to provide long-term nutrient delivery to thick, cell-dense materials. In adults, new blood vessels are predominately produced through the physiological process of angiogenesis,[47] which ultimately leads to the formation of nutrient rich vascular networks. The present example demonstrates that angiogenesis can be induced in a human umbilical vein (HUV) vascular graft and lead to a long-term nutrient delivery system.

The successful vascularization of engineered organs and the in vivo repair of infarct tissues through angiogenic modulators has been a major roadblock to delivering successful regenerative medicine therapies to the clinic. A variety of different approaches have been taken to initiate angiogenesis and drive larger vessel formation, including direct cell seeding (mono and co-cultures), stem cells, and combinations of human-derived modulators/growth factors. To date there has been little success in translating these in vitro approaches that typically use non-human animal compounds to the clinic.

A significant issue in the field is that the most popular/successful approach (Matrigel or Basement Membrane Matrix) is derived from Engelbreth-Holm-Swarm mouse sarcoma cells and as such is inappropriate for human therapies. Thus, an approach or mechanism using human-based materials—that actively promotes vessel formation both in in vitro and in vivo systems would have significant impact. The present example provides a human placenta extract (hPE) that is capable of inducing angiogenesis in 2D and 3D in vitro models, as well as in vivo within bioengineered tissue implants. The PE is a complex of active human biomolecules, and the present example demonstrates that, in addition to inducing in vivo and in vitro angiogenesis in the ex vivo derived human umbilical vein vascular graft, this model enables modulation over the rate and stage of angiogenesis. This example also demonstrates that the PE enhances capillary formation while also reducing fibrosis using dosed collagen based bioscaffolds.

Methods

Placental Extract Derivation.

Full-term placentas were collected from UF Health Shands Hospital (Gainesville, Fla.) within 12 hours of birth. The umbilical cords and fetal membranes were removed and the placenta was dissected into 2 cm cubes and frozen. 12 hours after progressive freezing to −86° C. at a rate of −1° C./min, the placental cubes were transported to a cold room maintained at 4° C. where the rest of the procedures were completed. Once at 4° C., 100 grams of the tissue was mixed with 150 mL cold 3.4 M NaCl buffer (198.5 g NaCl, 12.5 ml 2M tris, 1.5 g EDTA, and 0.25 g NEM in 1 L distilled water). The NaCl buffer/tissue mix was homogenized into a paste using a Tissuetek Homogenizer at 3200 RPM, then centrifuged at 7000 RPM for 15 minutes and separated from the supernatant. This NaCl washing process was repeated two additional times, discarding the supernatant each time to remove blood.

Next, the pellet was homogenized in 100 mL of 4M urea buffer (240 g urea, 6 g tris base, and 9 g NaCl in 1 L distilled water), stirred on a magnetic stirplate for 24 hours, and then centrifuged at 14000 RPM for 20 minutes (Sorvall RC6+ Centrifuge, Thermo Scientific, NC, USA). The supernatant was removed and dialysed using 8000 MW dialysis tubing (Spectrum Laboratories, Inc., CA, USA) placed in 1 L of TBS (6 g tris base and 9 g NaCl in 1 L distilled water) and 2.5 ml of chloroform for sterilization. The buffer was replaced with fresh TBS 4 more times, each at 2 hour intervals. Finally, contents of the dialysis tubes were centrifuged at 3000 RPM for 15 min (Allegra X-12R Centrifuge, Beckman Coulter, Inc., CA, USA) to remove polymerized proteins, and the supernatant (pink viscous lysate) was collected and stored at −86° C. until use.

Biomolecular Composition Analysis.

Relative cytokine levels were determined using a sandwich immunoassay array from RayBiotech, Inc. (Human Cytokine Antibody Array C Series 1000, Inc, GA, USA). Chemilumenescence was detected using a Foto/Analyst Luminaryfx Workstation (Fotodyne Incorporated, WI, USA) and the signal intensities were measured using TotalLab 100 software (Nonlinear Dynamics, Ltd, UK). The relative abundance of basement membrane biomolecules was performed by MSBioworks (Ann Arbor, Mich.) using nano LC/MS/MS with a Waters NanoAcquity HPEC (Waters, Milford, Mass.) system interfaced to a Orbitrap Velos Pro (ThermoFisher, Waltham, Mass.). Proteins were identified from primary sequence databases using Mascot database search engine (Boston, Mass.).

RT-PCR Analysis of Cells from hPL-Induced Angiogenic Networks.

Relative angiogenic gene expression was determined using 384-well $RT^2$ Human Angiogenesis $RT^2$ Profiler PCR Arrays (PAHS-024A, Quiagen, CA, USA). ECs were detached from culture plates using Accutase (Innovative Cell Technologies, San Diego, Calif.) and immediately stored in 100 µl of RNAlater. RNA was extracted using the RNeasy Mini Kit (Qiagen, CA, USA), and genomic DNA was digested using an RNase-Free DNase kit (Quiagen, CA, USA). Purified RNA was reverse transcribed to cDNA using the $RT^2$First Strand Kit (SA Biosciences, TX, USA) with incubation at 42° C. for 15 minutes followed by incubation at 95° C. for 5 minutes to stop the reaction. Next, cDNA was mixed with $RT^2$ SYBR Green Mastermix (SA Biosciences, TX, USA) and loaded into 384-well Human Angiogenesis PCR Arrays. Using the Bio Rad CFX384 Real-Time System (Bio-Rad, CA, USA) the loaded array plates went through a denaturization cycle for 10 min at 95° C., 40 cycles of 30 sec annealing/extension cycles at 60° C., and finally melting curves were obtained by ramping from 60° C. to 95° C. at a rate of ° C. per second. Data was analyzed the -using $\Delta\Delta C_t$ method and the $RT^2$ Profiler PCR Array Data Analysis Template v4.0 software package (Quiagen, CA, USA).

Human Umbilical Vein Endothelial Cell Isolation and Myofibroblast Cell Culture.

Endothelial cells were derived from human umbilical veins (collected from UF Health Shands Hospital, Gainesville, Fla.) by detachment from the vessels walls using a 1 mg/ml solution of bovine Type-I Collagenase in phosphate buffered saline (Gibco, Invitrogen, NY, USA). The primary derived human umbilical vein endothelial cells (HUVEC) were used between passages 1-3 for all experiments. For proliferation, cells were cultured using complete VascuLife Basal media (VascuLife VEGF Medium Complete Kit, Lifeline, MD, USA). For angiogenesis experiments, endothelial cell media was prepared using VascuLife Basal media with 25 ml of glutamine, 0.5 ml of hydrocortisone, 0.5 ml of ascorbic acid, 10 ml of FBS, and 1.25 µl of bFGF to 500 mL of (VascuLife VEGF Medium Complete Kit, Lifeline, MD, USA). Human myofibroblasts (CRL 2854) were used between passages 5 and 10 (ATCC, Manasses, Va.) and cultured using 10% FBS supplemented low-glucose DMEM.

Preparation of Placenta Extract-Derived Angiogenesis Assays.

Unless otherwise stated, 32 µl of placental extract was thawed and pipetted into each well of a 96 well plate. The extract was evenly coated onto the bottom of each well using an orbital shaker at 30 RPM for 1 minute. The coated plate was then incubated at 37° C. for 30 minutes. HUVEC were then plating by direct pipetting at 20000 cells/cm$^2$, 40000 cells/cm$^2$, or 80000 cells/cm$^2$. Multiple time points were investigated at each concentration including at days 1, 3, and 5. Thrombospondin-1 was tested as an angiogenesis inhibiting drug using final concentrations 0, 5, 10, 20, and 35 µg/µL diluted in endothelial cell media Morphological Characterization of Angiogenic Networks.

Network formation was analyzed after staining at a concentration of 2 µg/mL Calcein AM (Invitrogen-Life Technologies, NY, USA) with Endothelial cell culture media. In a dark room, dyed cells were incubated at 37° C., 5% $CO_2$ for 30 minutes, and then images were taken using a Zeiss Axiovert 200 inverted Fluorescence microscope (Zeiss, Thornwood, N.Y.). Images were analyzed to determine the tubule length, tubule width, branch points, and other meshwork characterizations using ImageJ 1.45s (NIH, Bethesda, Md.). Branch points were assigned manually as the positions at every node where branches meet or tubules sprout, and tubule length was assessed by determining the curve length from branch point to connected branch point. Tubule width measurements were carried out in three different zones per tubule, with two zones each 10 µm from the start and end and one zone in the middle of the curve length. The percent area of coverage was determined by processing the images using the imageJ function "binary>>convert to mask" followed by measurement of the "mean." In TSP-1 experiments, final values were normalized to no dose samples, calculated as the percentage of "1" values relative to the total count of pixel values, and given as "% area coverage".

For scanning electron microscopy analysis of morphology, microvessel networks grown on glass slides were fixed in 2.5% glutaraldehyde, washed in PBS, fixed in 1% osmium tetroxide solution, and progressively dehydrated in 25%, 50%, 75%, 85%, 95%, and 3×100% ethanol solutions. Samples were then critical point dried, coated with gold/palladium, and imaged using a Hitachi S-4000 FE-SEM.

Human Umbilical Vein Scaffold Derivation and Placental Extract Incubation.

Placentas were collected from UF Health Shands HospitalFlorida (Gainesville, Fla.) and HUVs were dissected using an automated method as previously described.[32] Dissected HUV samples were decellularized in a 1% SDS (Thermo Scientific, Rockford, Ill.) solution at a solvent/tissue mass of 20:1 (w:v). Samples were decellularized on an orbital shaker plate at 100 rpm for 24 hours and then rinsed with PBS prior to incubation overnight at 37° C. in a 70 U/mL DNase I solution (Sigma-Aldrich, St. Louis, Mo.) in PBS. Sample were terminally sterilized using a 0.2% peracetic acid/4% ethanol (Sigma-Aldrich, St. Louis, Mo.) solution for 2 hours and finally pH balanced (7.4) using PBS. Following decellularization, scaffolds were cut into 1.5 cm×1.5 cm×0.075 cm sheets, prefrozen to −85 C, and then lyophilized using a Millrock bench top manifold freeze dryer (Kingston, N.Y.) for 24 hours at −85 C under 10 mT vacuum. Immediately prior to cell seeding, scaffolds were soaked for 2 hours in hPE, Matrigel, or PBS (control) and seeded.

Animal Implant Revascularization Study.

Male Sprague-Dawley rats (6 month old, 200 g) were purchased from Charles River Laboratories (Wilmington, Mass., USA), and all procedures were approved by the University of Florida IACUC (UF#201207728). In a biological hood, terminally sterilized HUV scaffolds were incubated for 2 hours in 5 mL of hPE, MATRIGEL, or PBS (control), respectively. Animals were anesthetized using isoflurane inhalation, and subcutaneous pockets were created on the left and right side of the back by blunt preparation with scissors. One scaffold was inserted into each subcutaneous pocket, and skin was sutured using 4-0 sutures (Coviden, Mansfield, Mass.). After 5 days implantation, animals were euthanized, and samples were removed for analysis.

To analyze capillary network formation, immediately after removal from the animal, fibrotic capsules were dissected with a scalpel and the HUV samples were placed onto glass slides. Top-down images of the semi-translucent scaffold sheets were taken using an Imager M2 light microscope (Zeiss, Oberkochen, Germany) with an Axiocam HRm digital camera (Zeiss, Oberkochen, Germany). To quantify cell migration and scaffold remodeling, tissue samples were embedded in Neg-50 frozen section medium, sectioned into 7 μm sections (Microm HM550 cryostat, Thermo Scientific, Waltham, Mass.), and stained using standard hematoxylin and eosin (H&E) staining (Richard-Alan Scientific, Kalamazoo, Mich.).

Statistics.

Results are reported as mean±standard deviation. Linear regression was performed using SPSS (IBM, Somers, N.Y.). Rt-PCR data was analyzed using $RT^2$ Profiler PCR Array Data Analysis Software v3.2 (SABiosciences, Valencia, Calif.).

Perfusion Bioreactor Culture and Angiogenesis Induction in the HUV Bioscaffold.

Cell-seeded tubular constructs were cultured in dual perfusion bioreactors (FIG. 7) for 5 days with a lumenal flow rate of 4 mL/min at 60 pulses/min. Shear stress on the vessel-wall was calculated using the Haagen-Poisseuille equation, under the assumptions that the flow of media is steady and laminar and the vessel is inelastic, cylindrical, and straight:[134]

$$\tau = 32 * \mu * \frac{Q}{\pi * d^3}$$

where Q is the mean volumetric flow rate and p is equal to the kinetic viscosity of water at 37° C. (0.000692 kg/(m*s)).[134] The shear stress cycled from 0 dynes/cm² to 0.04 dynes/cm² during each pulse. The environment was maintained under standard cell culture conditions of 37° C. and 5% $CO_2$. Pressure within the system was maintained at negligible levels (<2 mmHg) in both the ablumenal and lumenal flow circuits resulting in no pressure gradient existed across the scaffold. Culture media in the bioreactor was replenished every two days. After 5 days of perfusion culture, the 10 cm long tubular scaffolds were dissected into ringlets for histological analysis.

Results

Derivation and Characterization of Human Placental Extract

After initial mechanical homogenization and centrifugation, the hPE derivation technique utilized a urea step to linearize and solubilize molecules. This was followed by dialysis separations to remove urea and allow the biomolecules to refold into their original conformations (FIG. 1A). All steps of the derivation were performed in a cold room at 4° C. The final solution of PE was translucent, highly viscous, and consisted of biomolecules between 8 kD to 868 kD.

The hPE could be used to soak biomaterials or made into a thin-film for tissue culture assays. Reproducibility of hPE was assessed by analysis of standard deviation of the total protein content in n ¼ 3 batches of hPE (with each batch created using equal masses of tissue from 3 separate donors) and shown to have a have a similar reproducibility and protein content to Matrigel®. Scanning electron microscopy images show the surface morphology of hPE (FIG. 1B-1C) and angiogenic network formation when HUVECS were seeded at 4×10⁴ cells/cm² onto hPE thin films and cultured for 3 days (FIG. 1D-1E).

Figure 1G:
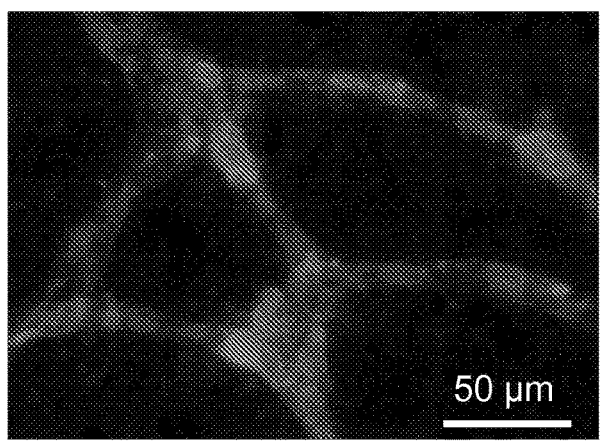
Figure 1H:
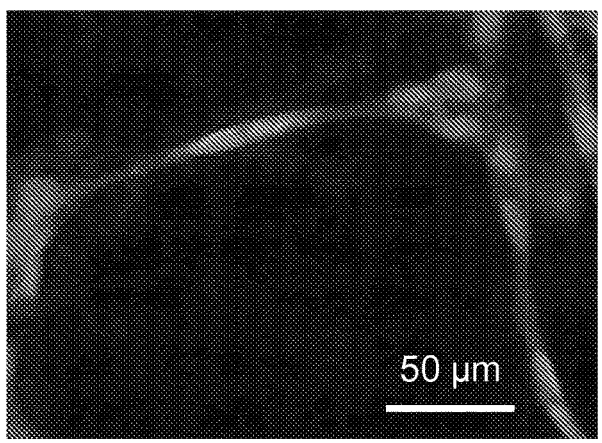
Figure 1I:
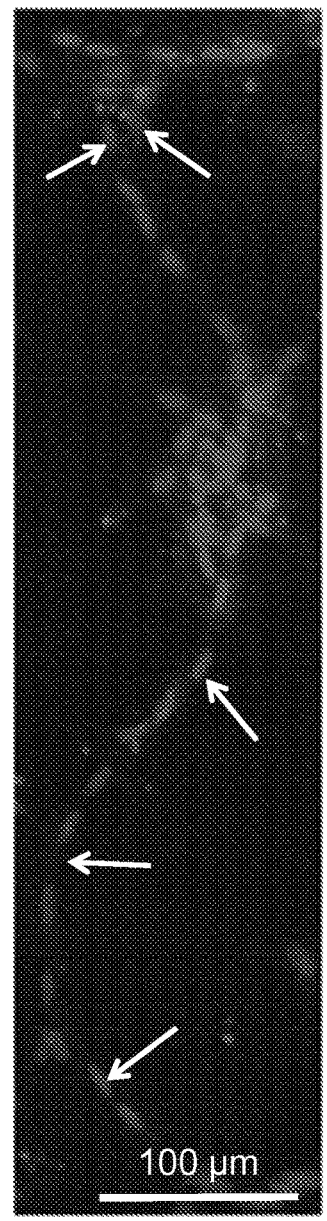
Figure 1J:
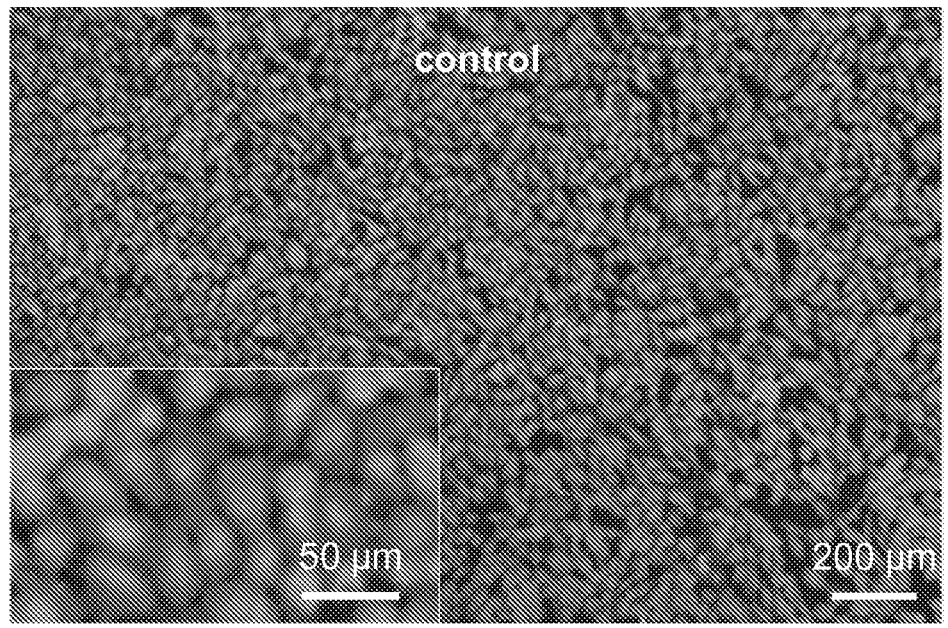
Figure 1K:
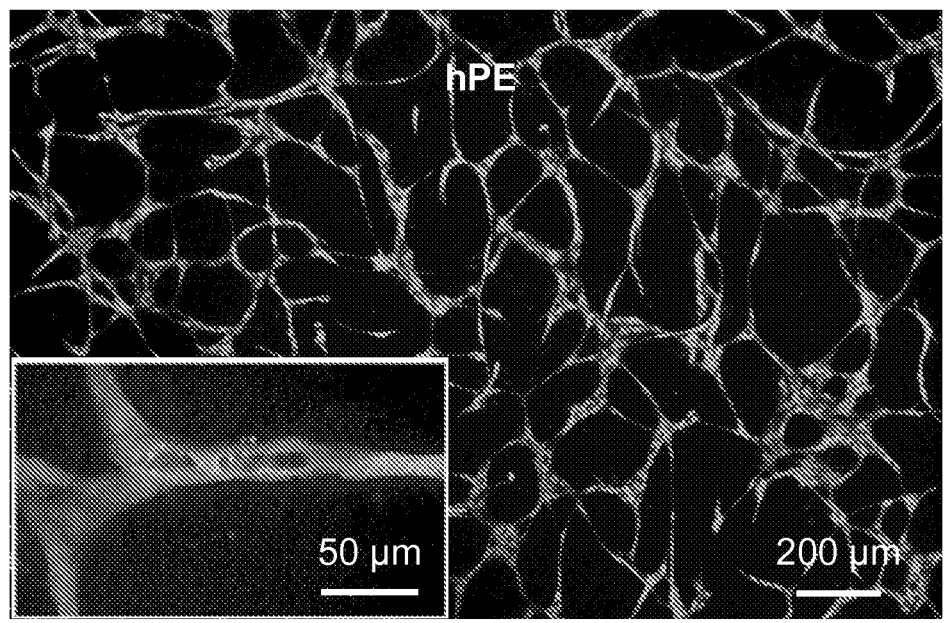

Angiogenic potential of the human placental extract (hPE) was initially characterized by seeding primary human umbilical vein endothelial cells (HUVEC) onto tissue culture plates (TCP) coated with the hPE. Early stage cell cording and sprouting were visible within 1 hour of cell seeding (data not shown), and angiogenic networks continued to mature until experimental termination at 3 d (FIG. 1F-1G). The length of individual cell cords (multicellular) increased significantly from day 1 (FIG. 1H) to day 3 (FIG. 1I) of seeding. After 3 days of culture, cells had formed extensive angiogenic networks relative to control samples (FIG. 1J, 1K).

Biomolecular Characterization of Placental Extract

Of the 120 cytokines assessed, 54 angiogenesis related cytokines were detected in the placental lysate (FIG. 2A). The most prevalent angiogenesis related chemokine was angiogenin, which is a potent stimulator of new blood vessel formation[16]. Significant pro-angiogenic chemokines including, but not limited to, hepatocyte growth factor (HGF), fibroblast growth factor-4 (FGF4), leptin (LEP), ICAM-1, ICAM-2 and TIMP-2 were also detected. LC-MS/MS showed the presence of immune-related proteins including annexins (ANXA1, ANXA2, ANXA4, and ANXA5), neutrophil defensin (DEFA1), interleukin enhancer-binding factors (ILF2 and ILF3), IL27, ITBG1, and MRC1 (FIG. 2B). Angiogenesis related basement membrane (BM) proteins were also detected using LC-MS/MS, including laminin (LAMA2, LAMA4, LAMA5, LAMB1, LAMB2, LAMB3, and LAMC1), fibronectin (FN1), heparin sulfate (HSPG2) and type-4 collagen (COL4A1, COL4A2, and COL4A3) (FIG. 2C), each of which has been shown to play key roles in angiogenesis.[17-20]

Endothelial Cell Gene Expression within hPE-Induced Angiogenic Networks

Figure 2D:
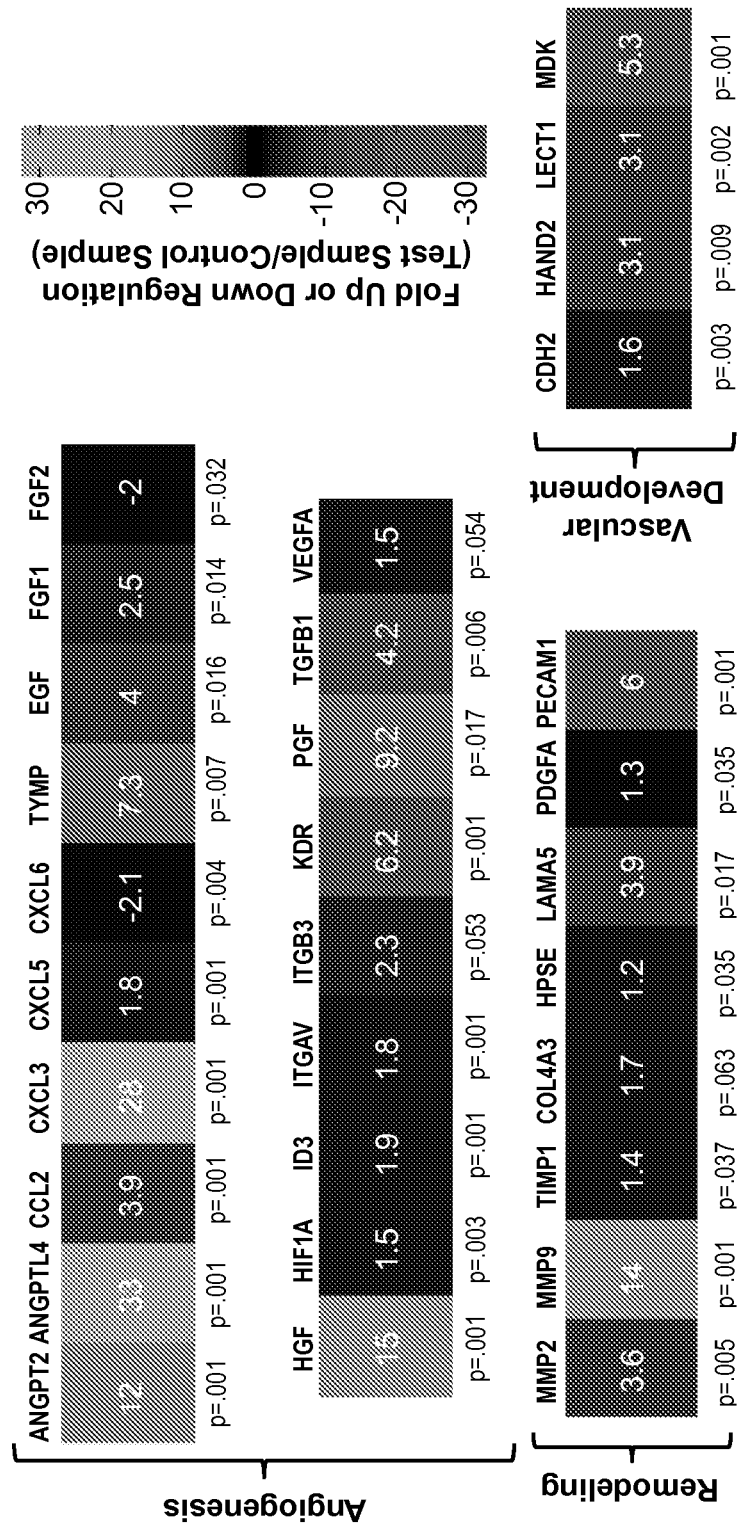
FIG. 2D illustrates genetic analysis performed on HUVECS seeded for 3 days onto 100 μL PE/cm$^2$ at a density of 80,000 cells/cm$^2$. Some angiogenesis related proteins not present in the lysate, including VEGFA, were upregulated by HUVECs when seeded onto hPE. Data are representative of four biological replicates. P-values are calculated using a Student's t-test of the replicate 2^(-Delta Ct) values for each gene in the control group and treatment groups.

In conjunction with chemokine analysis, HUVEC gene analysis further affirmed the angiogenic nature of placenta extract. RT-PCR analysis showed that endothelial cells seeded on hPE for 3 d expressed a wide range of essential pro-angiogenic genes including hepatocyte growth factor, epidermal growth factor, and placental growth factor (FIG. 2D). Additional upregulated genes include MMP2 and MMP9, which are proteolytic enzymes that aid in the degradation of the surrounding extracellular matrix in order to facilitate the migration of the endothelial cells as well as other cells associated with ECM remodeling[21]. Type IV collagen was also upregulated, which is associated with the formation of basement membranes in maturing microvessel systems[22].

Modulation of Capillary Development and Morphology In Vitro

Figure 3C:

Historically, in vitro assays have little or no control over the rate and stage of angiogenesis.[9] The present data shows in vitro hPE-based angiogenesis assays can be modulated to control the maturation and morphology of angiogenic network formation by varying the initial cell seeding density. After 1 day, HUVECs seeded at density of 40,000 cells/cm$^2$ formed more defined tubules by comparison to seeding at a density of 80,000 cells/cm$^2$, but by day 5, cells seeded at both densities had well defined tubules (FIG. 3A). These results show that the maturation stage of network formation can be controlled when cultures are exposed to hPE by varying the cell seeding density. For example, Quantitative image analysis of the capillary networks (mean tubule length [mm], tubule density [#/mm$^2$], branch points [#/mm$^2$], meshes [#/mm$^2$], and mean tubule width [mm]) (FIG. 3C) showed that higher seeding densities resulted in a slower network maturation (an extended time frame to reach the highest mean tubule length and number of meshes/mm2), allowing a more detailed analysis as the time frame of network formation can be extended. Comparatively, lower cell densities resulted in a faster maturation rate that would be more conducive to rapid screening approaches to (for example) test the effectiveness of angiogenesis blockers for cancer therapies.

Figure 3D:
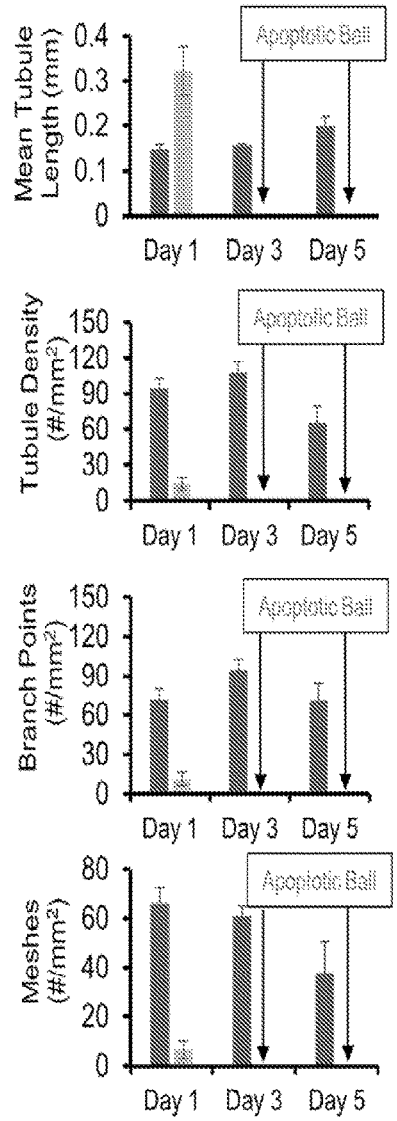

As the historical gold standard for in vitro angiogenesis assays, Matrigel-induced angiogenic networks were compared to hPE-induced networks (FIG. 3D). Morphologies of endothelial cell capillary networks were first analyzed by exposing cell cultures to either Matrigel or hPE using Calcein AM to determine viability and network structure. One day post seeding, Matrigel coated plates had shown HUVEC to form defined angiogenic tubule networks, but after 3 d network structures collapsed into spherical balls of apoptotic cells (FIG. 3A, 3D). While some cell death was noted in hPE induced networks no apoptotic ball formations were observed after an extended 5 d period.

During the late stages of angiogenesis ECs recruit smooth muscle cells (SMC) to stabilize vessels as capillary networks mature. As such, the effect of hPE and Matrigel on smooth muscle cell morphology was assessed. Interestingly, in the absence of HUVEC, SMC seeded onto Matrigel formed tubules after 1 d (FIG. 3B.i), but on hPE coated plates maintained typical 'hill and valley' formations (FIG. 3B.ii), indicating significant differences in molecular signaling pathways between cell types. SMC are not known to form tubules in the initial stages of microvessel formation, thus these results may indicate hPE-based angiogenesis more accurately represents normal physiology.

Analysis of hPE-Induced Angiogenesis for Drug Screening Applications

In addition to its role in regenerative medicine, angiogenesis driven by the human placental extract (hPE) was tested for its ability to screen angiogenesis related drugs in vitro. Matrigel was used as control. Matrigel and hPE-based angiogenesis assays were screened against thrombospondin-1(TSP-1), a glycoprotein with potent inhibition activity on neovascularization. TSP-1 represents a model drug for the anti-angiogenic treatment of solid tumors[23]. After 1 d of culture, control HUVECs seeded directly onto tissue culture plates were not affected by TSP-1, with cells forming typical cobblestone morphologies. By contrast, HUVECs cultured on hPE treated culture plates had significantly reduced angiogenic network formation. (FIG. 4A). Results show the total tubule-length and branch points to decrease linearly as a function of TSP-1 concentration (FIG. 4B). Importantly, these studies indicate hPE-based assays to be more sensitive to drug concentration as compared to Matrigel-based assays. This is shown by the higher correlation between TSP-1 concentration and percent reduction in angiogenic network area of coverage, with $R^2$ values of 0.97 and 0.36, respectively (FIG. 4C). The inhibition of network formation is further validation of actual vessel formation rather than an unknown stress response. Additionally, because the hPE is human derived, it avoids inter-species based inaccuracies that may result from screening with non-human systems[13,14].

In Vitro Angiogenic Networks Formation within a 3D Bioscaffold

Figure 5A:
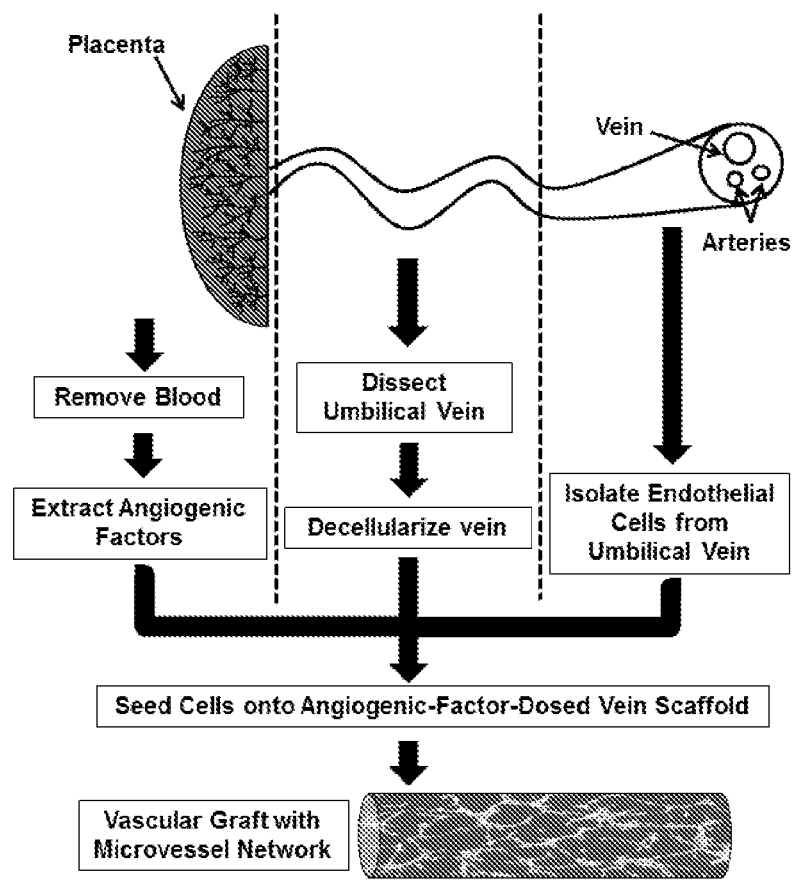
FIGS. 5A-5C illustrate in vitro angiogenesis on 3D tissue constructs.
Figure 5B:
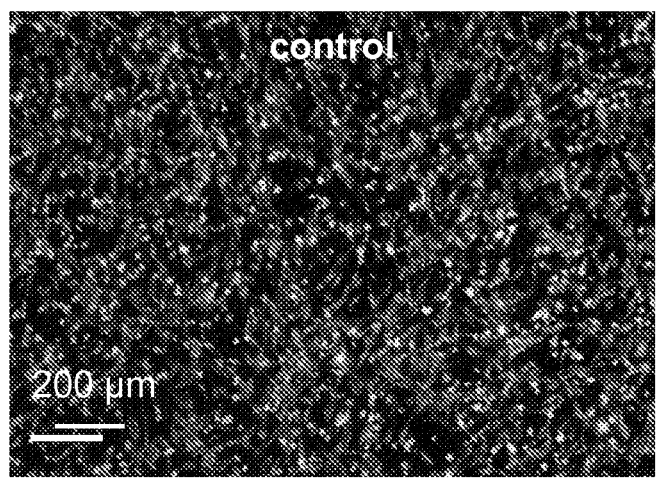

Successful vascularization of engineered organs has been a major roadblock to developing successful regenerative medicine therapies[24], the potential of hPE to induce angiogenesis in an ex vivo derived bioscaffold was analyzed. These studies show that hPE induced the formation of angiogenic networks in engineered (decellularized) human umbilical vein (HUV) bioscaffolds (FIG. 5A). Consistent with assays in 2D culture plates, endothelial cells (ECs) seeded onto the bioscaffolds developed elongated morphologies that were connected into multi-cellular cords, forming complex interconnected networks.

Figure 5C:
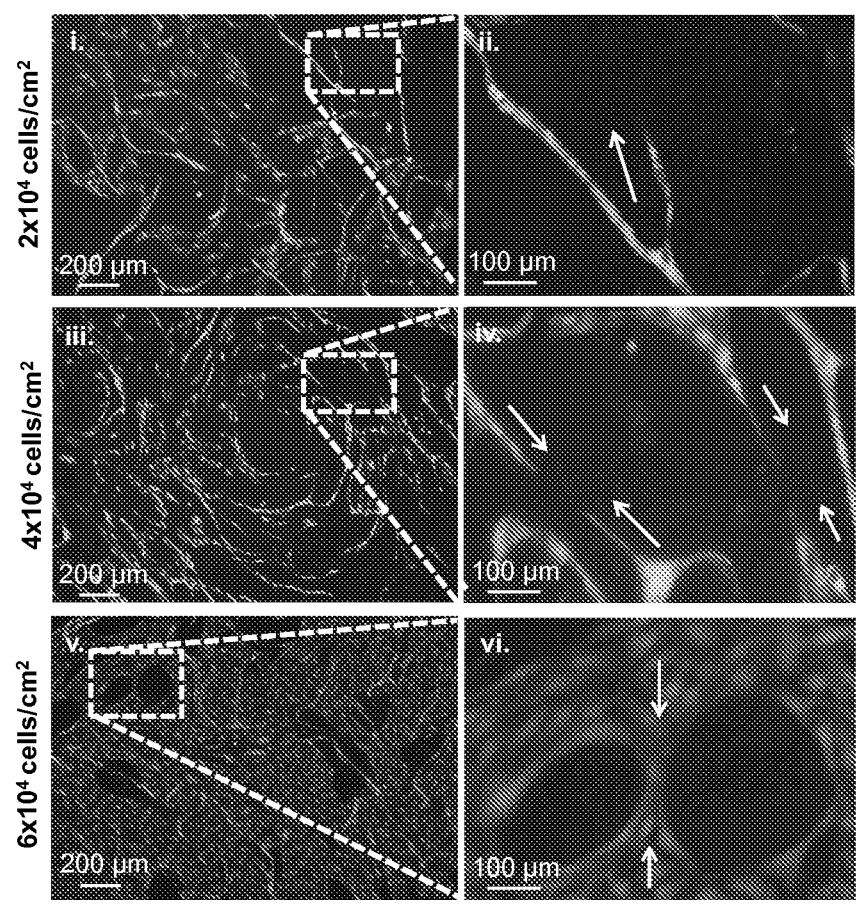

In vivo angiogenesis occurs by a variety of mechanisms, most commonly sprouting or intussusception. These data show sprouting versus intussusceptive angiogenesis can be modulated in vitro by varying cell density when incubated with hPE. At lower cell densities ($2 \times 10^4$ cells/cm$^2$) network morphologies on the hPE-incubated scaffolds exhibited sprouting angiogenesis (FIG. 5C.i, 5C.ii), at intermediate densities ($4 \times 10^4$ cells/cm$^2$) network morphologies exhibited a combination of sprouting and intussusceptive angiogenesis (FIG. 5C.iii, 5C.iv), and at higher densities ($6 \times 10^4$ cells/cm$^2$) network morphology more closely resembled intussusceptive angiogenesis (FIG. 5C.v, 5C.vi). The correlation between cell density and the specific mechanism of angiogenesis supports the current understanding of in vivo capillary and network formation, as sprouting generally occurs during early phases of angiogenesis in low cell density regions devoid of capillaries. By contrast, intussusception occurs in higher cell density regions where capillaries and endothelial cells already exist[25,26].

Induction of Angiogenesis In Vivo

Figure 6B:
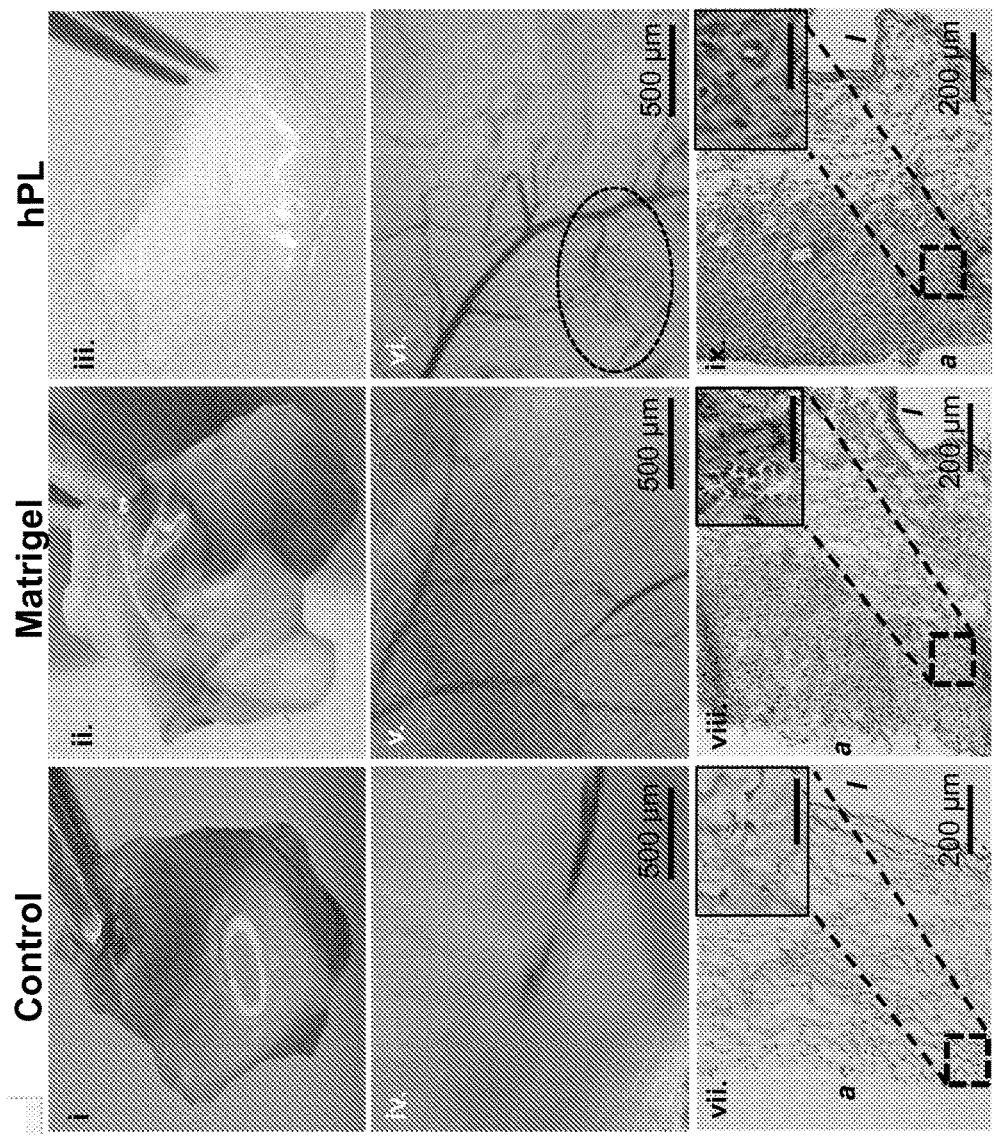
FIGS. 6A-6B represent illustrations of in vivo angiogenesis in hPE-incubated bioscaffolds.
Figure 6A:
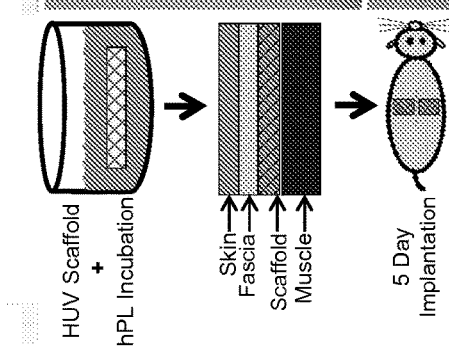

Using a subcutaneous rat model (FIG. 6A) the angiogenic response to dosed scaffolds (Matrigel and hPE) was assessed 5 days post implantation. Both control and Matrigel-incubated scaffolds displayed significant fibrosis surrounding the scaffold, whereas hPE dosed scaffolds exhibited no discernible fibrosis around the implant (FIG. 6B.i-6B.iii.). Fibrosis prevention in hPE samples is believed to result from immune related molecules, as detected with LC-MS/MS, including, but not limited to, anti-inflammatory Annexins (ANXA1, ANXA2, ANXA4, and ANXA5)[27], antimicrobial defensin peptides such as DEFA1[28], and MRC1, which is known to bind to potential pathogens including viruses and bacteria.

As shown by brightfield microscopy both Matrigel and hPE-incubated scaffolds displayed a significant increase in neovascularization compared to controls (FIG. 6B.iv-6B.vi.). While the total vascularization appeared similar, hPE treatments show the formation of maturing capillary beds, whereas Matrigel samples appeared less structured, without evidence of mature capillary bed formation. H&E stained sections show that cells had migrated into and throughout scaffolds incubated in hPE, whereas Matrigel incubated samples had reduced cellular infiltration, and cells within the control samples were limited to the scaffold periphery (FIG. 6B.vii.-6B.ix.). The improved cell migration in both Matrigel and hPE-incubated samples was the result of chemotactic and growth factor signals adsorbed to the scaffold structure. Despite improved cell migration with both hPE and Matrigel dosed scaffolds over controls, cellular remodeling between the sample groups displayed variation. Cell dense regions in the Matrigel-incubated samples displayed remnants of the original HUV fibers, with the general structure qualitatively more amorphous in comparison to hPE-incubated scaffolds that appeared to be almost completely remodeled, displaying a more organized fiber and cellular structure (FIG. 6B.vii.-6B.ix.).

Discussion

Tissue regeneration, infarct tissue and ischemic wound repair are three clinical areas where an improved strategy for wound recovery or organ replacement would have significant clinical impact. The use of amniotic and chorionic membranes in a variety of applications has grown significantly over the last 5 years, with an increasing body of evidence indicating perinatal tissues hold considerable clinical promise[29-32].

Results herein detail a novel approach to concentrate and deliver physiological ratios of a potent human derived stimulator of angiogenesis and tissue remodeling. These data show enhanced cellular activity toward initiating capillary formation (in vitro and in vivo), controlling EC phenotype during angiogenesis with a capacity to modulate growth or maturation dynamics, and a significant reduction in in vivo tissue fibrosis.

The capacity to modulate the in vitro maturation rate of capillary network formation and to control the occurrence of sprouting and intussusceptive angiogenic network morphologies may provide a useful platform to further the understanding of regulatory pathways during wound healing and organ regeneration. Based on comparisons with Matrigel, the mechanism with which hPE stimulates cells appears to be fundamentally different. SMC incubated with Matrigel initiated capillary-like formations whereas SMC exposed to the hPE retained their typical hill and valley morphology, as such the human derived hPE may provide a more representative model of physiological angiogenesis in more complex models.

A number of current methods are based on human-derived (recombinant) modulators that rely on single or discrete combinations of angiogenesis modulators[33]. While discrete combinations are useful to control variation and reduce the inherent complexity of multifarious approaches, they constrain the screening process and fail to represent the broad set of human in vivo molecular interactions that are likely to be critical when testing the potential of anti-angiogenic, tumor suppressive drugs.

The inherent complexity of hPE based models may lead to advances in the pharmaceutical industry by providing a more effective screening approach for tumor suppressive drugs. Relative to current techniques, exposure of human EC to hPE was shown to have increased sensitivity to angiogenesis inhibiting drug-concentrations (TSP-1) with lower detection limits.

hPE-based models induce angiogenesis using a broad set of human-derived molecules at near physiological ratios. It is believed that regulation of only selected molecular pathways will confine attempts to discover novel anti-angiogenesis drugs as vessel formation in vivo requires the induction of multiple metabolic pathways[34,35]. As such, a drug may modulate angiogenesis via interaction with any of these numerous pathways but may have little effect inducing competent angiogenesis when the complexity of the local environment is lacking. Results from the in vivo analysis in the present example provide further evidence that the complex PE influences numerous biochemical pathways, resulting in a broad range of effects. Data shows hPE not only displayed enhanced angiogenic properties, but was also shown to have immune reductive properties, as illustrated by reduced fibrosis within hPE dosed bioscaffolds. Given complex interconnections between angiogenesis and immunological molecular pathways[36], the molecular composition of hPE provides a suitable basis for the development of clinically applicable techniques to induce capillary formation without significant immunological and inflammatory reactions.

It appears that the positive outcomes of the above-described studies are not only related to the presence of key growth factors (GF) and gene regulators in the PE, but also their presence in physiological ratios. For example, while VEGF was upregulated in hPE-induced EC, the hPE solution contained no detectable levels. This contrasts with Matrigel (BMM) that contains active concentrations of VEGF in both the standard and GFR (growth factor reduced) version. With results herein showing more mature capillary bed formations, the presence of VEGF is only one of many contributing factors, and the presence of other regulators likely plays a key role in vascular development. Similarly, with comparison to human recombinant proteins used to initiate angiogenesis, these rely on highly concentrated (typically) single GF[37-39]. Problems have been reported with single, highly reactive GF applied clinically resulting in undesirable effects[40-42].

The hPE angiogenesis model has been validated in 2D and 3D in vitro models, as well as in vivo within bioengineered tissue implants and can be readily adapted to a variety of clinical or pharmaceutical applications. Its derivation from physiologically healthy, human vascular beds combined with its angiogenic and immune reductive properties make it unique among current angiogenesis models. The data presented here have shown hPE to play a pivotal role in a number of key clinical issues where demand for alternative, more successful, approaches are a clinical priority.

References for Example 1

1. Thurston, G., Murphy, T. J., Baluk, P., Lindsey, J. R. & McDonald, D. M. Angiogenesis in mice with chronic airway inflammation: strain-dependent differences. *Am J Pathol* 153, 1099-1112 (1998).

2. Cristofanilli, M., Charnsangavej, C. & Hortobagyi, G. N. Angiogenesis modulation in cancer research: novel clinical approaches. *Nature reviews. Drug discovery* 1, 415-426 (2002).
3. Lokmic, Z. & Mitchell, G. M. Engineering the microcirculation. *Tissue Eng Part B Rev* 14, 87-103 (2008).
4. Kurz, H., Burri, P. H. & Djonov, V. G. Angiogenesis and vascular remodeling by intussusception: from form to function. *News in physiological sciences: an international journal of physiology produced jointly by the International Union of Physiological Sciences and the American Physiological Society* 18, 65-70 (2003).
5. Burri, P. H. & Djonov, V. Intussusceptive angiogenesis—the alternative to capillary sprouting. *Molecular aspects of medicine* 23, S1-27 (2002).
6. Risau, W. Mechanisms of angiogenesis. *Nature* 386, 671-674 (1997).
7. Folkman, J. Angiogenesis in cancer, vascular, rheumatoid and other disease. *Nature medicine* 1, 27-31 (1995).
8. Jain, R. K., Schlenger, K., Hockel, M. & Yuan, F. Quantitative angiogenesis assays: progress and problems. *Nature medicine* 3, 1203-1208 (1997).
9. Auerbach, R., Akhtar, N., Lewis, R. L. & Shinners, B. L. Angiogenesis assays: problems and pitfalls. *Cancer metastasis reviews* 19, 167-172 (2000).
10. Auerbach, R., Lewis, R., Shinners, B., Kubai, L. & Akhtar, N. Angiogenesis assays: a critical overview. *Clinical chemistry* 49, 32-40 (2003).
11. Kleinman, H. K. & Martin, G. R. Matrigel: basement membrane matrix with biological activity. *Seminars in cancer biology* 15, 378-386 (2005).
12. Cockerill, G. W., Gamble, J. R. & Vadas, M. A. Angiogenesis: models and modulators. *International review of cytology* 159, 113-160 (1995).
13. Warren, M. S. et al. Comparative gene expression profiles of ABC transporters in brain microvessel endothelial cells and brain in five species including human. *Pharmacological Research* 59, 404-413 (2009).
14. Febbraio, M., Hajjar, D. P. & Silverstein, R. L. CD36: a class B scavenger receptor involved in angiogenesis, atherosclerosis, inflammation, and lipid metabolism. *Journal of Clinical Investigation* 108, 785-791 (2001).
15. Wang, Y. & Zhao, S. in Vascular Biology of the Placenta (San Rafael (Calif.); 2010).
16. Fett, J. W. et al. Isolation and characterization of angiogenin, an angiogenic protein from human carcinoma cells. *Biochemistry* 24, 5480-5486 (1985).
17. Xu, J. et al. Proteolytic exposure of a cryptic site within collagen type IV is required for angiogenesis and tumor growth in vivo. *The Journal of cell biology* 154, 1069-1080 (2001).
18. Kim, S., Bell, K., Mousa, S. A. & Varner, J. A. Regulation of Angiogenesis<i> in Vivo</i> by Ligation of Integrin α5β1 with the Central Cell-Binding Domain of Fibronectin. *The American journal of pathology* 156, 1345-1362 (2000).
19. Iozzo, R. V. & San Antonio, J. D. Heparan sulfate proteoglycans: heavy hitters in the angiogenesis arena. *Journal of Clinical Investigation* 108, 349-355 (2001).
20. Patarroyo, M., Tryggvason, K. & Virtanen, I. in Seminars in cancer biology, Vol. 12 197-207 (Elsevier, 2002).
21. Rundhaug, J. E. Matrix metalloproteinases and angiogenesis. *J Cell Mol Med* 9, 267-285 (2005).
22. Kalluri, R. Basement membranes: structure, assembly and role in tumour angiogenesis. *Nature reviews. Cancer* 3, 422-433 (2003).
23. Lawler, J. Thrombospondin-1 as an endogenous inhibitor of angiogenesis and tumor growth. *J Cell Mol Med* 6, 1-12 (2002).
24. Laschke, M. W. et al. Angiogenesis in tissue engineering: breathing life into constructed tissue substitutes. *Tissue engineering* 12, 2093-2104 (2006).
25. Adair, T. in Integrated systems physiology, from molecule to function to disease (Morgan & Claypool, 2011).
26. Djonov, V., Baum, O. & Burri, P. H. Vascular remodeling by intussusceptive angiogenesis. *Cell and tissue research* 314, 107-117 (2003).
27. Perretti, M. et al. Endogenous lipid- and peptide-derived anti-inflammatory pathways generated with glucocorticoid and aspirin treatment activate the lipoxin A4 receptor. *Nature medicine* 8, 1296-1302 (2002).
28. Paslakis, G. et al. The Putative Role of Human Peritoneal Adipocytes in the Fight against Bacteria: Synthesis of the Antimicrobial Active Peptide DEFA1-3. *Nephron Experimental Nephrology* 115, e96-e100 (2010).
29. Lee, S.-H. & Tseng, S. Amniotic membrane transplantation for persistent epithelial defects with ulceration. *American journal of ophthalmology* 123, 303-312 (1997).
30. Jin, C. Z. et al. Human amniotic membrane as a delivery matrix for articular cartilage repair. *Tissue engineering* 13, 693-702 (2007).
31. Bose, B. Burn wound dressing with human amniotic membrane. *Annals of the Royal College of Surgeons of England* 61, 444 (1979).
32. Daniel, J., Abe, K. & McFetridge, P. S. Development of the human umbilical vein scaffold for cardiovascular tissue engineering applications. *ASAIO J* 51, 252-261 (2005).
33. Vailhe, B., Vittet, D. & Feige, J. J. In vitro models of vasculogenesis and angiogenesis. *Laboratory investigation; a journal of technical methods and pathology* 81, 439-452 (2001).
34. Pepper, M., Ferrara, N., Orci, L. & Montesano, R. Potent synergism between vascular endothelial growth factor and basic fibroblast growth factor in the induction of angiogenesis in vitro. *Biochemical and biophysical research communications* 189, 824-831 (1992).
35. Sullivan, D. C. & Bicknell, R. New molecular pathways in angiogenesis. *British journal of cancer* 89, 228-231 (2003).
36. O'Byrne, K. J., Dalgleish, A., Browning, M., Steward, W. & Harris, A. The relationship between angiogenesis and the immune response in carcinogenesis and the progression of malignant disease. *European journal of cancer* 36, 151-169 (2000).
37. Montesano, R., Vassalli, J.-D., Baird, A., Guillemin, R. & Orci, L. Basic fibroblast growth factor induces angiogenesis in vitro. *Proceedings of the National Academy of Sciences* 83, 7297-7301 (1986).
38. Ferrara, N. & Alitalo, K. Clinical applications of angiogenic growth factors and their inhibitors. *Nature medicine* 5 (1999).
39. Zisch, A. H., Lutolf, M. P. & Hubbell, J. A. Biopolymeric delivery matrices for angiogenic growth factors. *Cardiovascular Pathology* 12, 295-310 (2003).
40. Epstein, S. E., Fuchs, S., Zhou, Y. F., Baffour, R. & Kornowski, R. Therapeutic interventions for enhancing collateral development by administration of growth factors: basic principles, early results and potential hazards. *Cardiovascular Research* 49, 532-542 (2001).
41. Lee, R. J. et al. VEGF gene delivery to myocardium deleterious effects of unregulated expression. *Circulation* 102, 898-901 (2000).

42. Hariawala, M. D. et al. VEGF improves myocardial blood flow but produces EDRF-mediated hypotension in porcine hearts. *Journal of Surgical Research* 63, 77-82 (1996).

Example 2

Controlled Delivery of Placental Extract for Stimulation of Angiogenesis
Introduction Tissue engineering aims to build tissues and organs from scratch in vitro in order to transplant them into ill patients. However, this revolutionary alternative to transplantation is subordinated to the lack of the formation of a suitable vasculature for the supply of oxygen and nutrients to cells seeded in the transplanted graft. Accordingly, an effective method to induce angiogenesis in tissue-engineered constructs is urgently needed.

To date, all the methods tried to promote vascularization in the engineered products have had unsatisfactory results. The present disclosure provides a protocol to derive a pro-angiogenic extract from the human placenta, which was shown, as described in the example above, to induce and modulate the initial stages of angiogenesis.

The present example describes a 3D in vitro angiogenesis assay to promote the formation of a capillary network and to sustain it over time. To this purpose, the angiogenic potential of the placental extract and its bioactivity over time has been analyzed. These investigations have shown that a frequent administration of the extract promotes the formation of a mature and long lasting capillary network. Therefore, biodegradable gelatin microparticles for incorporation and controlled release of the extract were prepared and their degradation kinetics were studied. Finally, a 3D in vitro angiogenesis assay was developed. Placental extract loaded microparticles were embedded in a Collagen Type I hydrogel scaffold seeded with HUVECs, and evidence of initial phase of microvessel formation within the matrix was demonstrated.

The loss or failure of an organ or a tissue is one of the most severe and expensive human health problems in contemporary society. Many approaches to solve this problem have been attempted including surgical reconstruction, drug therapy, synthetic prostheses, mechanical devices, and transplantation. In the long term, these approaches commonly fail because they do not completely replace the functionality of the lost organ or tissue[2], or in the case of transplantation the demand for organs is large and the number of donors is insufficient.

One solution would be to develop engineered organ or tissue. However, current tissue engineering approaches have seen limited success due in part to nutrient barriers that occur across thick bioscaffolds. A large obstacle to engineering thick (>200 µm) tissue constructs is that oxygen diffusion is typically limited to a distance of 150 to 200 µm in tissue engineered scaffolds thus impairing cell growth and viability within 3D tissue constructs[6,7]. Oxygen is a critical nutrient for cell survival, and without it, cells within a scaffold die. Moreover, poor transport conditions often result in the formation of a fibrotic capsule, secreted by cells. The formation of this capsule results in the lack of nutrient mass transfer within the scaffold and ultimately leads to a low cell density. Thus, engineering tissues capable of long term sustainability would benefit from methods to facilitate the delivery of oxygen and nutrients to cells seeded in 3D tissue constructs. The placental extract and methods the present disclosure provide an approach to overcome oxygen and nutrient deficiencies that involves inducing the rapid development of a nutrient rich capillary system within the scaffold. Implementing methods to supply these essential nutrients not only to the margins of the construct, but also in the center, would help to prevent the formation of the fibrotic capsule.

Angiogenesis is central to tissue development and maintenance and its successful modulation promotes the controlled formation of an established vascular network in implanted grafts. Several biological factors and molecular pathways are involved in the regulation of this complex process which is still partially unknown. To better understand the molecular mechanisms which initiate and control vascular growth, research has focused on the development of angiogenesis assays that are cell culture systems which reproduce in vitro or in vivo the definitive elements of angiogenesis under simplified, defined and controlled conditions. A variety of different approaches have been used to promote in vitro angiogenesis but to date there has been little success in translating them to the clinical practice. A limitation of most angiogenesis models is that they are either animal-derived (e.g. Matrigel based) or entirely dependent on the use of live animals (e.g. the chick chorioallantoic membrane and the rabbit corneal micropocket). Moreover, they lack the variety of cytokines and chemical gradients that are native in vivo. As a consequence, the result of these assays has often been disappointing because of the lack of a long-lasting vessel formation. Thus, a robust in vitro model of human origin would be useful for mechanistic studies and screening angiogenesis drugs for humans.

Given that the placenta is a readily available tissue and a rich source of vascular tissue and angiogenesis related growth factors, in these studies it used it to derive a multi-protein human placental extract or matrix (hPE or hPM), a viscous protein compound, rich in cytokines and angiogenesis related growth factors, that promotes angiogenesis, as previously described above and in Example 1. It has been shown that hPE can induce and modulate the initial stages of angiogenesis in vitro for a limited period of time. Additionally, hPE has also been shown to significantly reduce fibrosis.

The present example provides a method for the sustained delivery of hPE so that growth factors within it remain functional long enough to enable the formation of mature capillary networks. To this purpose, microparticles were developed as delivery system due to their versatility and to their ability to efficiently encapsulate polypeptides and release them at a continuous rate for a long period of time[22].

Microparticles are solid, approximately spherical particles with a size ranging from 1 to 1000 µm and with a large surface-to-volume ratio[23]. They can be prepared with several different substances, both natural (e.g. starches, gums) and synthetic (e.g., polylactic and polyglycolic acid) and using different techniques such as hot melt extrusion, spry drying or solvent removal[24]. The release rate of microparticles can be modulated by changing their size: smaller particles dissolve more quickly than large ones due to their increased surface-to-volume ratio. For this reason, it is possible to modulate the delivery rate by combining particles of different sizes[25]. Drug or protein release from microparticles usually occurs by simple matrix bioerosion. This process involves the erosion of the particle surface which is then followed by bulk erosion and entrance of the releasing medium in the particles pores[28,27].

In this example, biodegradable gelatin microparticles were prepared and used to performed a 3D in vitro angiogenesis assay. Angiogenesis assays are cell culture systems that reproduce in vitro or in vivo the definitive elements of angiogenesis under simplified, defined and controlled conditions[28]. They can be two-dimensional or three-dimensional. In 3D in vitro assays, ECs develop tubular structures both on the surface of the substrate and that invade the surrounding matrix, usually constituted by a biogel[13].

The present example provides an embodiment of a 3D in vitro angiogenesis assay to promote the formation of a long lasting vascular network within an implanted graft. In this embodiment, the assay is prepared by embedding Human Umbilical Vein Endothelial Cells (HUVECs) together with PE-loaded microparticles in a collagen type I matrix. The angiogenic response of HUVECs at different incubation times was then analyzed.

Experimental Methods

Endothelial Cell Isolation and Culture.

Human Umbilical Vein Endothelial Cells (HUVECs), pre-isolated from human umbilical vein and pre-cultured as described by Jaffe et al. (Culture of Human Endothelial Cells Derived from Umbilical Veins. 52, 2745-2756; 1973, incorporated by reference herein with respect to isolation and culturing of HUVECS) were detached from the flask using acutase (Fisher Scientific) and centrifuged at 1000 rpm for 5 minutes. The cell pellet was resuspended in Media (25 ml of glutamine, 0.5 ml of hydrocortisone, 0.5 ml of ascorbic acid, 10 ml of FBS, 1.25 µL of VEGF, and 1.25 µL of bFGF added in 500 ml of VascuLife Basal Media) and HUVECs were counted using a hemocytometer.

Analysis of the hPM Angiogenicity as a Function of Time.

To assess how hPE incubation time influenced HUVECs angiogenic response, cells were plated on hPE coated tissue culture plates and incubated with hPE for 1 day, 3 days or 5 days. Briefly, placental matrix was prepared using an isolation methods described in the example above. A vial containing the extract was thawed and pipetted (100 µL per cm$^2$) in the wells of a 96 well plate. HUVECS were prepared for plating by direct pipetting of the cell solution at 20,000 cells/cm$^2$. Angiogenic Media was added to each prepared sample of the plate (200 µL per cm$^2$) and this latter was placed in a humidified 5% $CO_2$ incubator at 37° C.

To determine how hPE retains bioactivity overtime, it was stored (in an incubator at 5% $CO_2$ and 37° C.) for varying amounts of time including 20 days, 15 days, 9 days, 7 days, 5 days, 3 days and 1 day. Then, a film hPE from each time point was coated onto a tissue culture 96 well plate and seeded with HUVECs as described above. Cells were cultured for 3 days, and angiogenic networks were qualitatively characterized.

Analysis of the hPE Angiogenicity as a Function of Number of Inoculations.

The response of HUVECs to the number of hPE inoculations was also analyzed. Cells initially were seeded onto hPE films at day 1, and hPE was mixed with culture media for hPE doses after day 1. Cells were cultured for 5 days, with some sample groups receiving only one inoculation of hPE on day 1 (day of seeding), others two inoculations on day 1 and 3 and others three inoculations on day 1, 3, and 4.

Preparation of Gelatin Microparticles.

Gelatin microparticles were prepared using the method described by Tabata, et al. (incorporated by reference herein with respect to the preparation of gelatin microparticles)[33]. All the reagents used were obtained from Fisher Scientific. Briefly, a 10% wt aqueous solution of Type B gelatin was prepared by adding 1 g of gelatin to 9 mL of deionized water. Temperature was increased to 45° C. and the solution was added dropwise via a syringe and a 21-G needle to 375 ml of warm (45° C.) olive oil under constant stirring at 400 rpm. After 10 min the emulsion temperature was decreased to 15° C. and stirring was maintained for 30 min to induce gelation. 100 mL of chilled acetone were added and the emulsion was stirred for 1 hour. Microparticles were removed by vacuum filtration, washed with acetone and dried. Once dried, they were placed in an aqueous solution containing 0.1% wt of Tween 80 and 0.5% wt of gluteraldehyde. The solution was constantly stirred at 125 rpm at 4° C. for 15 hours to facilitate the crosslinking of the microparticles. Crosslinked microparticles were collected by vacuum filtration, washed in deionized water and then agitated in 100 mL of 10-mM glycine aqueous solution to block any unreacted glutaraldehyde. After 1 hour, microparticles were again collected by filtration, washed in deionized water and freeze-dried. Cross-linked freeze-dried gelatin microparticles were loaded by incubating 100 µL of pure hPM per mg of microparticles. The mixture was vortex at maximum speed and incubated overnight at 4° C. to allow adsorption to occur.

In Vitro Release Kinetics from hPE Loaded Microparticles.

To assess the degradation kinetics of gelatin microparticles, 10 mg (dry weight) of uncrosslinked blank microparticles were incubated in 1 ml of Phosphate Buffer Saline (PBS) with a pH of 7.4 at 37° C., and protein release kinetics were compared to release from hPE-loaded-crosslinked and unloaded-crosslinked microparticles using a protein assay kit. Briefly, the supernatant of each specimen was periodically collected (after 1, 2, 3 and 6 hours and then daily) and replaced fresh PBS. Protein in the supernatant was quantified using the Micro BCA Assay Kit (Thermo Scientific, Waltham, Mass., USA) with absorbance measured at 562 nm with a plate reader (Bio Teck Sinergy 2 plate reader, Bio Teck Instrument, Inc., Winooski, Vt.; USA). Protein concentrations were compared to freshly prepared standards of bovine serum albumin with a concentration ranging from 200 to 0.5 µg/mL. Final values are given as the total protein release from the start of the experiment and are normalized as function of uncrosslinked blank microparticles dry weight or of wet weight estimated before the beginning of the experiment. Absorbance values are normalized to values of phosphate buffered saline (pH 7.4). The linear working range of the assay was 2-40 µg/mL and the detection limit 0.1 µg/mL. Each experiment was done in triplicate.

Preparation of the 3D In Vitro Angiogenesis Assay.

A non-planar 3D in vitro angiogenesis assay was prepared using a collagen type I matrix in which HUVECs and PE-loaded microparticles were embedded. The collagen hydrogel matrix was prepared by mixing 8 mL of chilled Vitrogen Collagen, 1 mL of sterile PBS and 1.166 mL of 0.1 M NaOH solution. A transition in the color of the solution from red to purple indicated a pH change. The pH of the solution was checked with a pH paper and adjusted to 7.4 by the addition of few drops of 0.1 M NaOH or 0.1 M of HCl solution. Before gelation, 3 mL of HUVECs in solution were added at a concentration of 40,000 cell/mL and 2 mg of loaded microparticles were added, prepared as previously described[17]. Subsequently, the collagen/cell/microparticle solution was mixed by pipetting until homogeneous, and 500 µL was pipetted into each well of a 48 well plate. To induce collagen gelation, the culture plate was put in an oven at 37° C. for 30 minutes. The final thickness of the collagen hydrogels was 6.6 mm. Finally, 100 µL per cm$^2$ of angiogenic media was added to each well (containing the cell seeded, gelated, microparticle embedded hydrogels) and the plate was placed in a humidified 5% $CO_2$ incubator at 37° C.

Analytical Methods

Fluorescence Staining with Calcein AM.

Calcein AM staining was carried out using the Live-Dead Assay (Invitrogen-Life Technologies, NY, USA). Briefly, Calcein AM was pipetted directly in the media present in the culture well with a final concentration of 2 µg/ml. The dyed cells where incubated for 30 min at 37° C. and they were then observed using an inverted fluorescence microscope (Zeiss Axiovert 200 Inverted Fluorescence Microscope).

Qualitative and Quantitative Network Formation Analysis.

The analysis of the cells response to experimental conditions in in vitro models of angiogenesis has been done in previous studies in several semiquantitative and quantitative methods (each of which is incorporated by reference herein) [34-37]. Both morphological (mean tubule length) and topological (number of branching points and number of meshes) parameters have been taken in to account since they allow the characterization of the spatial organization of the ECs in the capillary-like network.

After cell staining, selected fields of view were photographed for each sample. The acquired images were analyzed using ImageJ 1.45s (Wayne, Rasband—National Institutes of Health, USA).

Figure 8:
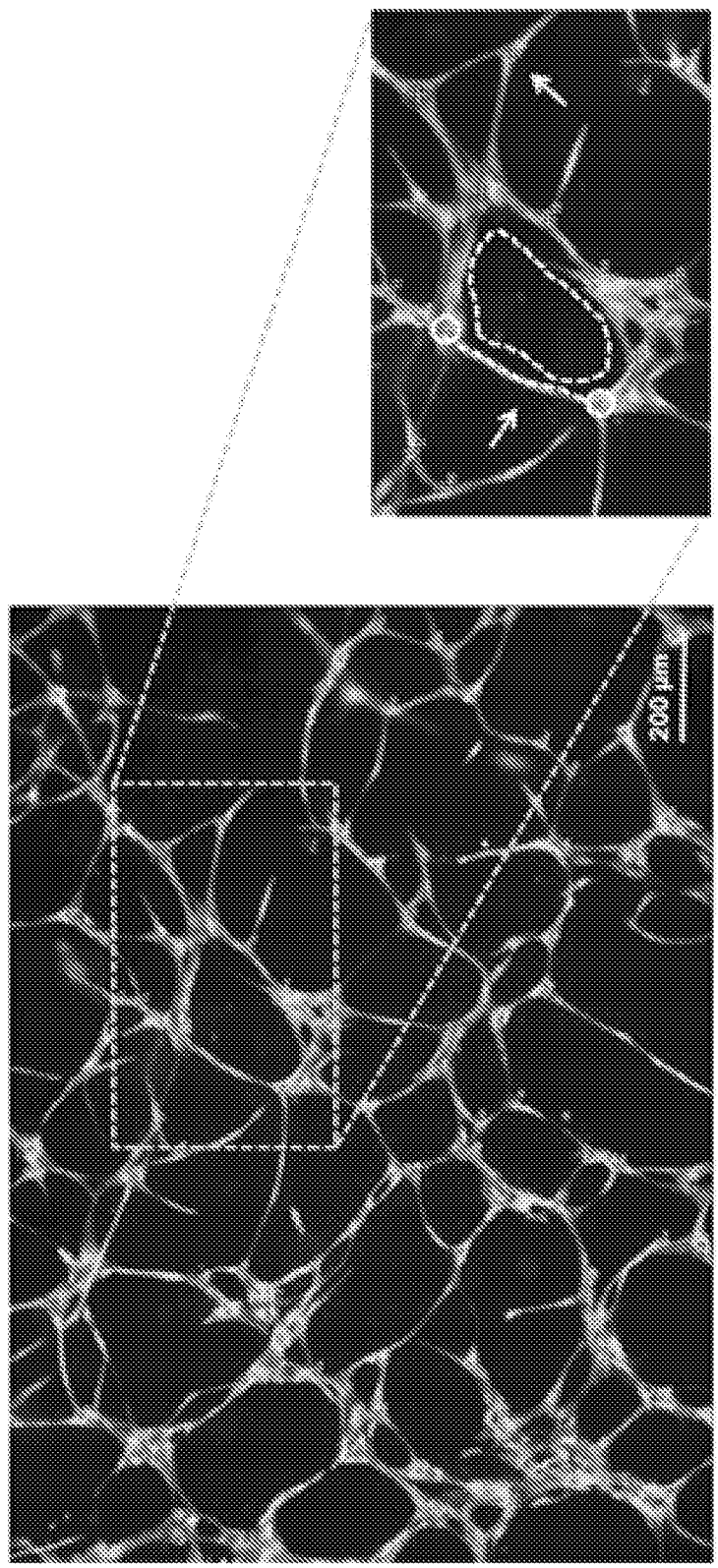
FIG. 8 illustrates an original image (on the left) and a zoom of its area (on the right) of tubes and cell network of growth on PE. The zoomed image shows how each tubule (dotted line) was identified and measured. The circlets on the right image represent the branch points, which are identified by numbered dots on the image, pointed by an arrow. Each hexagonal arrangement of the tubules identifies a mesh (dotted circle).

The branch points (BPs), which are nodes where branches meet or from where tubules sprout, were identified and counted. Also the meshes of the cell network, identified by avascular zones surrounded by hexagonally arranged vessels[38], were manually counted. Finally, tubule length was assessed by drawing a line (dotted white line in the zoomed image FIG. 8) along each tubule and the measure of that line was automatically calculated by the software.

Scanning Electron Microscopy (SEM).

Microparticles surface structure was investigated by scanning electron microscopy (S-4000 FE-SEM, Hitachi High Technologies, TX, USA). Freeze-dried samples were mounted on aluminum stubs with double sided graphite tape and coated with gold and palladium using a scatter (deskV, Denton Vacuum). Images of the samples were then taken with a Hitachi S-4000 FE-SEM (TX, USA).

Statistical Analysis.

Experiments were performed in triplicate. All graphical and tabulated data were displayed as mean±standard deviation. Data analysis was performed using SPSS (IBM, Somers, N.Y.). Significance tests were calculated using unpaired, two-tailed, Student's t-Test with unequal variance. Significance levels were set at $p<0.05$.

Results

Angiogenic Potential of PE.

The data collected show that the extent of the angiogenic response of HUVECs to PE is strongly affected by incubation time and by the number of inoculations of PE given.

Figure 9A:
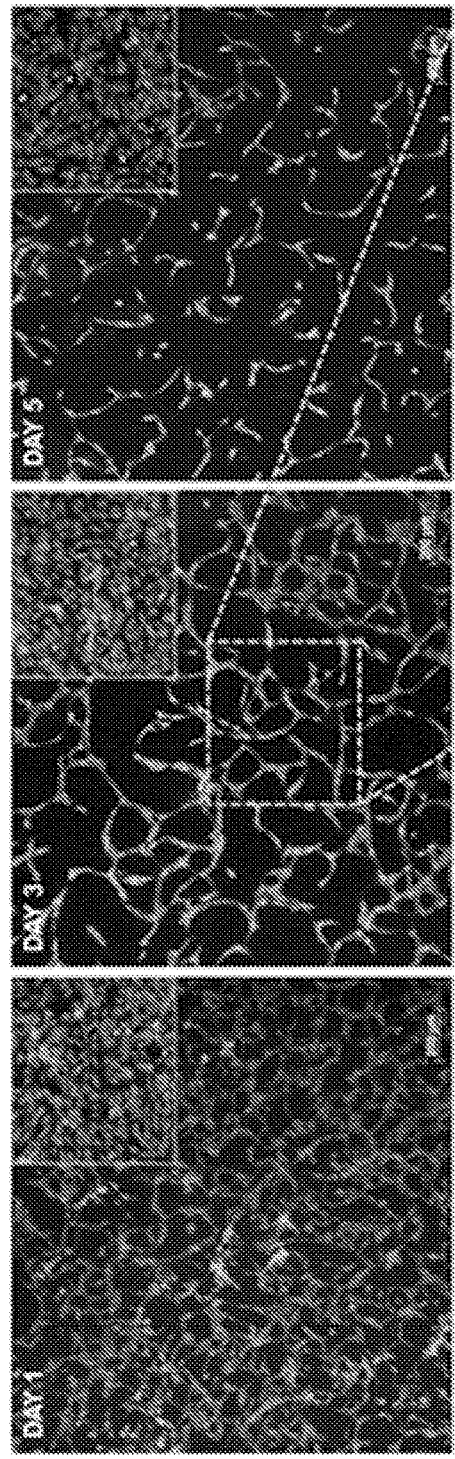
FIGS. 9A-B are a series of images (FIG. 9A) and a bar graph (FIG. 9B) illustrating the angiogenic potential of PE. The panels in FIG. 9A show cell morphologies of microvessel tubules formed by HUVECs seeded onto PE and cultured for 1, 3 and 5 days compared with HUVECS seeded onto a tissue culture plate. The capillary network started forming at day 1 and it reached a more mature configuration at day 3 (see enlargement, bottom right). On day 5 the network regressed: the number of meshes decreased, and some isolate cells (white dots) were present. The graph in FIG. 9B shows the morphological and topographic features of tubule-like network formed on PE after 1, 3 and 5 days of culture. Tubule length, number of BPs and of meshes between day 1, 3 and 5 were compared. A statistical difference (indicated with asterisks) in all three parameters was found between cells of Day 1 and of Day 5. The statistical analysis was performed with a double tailed t-test with unequal variance at p<0.05.
Figure 9B:
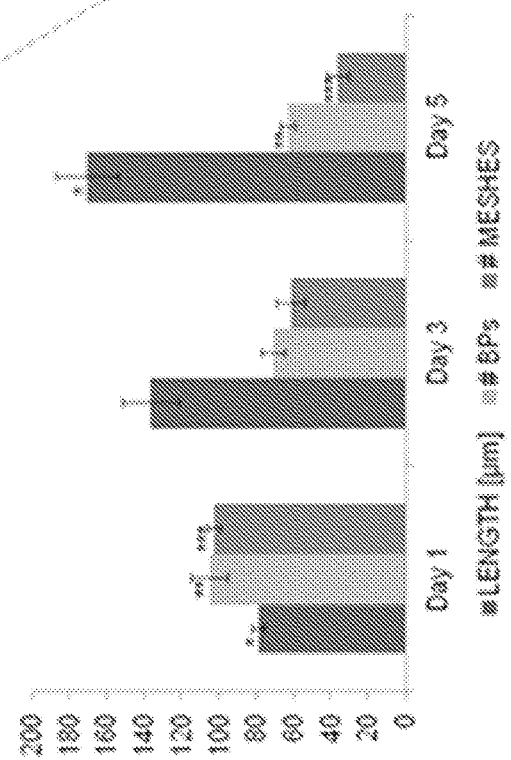

As for incubation time, HUVECs incubated with PE formed angiogenic-like networks whose morphology varied as function of incubation time (FIG. 9A-B). At day 1 after seeding, HUVECs did not yet form a defined network (FIG. 9A, DAY 1). The meshes were numerous (102.67±3.52) and small, and short tubules were observed (mean tubule length: 78.85±3.24 µm). Also, the number of branch points (BPs) was high (105±9.85) but difficult to identify in the presence of some cell clusters. A third day of culture (DAY 3 in FIG. 9A), a well formed network appeared. This is also confirmed by a lower number of BPs (71±6.25), longer tubules (mean length: 136.43±15.23 µm), and by the presence of wider and less numerous meshes (61.33±8.02). At the fifth day of culture (FIG. 9A, DAY 5), the network was still visible but it started to degrade: the tubules were longer (170.56±16.51 µm) but less numerous and thinner. Meshes were difficult to identify and their number decreased (36.33±6.02). As for the BPs, their number slightly decreased (63±4). The degradation of the network may be due to cells having already exhausted the angiogenic molecules contained in the PE. No tubule formation was observed in the control plate (top right corner in each imagine) thus indicating that the change in the cell morphology is not due to stress or other external causes.

A semi-quantitative analysis of the spatial organization of HUVECs is presented in the histogram in FIG. 9B. The bars refer to mean tubule length, number of BPs and number of meshes. It is possible to notice that a statistical difference has been found between Day 1 and Day 5 in all three parameters taken into account.

In this study capillary-like network formation was affected by the number of inoculations of PE (FIG. 10A-B). The mean tubule length increased from cells that received one inoculation to those that received three, while both the BPs and the number of meshes decreased (FIGS. 10A and 10BB). After one inoculation of PE, there was no defined network formation: the meshes were numerous (76.67±19.74) but not spread, as confirmed also by the mean tubule length (129.71±12.88 µm) (FIG. 10A, first panel). Moreover, there were several BPs (110.78±15.40) and cell clusters thus indicating that the cells were not well connected. Cells that received two inoculations formed a network but some clusters were still present (FIG. 10A, second panel). This may suggest that the network was not completely mature. However the mean tubule length increased (139.91±8.93 µm), whereas the number of meshes and the branch points decreased (52.67±19.74 and 84.33±11.86 respectively), thus indicating that the network was probably changing towards a more define configuration. Cells that received three inoculations had wider, but less numerous, meshes (43.89±6.52), and a reduced number of BPs (80.67±11.92) (FIG. 10A, third panel). Tubule length increased (153.89±8.54 µm) suggesting that tubules joined together to improve network configuration. Also in this case, No tubules formation was observed in the control plate (top right corner in each panel).

The bar graph in FIG. 10B presents a semi-quantitative analysis of the spatial organization of HUVECs. The bars, referring to mean tubule length, number of BPs and number of meshes, are divided in three groups according to the number of inoculations of PE received (1, 2 or 3). Data show an increase in mean tubule length from cells that received one inoculation (129.71±12.88 µm) to those that received three (153.89±8.54 µm), suggesting that the cells were organizing into a more mature network. This finding is also supported by the observed decrease in both the number of meshes (from 76.67±19.74 to 43.89±6.52) and of BPs (from 110.78±15.40 to 80.67±11.92). From the statistical analysis performed, a difference was found in all three parameters between cells that received one inoculation and cells that received three.

Figure 11:
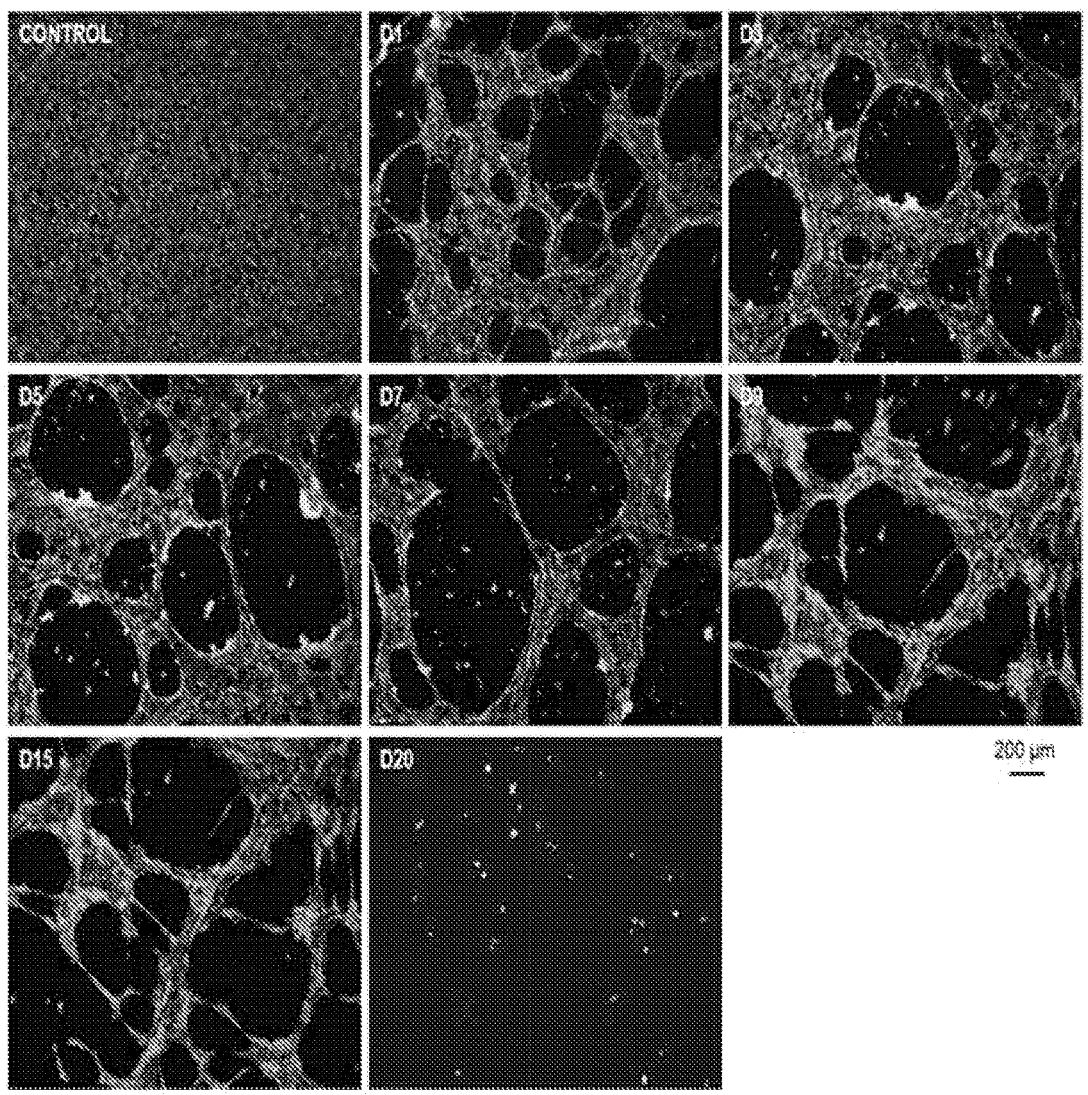
FIG. 11 shows a series of images illustrating HUVECs cultured for three days with PE stored in a humidified 6% $CO_2$ incubator at 37° C. from 1 up to 20 days. The numbers on each image indicates the incubation time (in days). PE maintained its capability to induce angiogenesis even after 15 days of incubation.

As for the retained bioactivity of the extract, it maintains its angiogenic potential until the fifteenth day of storage in a humidified 5% $CO_2$ incubator at 37° C. (FIG. 11). No significant difference was observed between 1 and 7 days of storage. Given all these characteristics of the PE, it was considered suitable for a constant and sustained released over time.

Characterization of Gelatin Microparticles.

Size distribution analysis of gelatin microparticles of several preparations showed that their size range was between 20.886±3.53 and 124.083±13.01 µm. Nearly 80% of them had a diameter in the range of 20-80 µm (FIG. 12B).

Figure 12A:
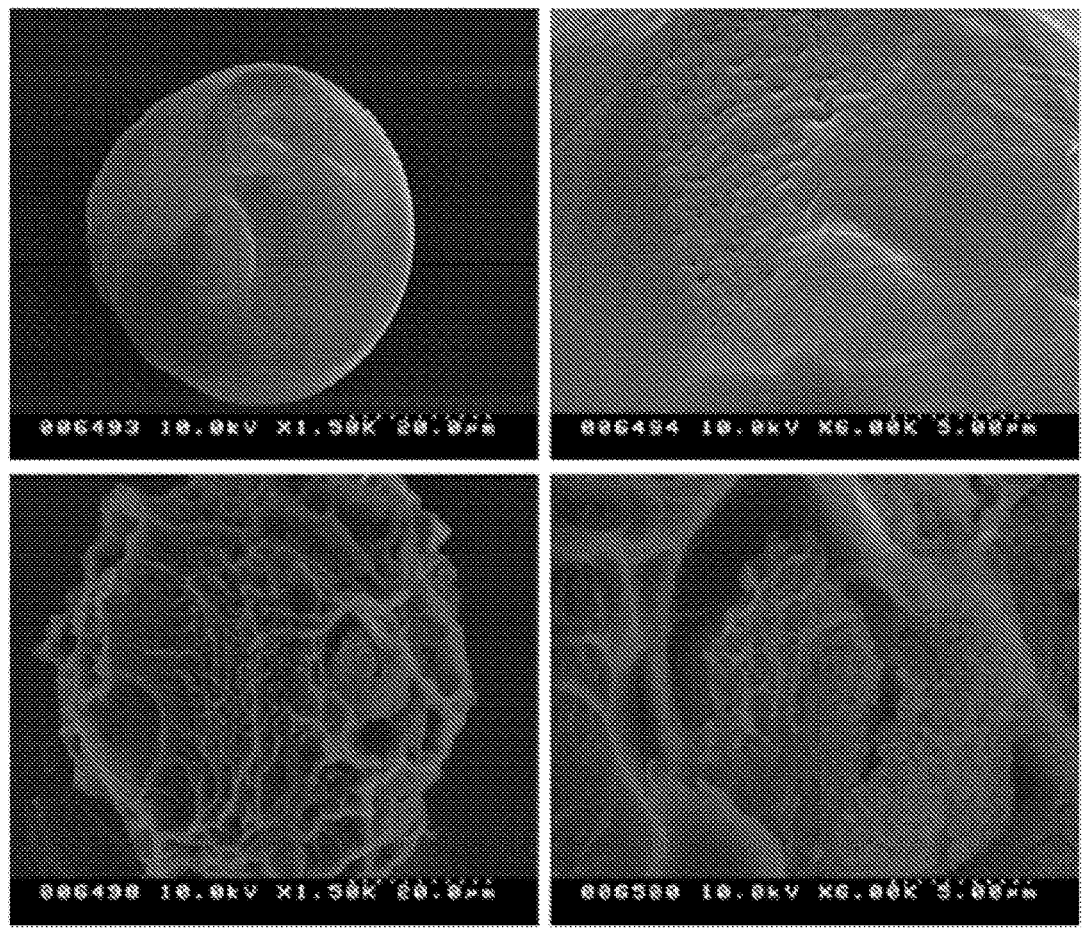
FIGS. 12A-12B illustrate the characteristics of gelatin microparticles.
Figure 12B:
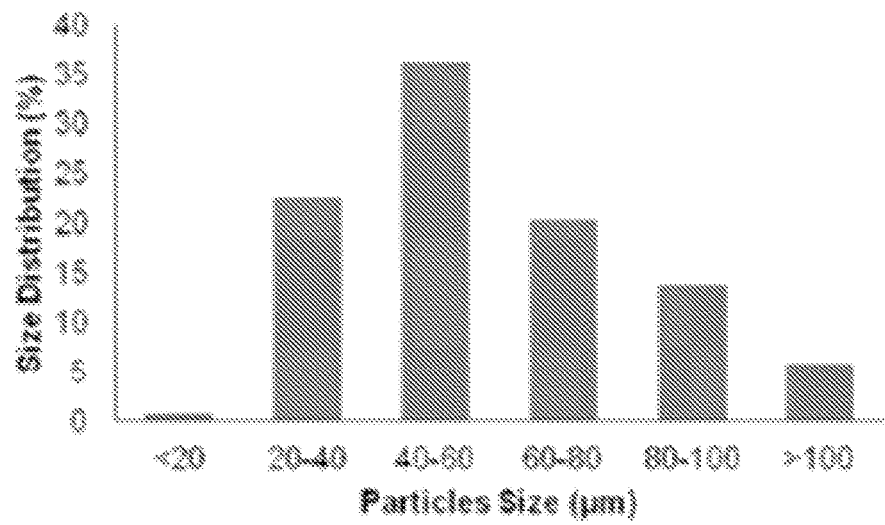

SEM examination of microparticles, illustrated in FIG. 12A, showed a difference in surface morphology between blank and loaded microparticles. Blank microparticles (top row) presented a smooth surface and a regular shape. After loading (bottom row) the particles were bigger and had an irregular surface. These two aspects implies: (i) adhesion of the PE to the surface (adsorption), and (ii) penetration of the PE inside the particles (absorption)[27].

Figure 13:
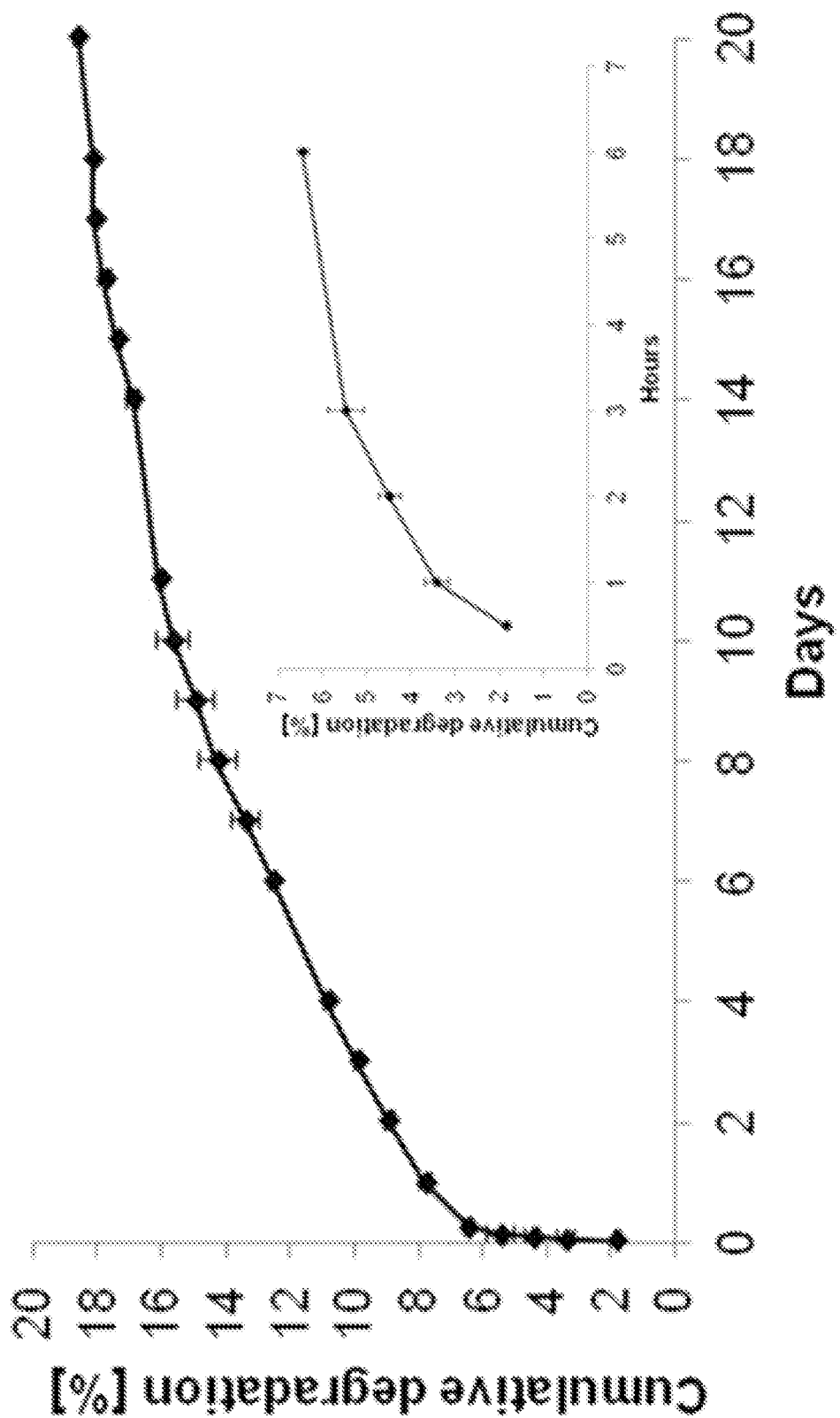
FIG. 13 shows the degradation profile of non-crosslinked microparticles. In vitro cumulative percent degradation of non-crosslinked microparticles is shown as function of their dry weight. Total percent cumulative degradation was and 18.65%±0.09 after 20 days. The inset graph shows degradation after six hours of incubation (6.45%±0.12). Error bars represent mean±standard deviation with n=3.

FIG. 13 shows the degradation profile of non-crosslinked microparticles. This experiment was performed only with blank microparticles to assess the degradation kinetics of gelatin in PBS. An initial burst was observed: after six hours the cumulative percent release was 6.45%±0.12 (FIG. 13, inset). The burst was then followed by a slower release. After 20 days, total cumulative release was 18.65%±0.09 (FIG. 13, main graph).

Figure 14A:
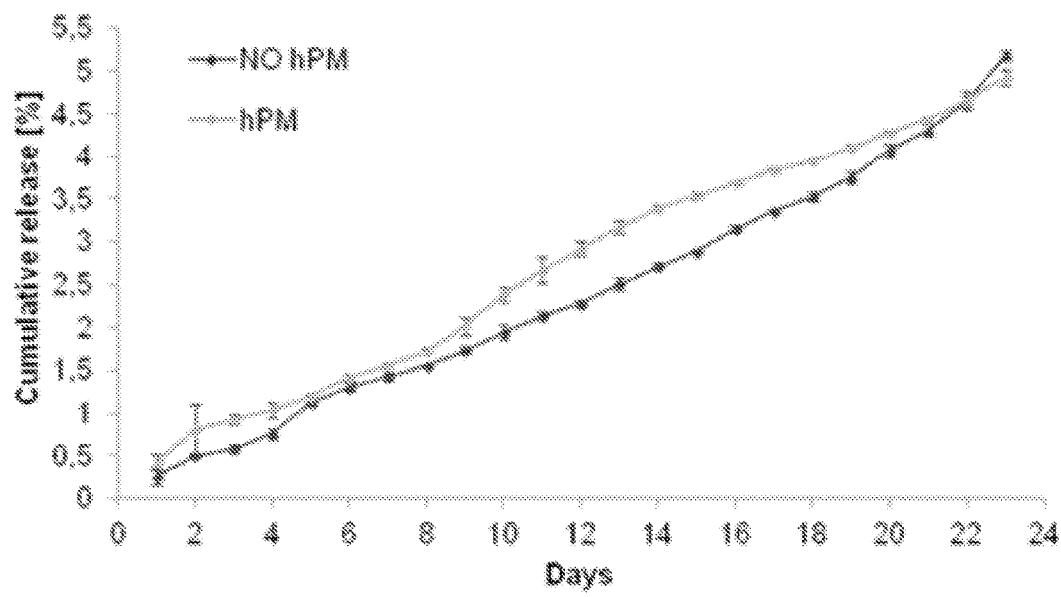
FIGS. 14A-14B illustrate protein release kinetics of blank and loaded microparticles.

FIG. 14A shows in vitro degradation of blank microparticles (black, NO PE) and in vitro release of microparticles loaded with PE (grey, PE). In both cases a small initial burst was observed. After 48 hours the cumulative percent release from loaded microparticles was 1.03%±0.08, while for the blank ones, it was 0.76%±0.05, followed in both cases by a near-constant release. After 22 days cumulative percent release from loaded and blank microparticles was nearly the same: 4.65%±0.07 and 4.65%±0.11, respectively, as it is highlighted also in the graph. On day 23 the release form blank microparticles was slightly greater than the one from the loaded particles (5.18±0.05 and 4.92±0.09 respectively). Base on the evidence that most of the PE has been released, the experiment was concluded.

Figure 14B:
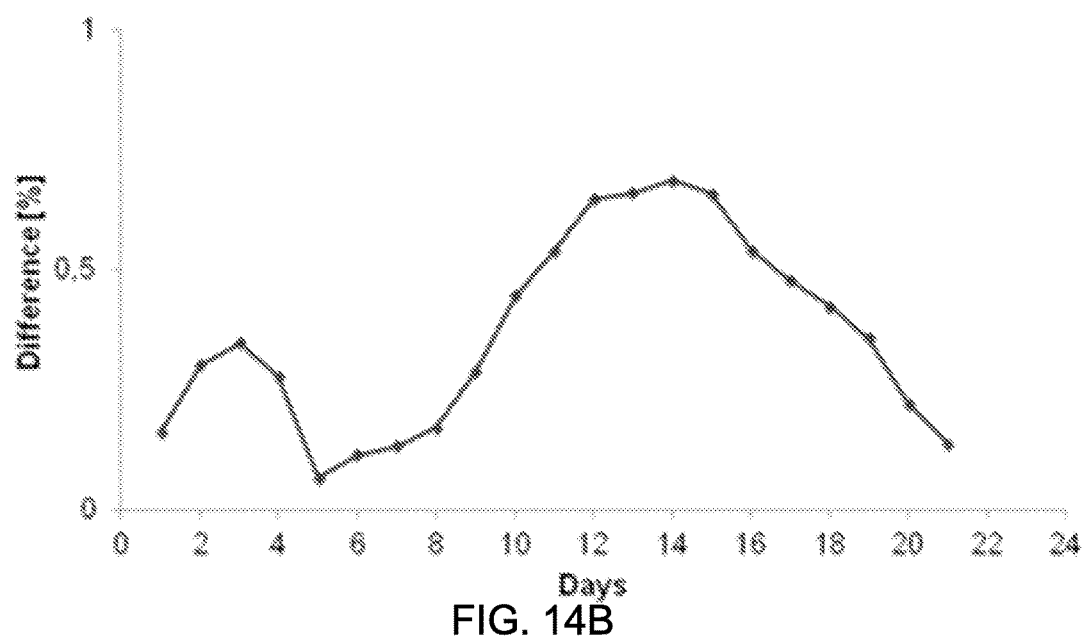

FIG. 14B shows the difference in percent of release between loaded and blank microparticles. Two peaks can be observed: the first from the first hour to day 5 and the second from day 5 to day 22. The first peak indicates that the PE bonded to the particles surface was released at first and in a shorter period of time. The second peak, probably due to the erosion of the bulk of the particles, lasts longer and total cumulative release is greater. This indicates that PE is gradually released from pores or channels formed in microparticles by releasing medium.

In spite of the presence of an initial "burst", the release kinetics showed from microparticles obtained through filtration is close to a zero-order profile, meaning that the release is almost constant. We argue that this may be due to the coexistence of particles of different sizes in the same sample. Release rate is influenced by particles size, precisely smaller microparticles have a greater release as a result of the increased surface area to volume ratio. This phenomenon has already been used to modulate drug or protein release in order to achieve controlled near zero-order release profiles[25].

Total cumulative released both from blank and loaded microparticles is somewhat lower than the values reported in literature, which is usually above the 20%[39,40]. This may be due to a high degree of crosslinking.

3D In Vitro Angiogenesis Assay.

After having determined the optimal cell density and PE volume, the angiogenesis assay was prepared as described in the Methods, above. After 3 days of culture, no sign of tubulogenesis was present and no difference could be noticed between HUVECs seeded with PE-loaded microparticles and the control (result not shown). After 5 days of culture, the cells changed morphology and sprouts were observed, even though no capillary-like network was yet formed (FIG. 15). Sprouting is the initial phase of angiogenesis, thus the presence of sprouts after five days of culture demonstrates an angiogenic response from HUVECs[41]. Since, a network had not formed in three days after seeding, the amount PE released by the particles may have been insufficient to promote angiogenesis in the time frame observed. However, the formation of sprouts indicates that the PE was released and angiogenic response was initiated. The release rate of the microparticles can be optimized to promote tubule formation in a shorter time frame.

Discussion & Conclusion

The findings of this example reveal that the angiogenic response of HUVECs is influenced not only by the incubation time but also by the number of inoculations of PE received. In particular, in initial experiments, the capillary network started forming one day after seeding, became well-defined after three days, and started degrading after five. It was also shown that HUVECs form a more mature capillary network when they received more than one inoculation of PE. Furthermore, in the present example, the networks did not degrade after five days as in the experiment discussed above. Finally, the extract maintains its angiogenic potential until the fifteenth day of storage. Given all these characteristics of the PE, it can be considered suitable for a constant and sustained released over time. Thus, a method of drug delivery for the multi-protein mixture was developed using biodegradable gelatin microparticles to further preserve bioactivity, to control and to extend the delivery of hPE, with the goal of improving its ability to induce and modulate angiogenesis To this purpose, biodegradable gelatin microparticles were prepared as a delivery system for PE. Absorption and adsorption of hPE into the gelatin particles was assessed by SEM examination and by an analysis of in vitro release kinetics. SEM analysis showed an increase in size and changes in morphology between loaded and blank particles, which is the result of adhesion of hPE to the surface (adsorption) and/or penetration of into the particles (absorption). Release kinetics showed two peaks, with the first peak believed to be the result of release of proteins bonded on the surface of the microparticles, with this peak being smaller than the second peak and occurring over a shorter period of time. The second peak was believed to result from bulk erosion because it had higher total cumulative release over a longer period of time. Despite an initial "burst", the release kinetics was close to a zero-order profile after day 1. The analysis revealed the particles were suitable for use as a vehicle for the sustained release of the extract in a 3D in vitro angiogenesis assay.

These studies also show that when incorporated into a 3D type-I collagen matrix, hPE-loaded-gelatin microparticles induced cells into an elongated morphology and the initial stages of tubule formation with some cell sproutings after five days of culture (FIG. 15, right). Since sprouting is the initial phase of angiogenesis, the presence of sprouts implies an angiogenic response from HUVECs. The observed total cumulative released both from blank and loaded microparticles was near 5% after 23 days, which is significantly lower than the values of 20-30% reported in literature when single proteins are released from gelatin microparticles. Despite the low cumulative release, the concentration of hPE released by the particles was still high enough to produce an angiogenic response within the collagen hydrogel. Thus, hPE-loaded-gelating microparticle embedded collagen hydrogels have potential applications in in vitro angiogenesis assays with using ranging from screen anti-angiogenesis cancer drugs to mechanistic studies of tubule and angiogenic network formation.

Overall, this example demonstrated that biodegradable gelatin microparticles can be used as a vehicle for sustained release of the multiprotein hPE in a 3D angiogenesis assay. Cell sprouting was observed after five days of culture using hPE-loaded-gelatin microparticles, but no interconnected capillary network formed. An increase in the amount of hPM released by the particles or an extension of the culture time may promote the formation of more interconnected capillary networks.

References for Example 2

1. http://www.donatelifeny.org/about-donation/data/.
2. Kim, B.-S. & D. J., M. Development of biocompatible synthetic extracellular matrices for tissue engineering. *Trends in Biotechnology* 16, 224-230 (1998).
3. Bach, F. H. Xenotransplantation: problems and prospects. *Annual review of medicine* 49, 301-310 (1998).
4. Dvir, T., Timko, B. P., Kohane, D. S. & Langer, R. Nanotechnological strategies for engineering complex tissues. *Nature nanotechnology* 6, 13-22 (2011).
5. Langer, R. & Vacanti, J. Tissue Engineering. *Science* 260, 920-926 (1993).
6. Martin, Y. & Vermette, P. Bioreactors for tissue mass culture: Design, characterization, and recent advances. *Biomaterials* 26, 7481-7503 (2005).
7. Muschler, G. F., Nakamoto, C. & Griffith, L. G. Engineering Principles of Clinical Cell-Based Tissue Engineering. *The Journal of Bone and Joint Surgery* 1541-1558 (2004).
8. Laschke, M. W. et al. Angiogenesis in tissue engineering: breathing life into constructed tissue substitutes. *Tissue engineering* 12, 2093-104 (2006).
9. Soker, S., Machado, M. & Atala, a Systems for therapeutic angiogenesis in tissue engineering. *World journal of urology* 18, 10-8 (2000).
10. Adair, T. H. & Montani, J.-P. Angiogenesis. *Colloquium Series on Integrated Systems Physiology: From Molecule to Function* 2, 1-84 (2010).
11. Stein, I., Neeman, M., Shweiki, D., Itin, A. & Keshet, E. Stabilization of vascular endothelial growth factor mRNA by hypoxia and hypoglycemia and coregulation with other ischemia-induced genes. *Molecular and Cellular Biology* 15, 5363-8 (1995).
12. Pardali, E., Goumans, M.-J. & Ten Dijke, P. Signaling by members of the TGF-β family in vascular morphogenesis and disease. *Trends in Cell Biology* 20, 556-567 (2010).
13. Vailhé, B., Vittet, D. & Feige, J. In Vitro Models of Vasculogenesis and Angiogenesis. 81, 439-452 (2001).
14. Largo, R. A., Ramakrishnan, V. M. & Ehrbar, M. Angiogenesis and Vascularity for Tissue Engineering Applications. (2010).
15. Carmeliet, P. Angiogenesis in health and disease. *Nature medicine* 9, 653-60 (2003).
16. Achen, M. G. & Stacker, S. A. The vascular endothelial growth factor family; proteins which guide the development of the vasculature. *International Journal of Experimental Pathology* 79, 255-265 (1998).
17. Carmeliet, P. Mechanisms of angiogenesis and arteriogenesis. *Nature medicine* 6, 389-95 (2000).
18. Formiga, F. R. et al. Angiogenic therapy for cardiac repair based on protein delivery systems. *Heart failure reviews* 17, 449-73 (2012).
19. Iruela-Arispe, M. & Dvorak, H. Angiogenesis: A dynamic balance of stimulators and inhibitors. *Thrombosis and Haemostasis* 78, 67-677 (1997).
20. Lee, K., Silva, E. A. & Mooney, D. J. Growth factor delivery-based tissue engineering: general approaches and a review of recent developments. 153-170 (2011).doi:10.1098/rsif.2010.0223
21. Moore, M. C. Modulation of nutrient deficiencies occurring in engineered ex vivo tissue scaffolds. (2013).
22. Vasir, J. K., Tambwekar, K. & Garg, S. Bioadhesive microspheres as a controlled drug delivery system. *International Journal of Pharmaceutics* 255, 13-32 (2003).
23. Chaturvedi, G. *Microspheres technology and its application*. (2009).
24. Determan, A. S., Trewyn, B. G., Lin, V. S.-Y., Nilsen-Hamilton, M. & Narasimhan, B. Encapsulation, stabilization, and release of BSA-FITC from polyanhydride microspheres. *Journal of controlled release: official journal of the Controlled Release Society* 100, 97-109 (2004).
25. Narayani, R. & Panduranga Rao, K. Gelatin microsphere cocktails of different sizes for controlled release of anticancer drugs. *International journal of pharmaceutics* 143, 255-258 (1996).
26. Tamizharasi, S., Rathi, J. & Rathi, V. Formulation and Evaluation of Pentoxifylline-loaded poli-e-caprolattone microspheres. *Ind J of Pharm Sci* 70, 333-5 (2008).
27. Cohen, S., Yoshioka, T., Lucarelli, M., Hwang, L. H. & Langer, R. Controlled Delivery Systems for Proteins Based on Poly(Lactic/Glycolic Acid) Microspheres. *Pharmaceutical Research* 8, 713-720 (1991).
28. Vernon, R. B. & Sage, E. H. A Novel, Quantitative Model for Study of Endothelial Cell Migration and Sprout Formation within Three-Dimensional Collagen Matrices. 133, 118-133 (1999).
29. Staton, C. a, Reed, M. W. R. & Brown, N. J. A critical analysis of current in vitro and in vivo angiogenesis assays. *International journal of experimental pathology* 90, 195-221 (2009).
30. Montesano, R. & Pepper, M. S. Three dimensional in vitro assay of endothelial cell invasion and capillary tube morphogenesis. *Vascular Morphogenesis: In vivo, in vitro, in mente* 79-110 (1998).
31. Auerbach, R., Lewis, R., Shinners, B., Kubai, L. & Akhtar, N. Angiogenesis assays: a critical overview. *Clinical chemistry* 49, 32-40 (2003).
32. Jaffe, E. A., Nachman, R. L., Becker, C. G. & Miinick, C. R. Culture of Human Endothelial Cells Derived from Umbilical Veins. 52, 2745-2756 (1973).

Example 3

Placental Extract Release from PLGA Microparticles to Modulate Angiogenesis

Introduction

Single administrations of human placental extract of the present disclosure have been shown to induce and modulate the initial stages of in vitro and in vivo angiogenesis as described above in Example 1. Multiple administrations of hPM over time were shown to promote further capillary network development, and thus controlled delivery was hypothesized to further stabilize network formation over extended time periods, as described in Example 2, above. In the present example, hPE was encapsulated in poly(lactic-co-glycolic acid) (PLGA) microparticles to extend the release period. Microparticle preparation was optimized for hPE loading, morphological features (size, encapsulation efficiency, porosity) were characterized and protein release was profiled.

To overcome issues identified above for inducing angiogenesis for implanted tissues or tissue constructs, in the methods of the present disclosure human placenta was used to derive a human placental extract, referred to in the present example as a human placental matrix (hPM) that is capable of inducing capillary network formation and contains angiogenic and immunomodulatory proteins, as described in the examples above. In vitro, endothelial cells (HUVECs) seeded onto hPM were shown above to form angiogenic networks with upregulation of angiogenic genes, and in vivo the matrix was shown to induce blood vessel formation within dosed bioscaffolds, while inhibiting tissue fibrosis. Additionally, endothelial cells receiving multiple hPM inoculations at regular time points (day 1, day 3 and day 5 of culture) formed more stable, longer lasting angiogenic networks in comparison to cells receiving only a single inoculation whose networks begin to degrade after 5 days. Thus, approaches for controlled delivery of the matrix over time were investigated to allow longer lasting and more stable capillary network formation.

The complex and heterogeneous nature of hPM can complicate controlled release mechanisms. For example, different charges and chain properties of proteins can have effects on loading efficiency, because of reciprocal interaction and interaction with the material used for the controlled release. Both natural and synthetic microparticle materials have been investigated for their potential to encapsulate proteins. Natural materials such collagen, chitosan, and alginate offer biocompatibility and non-aggressive encapsulation technique, and they have degradation rates of between about 7 and 10 day, which allows some degree of sustained release but may limit use for longer term sustained protein release[11,12,13]. Chemical or photochemical crosslinking could slow degradation of these microparticles[9,14].

PLA-copolymers have been used for protein encapsulation in biomedical applications, and are FDA approved biocompatible synthetic materials[15,16,17]. These polymers can provide a long lasting controlled release of proteins, and can be used to create composites and multi-layered microparticles[15,18]. Among these materials, PLGA or poly(lactic-co-glycolic acid) is used for controlled release of specific growth factors (for example BMP, VEGF, bFGF)[19,20,21].

While studies have evaluated the PLGA encapsulation of single proteins, and a few have investigated co-encapsulation of multiple proteins,[22,23] no studies have evaluated the encapsulation of a complex heterogeneous mixture of proteins. The present example describes a composition and encapsulation technique for hPM using PLGA microparticles and evaluates the effect of the controlled release of this mixture in a 3D culture of endothelial cells.

Given the heterogeneous composition of the hPM, in the present embodiment described in this example, the PLGA synthesis protocol was optimized to suit multiprotein hPM release for applications in cell culture. Considerations included optimization of microparticle size (to be suitable for regenerative medicine applications), high loading and encapsulation efficiency, low initial burst, and controlled release profile. Additionally, it was confirmed that hPM was released from the microparticles in concentrations adequate to induce angiogenesis using endothelial cells. Following microparticle synthesis and loading, analysis was performed to evaluate if the encapsulation process was selective for hPM proteins. The effect of controlled hPM release on the induction of angiogenesis was assessed using a 3D culture system with hPM-loaded microparticles embedded into an alginate-based hydrogel seeded with HUVECs. Cell behavior was assessed at specific time points during 28 days to evaluate the response between cells receiving single, direct inoculations of hPM at day 1 in comparison to cells receiving a controlled dose of hPM from PLGA microparticles throughout the entire period of culture.

Methods

Effect of Multiple Bolus hPM Inoculations.

Analysis of the effect of hPM dosing profiles during angiogenic network formation was determined in vitro using HUVECs by pipetting and evenly coating wells of a 96-well tissue culture plate using an orbital shaker at 30 rpm for 1 minute. The plate was then incubated at 37° C. for 30 minutes to allow the hPM to warm up. HUVECs were suspended in Angiogenic media, pipetted on the top of the hPM and then placed in a humidified 6% $CO_2$ incubator at 37° C. For a control, HUVECs were cultured at 20,000 cells/cm$^2$ in Angiogenic media. Three different profiles of hPM inoculations were compared: 1) hPM was added only inoculated on day 1 (day of seeding), 2) hPM was inoculated on day 1 and 3, and 3) hPM was inoculated on day 1, 3 and 5. Cells were cultured for 7 days and media was replaced on day 3 and 5. As a control, cells were directly seeded at the same density directly onto the bottom of the plate, and media was replaced every two days. Cells were stained on day 7, imaged with a fluorescence microscope and angiogenesis was quantified by analyzing images as described in the "Angiogenesis Quantification" section.

PLGA Microparticle Preparation.

PLGA (Poly(DL-lactide-co-glycolide)) microparticles were prepared using a water-in oil-in-water emulsion (PROTOCOL 1) (Durect, Cupertino, Calif.). One water solution (W1) was prepared using the hPM protein mixture as previously described in Example 1, and the other water solution (W2) was prepared by dissolving 2 g of polyvinyl alcohol (wt 30000-70000, 87-90% hydrolyzed, Sigma-Aldrich, St. Louis, Mo.) in 100 mL of DI water. The oil solution (O) was obtained by dissolving 90 mg of PLGA in 3 mL of chloroform until the solution appeared clear. W1 was added to O and homogenized at 20000 rpm for 1 minute. Using a micropipette, the obtained primary emulsion was added dropwise in W2 while stirring at 300 rpm. When all the primary emulsion was added, the resulting secondary emulsion was covered loosely with an aluminum foil and left to stir (300 rpm) overnight in a fume hood to let the solvent evaporate. Next, the secondary emulsion was centrifuged at 1000 rpm for 10 minutes, the supernatant removed and the microparticles washed two more times with DI water. The hardened microparticles were suspended in DI water, freeze-dried for 48 hours and then stored at 4 C until needed. For the control, single protein loaded PLGA microparticles were created by substituting bovine serum albumin (BSA) to make W1 instead of the hPM (Sigma-Aldrich, St. Louis, Mo.).

Due to the heterogeneous nature of the hPM mixture, encapsulation represents a challenging element of controlled release from PLGA micro particles. Thus, the influence of modifications to the protocol on size and release was analyzed. Firstly, the effect of a longer homogenization of the primary phase was evaluated (PROTOCOL 2: 2 minutes instead of 1 minute). Next, the effect of an additional homogenization step introduced after the formation of the secondary water-in-oil-in-water emulsion and before the solvent removal was investigated (Protocol 3: 1 minutes of additional homogenization; Protocol 4: 20 seconds of additional homogenization). After each modification, before proceeding in the optimization process, the microparticles morphological features and associate release rates were evaluated and compared.

PLGA Microparticle Morphological Characterization.

Morphologic features of PLGA microparticles were evaluated using microscopy. The average size of the microparticles was evaluated using an inverted optical Leica microscope with attached color digital camera (Leica DM IL LED, Leica Microsystems Inc., IL, USA). Images taken were analyzed using the free software ImageJ 1.45s (Wayne, Rasband—National Institutes of Health, USA—http://imagej.nih.gov/ij/). The diameter of each particle was determined by manually tracing the particles followed by automatically measured using the Leica LAS software (Wetzlar, Germany).

Surface morphology and porosity of the microparticles were characterized using scanning electron microscopy (SEM) (S-4000 FE-SEM, Hitachi High Technologies, TX, USA). For the shape and surface analysis, freeze-dried samples were mounted on aluminum stubs with double sided graphite tape and coated with gold and palladium using a scatter (deskV, Denton Vacuum). The coated samples were then examined at an acceleration voltage of 2 kV and photographed using low magnification to evaluate the average dimension and shape, and high magnification to evaluate the change in porosity and morphology features.

Loading Efficiency.

hPM loading efficiency in PLGA microparticles was determined using a direct measurement of encapsulated protein after microparticles dissolution. It was performed by adaptation of a hydrolysis technique described in Ravi., et al., *Development and characterization of polymeric microspheres for controlled release protein loaded drug delivery system*. 70, (2008) and Igartua, M. et al., Stability of BSA encapsulated into PLGA microspheres using PAGE and capillary electrophoresis. *International Journal of Pharmaceutics* 169, 45-54 (1998), both of which are incorporated by reference herein for the hydrolysis technique. Briefly, 15 mg of lyophilized microspheres were digested with 5 mL of 0.1 M NaOH containing 5% w/v SDS and hydrolyzed on a shaker for 15 h, at room temperature until a clear solution was obtained. The resulting clear solution was then neutralized to pH 7 by addition of 1 M HCl and centrifuged at 5000 rpm for 10 min. Protein concentration in the supernatant was then analyzed in triplicate using a UV-Visible Spectrophotometer at 562 nm, with a Pierce BCA standard protein assay. The encapsulation efficiency was expressed as the ratio of actual to theoretical protein content.

Characterization of In Vitro hPM Release.

To characterize release of hPM from PLGA microparticles, 10 mg of loaded-microparticles were suspended in 1 mL of Phosphate Buffer Saline (PBS). The tubes were incubated in a shaker-incubator, and three samples were evaluated for each protocol. Every 2 days the tubes were centrifuged at 5000 rpm for 5 minutes, the supernatant was collected, and an equal volume of fresh PBS was added to the tube. Protein concentration was quantified by measuring the absorbance at 562 nm with a spectrophotometer. A comparison between results from a standard Pierce BSA assay and a micro-protein BSA assay was performed to obtain more reliable evaluation of the released proteins at every time point tested. Measurements were collected in triplicate. Protein concentrations were compared to freshly prepared standards ranging from 200 to 0.5 µg/mL. Average absorbance of standard PBS was subtracted from all measurements. The amount of proteins in each sample was summed with the amount at each previous time point to build a cumulative release curve.

Since hPM is a complex protein mixture that includes growth factors, extracellular matrix proteins, and biomolecules characterized by various charges and properties, these studies analyzed the proteins release from the hPM loaded-microparticles to determine if selectively encapsulation occurred. An SDS-PAGE analysis was performed on the supernatant collected after overnight stirring. Four solutions were analyzed, including supernatant from hPM-loaded and BSA-loaded microparticles, as well as hPM and BSA in PVA at the same concentrations used when loading microparticles (10 mg BSA in 50 mL DI water and 50 µL hPM diluted in 5 mL DI water). Protein standards where used to assess the molecular weight of the detected proteins. SDS-page was performed using a BIO-RAD electrophoresis system (Hercules, Calif.). Following electrophoresis, the poly-acrylamide gels were stained with Coomassie Blue for one hour under continuous shaking. Protein bands were then enhanced by destaining the gel in a 4:1:5 Methanol:Acetic Acid:DI water solution. The final gel was washed in DI water and imaged.

Alginate-Hydrogel Based 3D Culture.

An angiogenesis assay using loaded microparticles was created to assess applications for controlled hPM release. Human Umbilical Vein Endothelial Cells (HUVEC) were seeded and cultured in a 3D alginate gel (1.5% Alginate) with embedded hPM-loaded microparticles. Sample group included cells suspended in Alginate containing pure hPM, cells suspended in Alginate containing embedded hPM-loaded microparticles, cells suspended in Alginate without microparticles, and cells suspended in Alginate with blank microparticles. For all sample groups, HUVECs were suspended in media and gently suspended in the Alginate matrix before polymerization by pipetting of a 0.054M Calcium Chloride solution. The Alginate-cell suspensions were held steady to allow 15 minutes for polymerization, then the gels were washed with PBS, culture media was added, and the plate was incubated in a humidified 6% CO2 incubator at 37° C.

To obtain comparable results between the condition where hPM was added directly to the matrix and the condition where hPM was released from microparticles, the concentration of hPM mixed in each respective gel was equal to the concentration of protein released after 21 days from the embedded microparticles (78 µg of proteins per $cm^2$). The effect of sustained controlled-hPM release from microparticles was compared to bolus inoculations of hPM at 7, 14, 21 and 28 days by morphological characterization of cell networks within gels stained using Calcein AM (Life Technologies, Grand Island, N.Y.).

Angiogenesis Quantification.

Quantification of angiogenesis output was performed using ImageJ 1.45s (NIH, Bethesda, Md.). Images at 5× magnification taken using the inverted fluorescence microscope were processed evaluating and quantifying the following parameters: number of meshes, number of branching points and length of the tubule-like structures formed by HUVEC during time as described in Example 1.

Statistical Analysis.

Experiments both for microparticles and for 3D culture were performed in triplicate. All graphs and tabulated data were displayed as mean±mean standard error. Analysis was performed using Excel (Microsoft Office) and Minitab 15 (Minitab, State College, Pa.). Significance was calculated using ANOVA tests were more than two conditions were evaluated, and specific differences were evaluated using post-hoc tests. When only two conditions were compared unpaired, two-tailed, Student's t-Test with unequal variance were used. Significance levels were set at * $p<0.05$.

Results

Effect of Multiple Bolus hPM Inoculations.

Figures 16A, 16B:
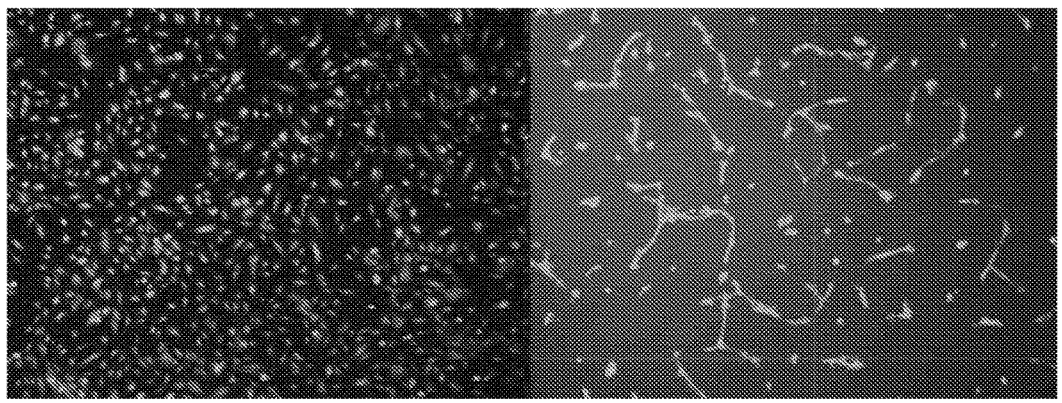
FIGS. 16A-16G illustrate the effect of a continuous delivery of hPE on HUVECs.
Figures 16C, 16D:
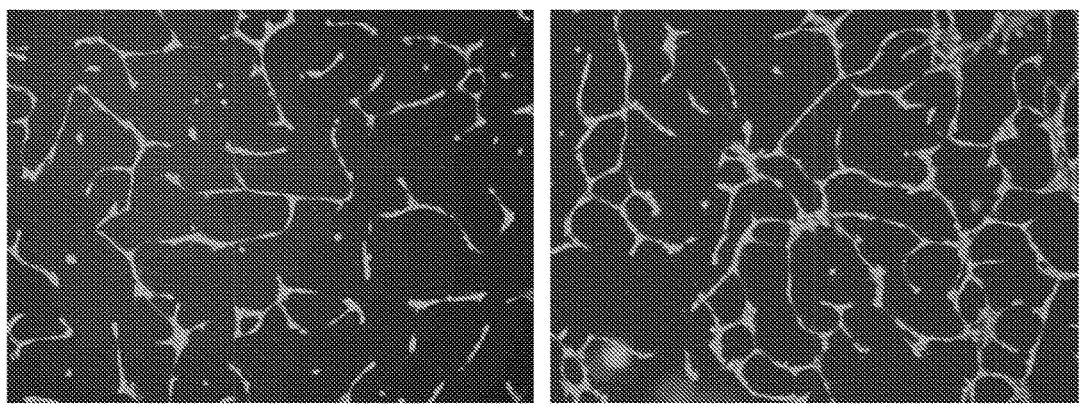
Figure 16E:
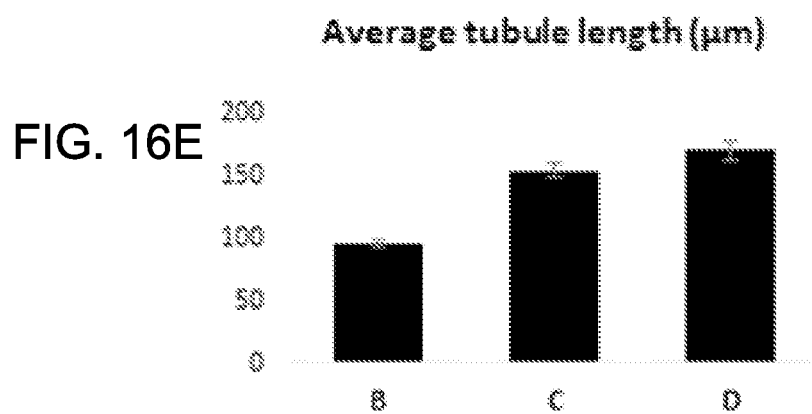
Figure 16F:
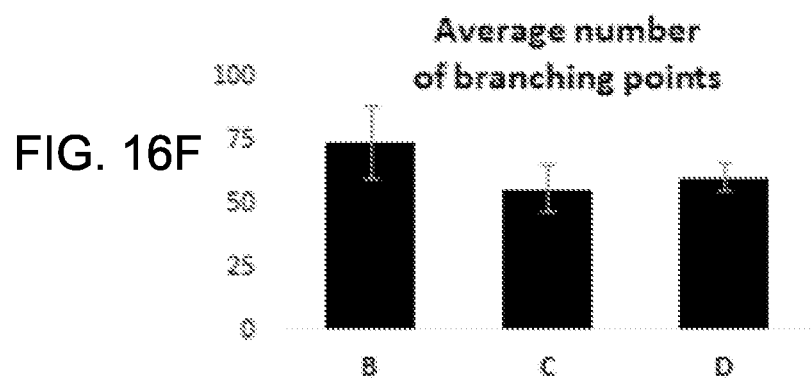
Figure 16G:
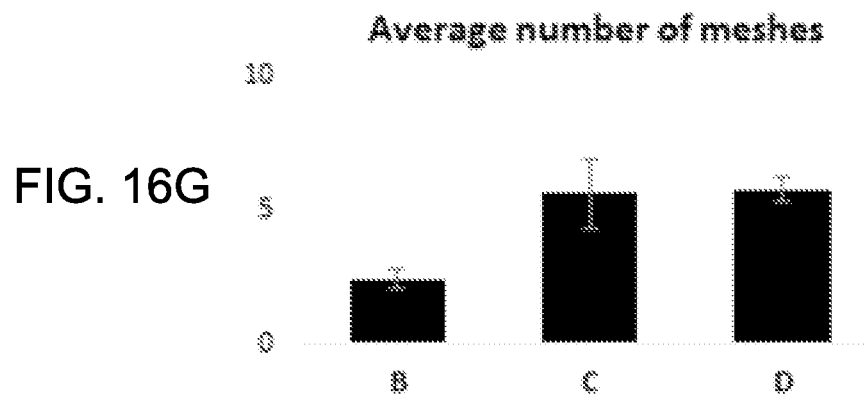

The formation of HUVECs into angiogenic networks was affected by the number of doses of hPM received over time (FIGS. 16A-16D). As shown in FIG. 16E, tubule length increased as a function of the number of inoculations. Although no significant differences occurred for the number of meshes and number of branching points (FIGS. 16F-16G), a trend of increased and more mature meshes was observed as a function of the number of inoculations. Since mature angiogenesis is characterized by long tubules and a reduced number of branching points and meshes, the results confirm that continuous administration of hPL helps endothelial cells to organize in a stable network.

Initial PLGA Microparticle Preparation: Protocol 1.

PLGA microparticles resulting from protocol 1 had an average size of 447±32 µm and a normal distribution of sizes ranging from 100 to 1000 µm. Three batches of microparticles were prepared under the same conditions, and repeatable distributions could be demonstrated. The loading efficiency of hPM in the PLGA microparticles was 64±4% (data not shown).

In vitro release analysis showed a low initial burst, corresponding to 10% of the total amount of protein encapsulated, (21.38±0.83 µg/mL), while 51.23±0.19% (134.56±0.50 µg/mL) of the protein initially encapsulated was released from PLGA microparticles after 21 days (data not shown). The release rate profile appeared linear and constant through the 21 day period evaluated, but the amount of hPM released from the microparticles at the end of the evaluated period was significantly lower in concentration when compared to the use of bolus injections of hPM (500 µg/mL) to induce an angiogenic response (as described above).

Control BSA-loaded PLGA microparticles had an average size of 239.60±9.45 µm and a normal distribution of sizes from to 50 to 400 µm, with 70% of microparticles in the range between 150 and 350 µm. The loading efficiency of BSA loaded PLGA microparticles was 76±3% of the total amount of protein loaded initially. In vitro release analysis showed a higher initial burst compared to hPM loaded microparticles at 20% of the total amount of BSA encapsulated, (51.52±1.76 µg/mL), while 66.7±9.55% (166.74±23.8 µg/mL) of the protein initially encapsulated was released from PLGA microparticles after 21 days (data not shown). The release rate profile appeared linear and constant through the period evaluated. The differences in results observed between hPM and BSA loaded PLGA microparticles suggested that release kinetics could be improved through optimization of the preparation and loading protocol.

Optimization of PLGA Microparticle Size and Characterization of Morphology.

Figure 17D:
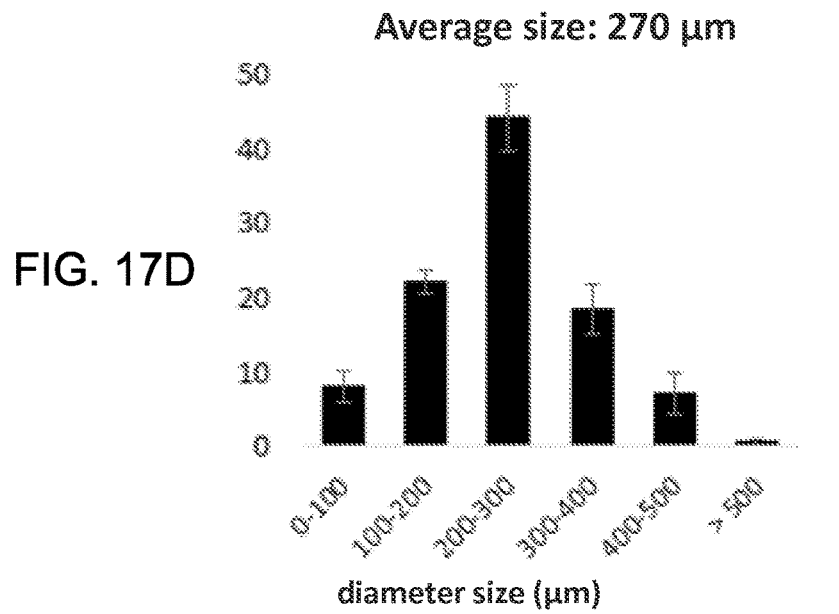
Figure 17E:
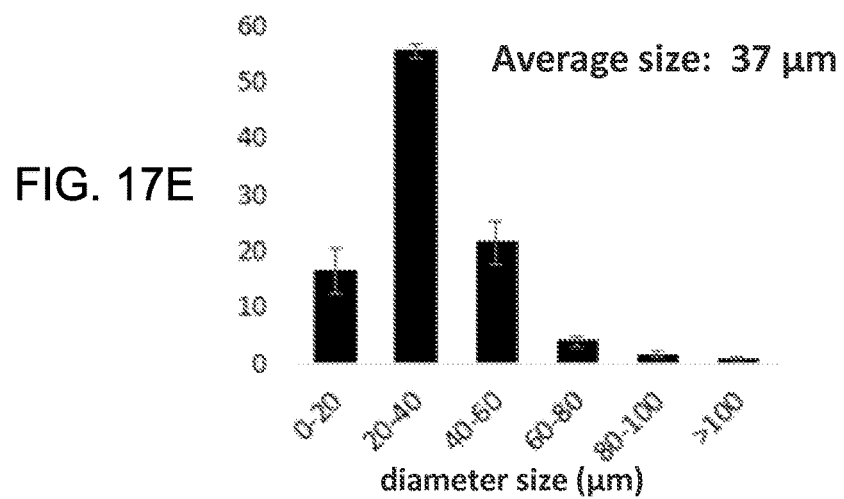
Figure 17F:
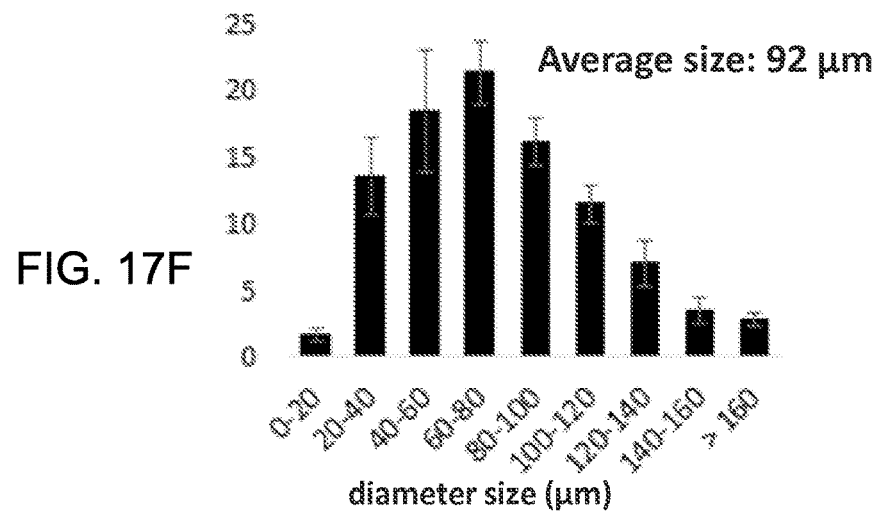

Size analysis from microparticles created using protocol 2, in which the primary emulsion was homogenized for 2 minutes (one additional minute than protocol 1), showed an average diameter of 276.78±13.41 µm (FIGS. 17A, 17D). Microparticles created using protocol 3, which had a 1 minute homogenization step added to the secondary emulsion preparation steps, had an average size of 37.79±1.30 µm (FIGS. 17B, 17E), whereas microparticles created using protocol 4, which had a 20 second homogenization step added to the secondary emulsion, had an average size of 91.85±2.92 µm (FIGS. 17C, 17F).

Results from SEM analysis did not show significant differences in surface porosity between the different protocols. The surface of microparticles obtained with the different modifications described all appeared to be round shaped with a homogeneous surface (FIGS. 18A-18F). FIGS. 18A-18C show the microparticle shape and FIGS. 18D-F show the microparticle surface porosity of particles prepared by protocols 2, 3, and 4, respectively.

Loading Efficiency.

The encapsulation efficiency did not appear to be correlated linearly with the size of the microparticles (FIG. 19A). Encapsulation efficiency was shown to increase for PROTOCOL 2 to 73±4% and to decrease to 63±3% when size was significantly reduced in PROTOCOL 3. The highest encapsulation efficiency was obtained with PROTOCOL 4, with the 79±9% of protein encapsulated of the initial total protein loading.

In Vitro Release of hPM from Optimized hPM-Loaded Microparticles.

The release rate of hPM from microparticles created using optimized protocols were the direct result of differences in the size and loading efficiencies, and the release profile trends obtained by modifying the homogenization steps appeared to be similar. Initial burst did not change significantly with modification of the duration of the primary emulsion homogenization step, going from the 8.14±0.31% in protocol 1 (21.38±0.83 µg protein/mL) (data not shown) to the 6.42±2.07% of protocol 2 (18.88±6.11 µg protein/mL). A significant increase in burst release was observed when the homogenization of the secondary emulsion was introduced: for protocol 3, 23.75±0.40% of the total protein encapsulated (60.82±1.03 µg/mL) was released within the first day in comparison to 27.72±3.73% (106.33±14.33 µg/mL) for protocol 4 (FIG. 19B)

Cumulative release after 21 days correlated with microparticle size, with smaller microparticles allowing for the greater hPM released in the assayed time period. After 21 days of release, microparticles from protocol 2 released 64.09±1.70% (188.43±5 µg/mL) of the total protein encapsulated, whereas MPs from protocol 3 released 98.62±1.40% (252.48±3.6 µg/mL), and MPs from protocol 4 released 87.60±1.12% (335.98±4.72 µg/mL) (FIG. 19B). Further analysis to compare P3 and P4 release profiles over an extended period of time showed that after 30 days microparticles from protocol 3 were completely degraded and no longer releasing hPM, while microparticles from protocol 4 were releasing up to 93.12±0.2% (357±4.09 µg/mL) of the total proteins encapsulated.

Figure 20:
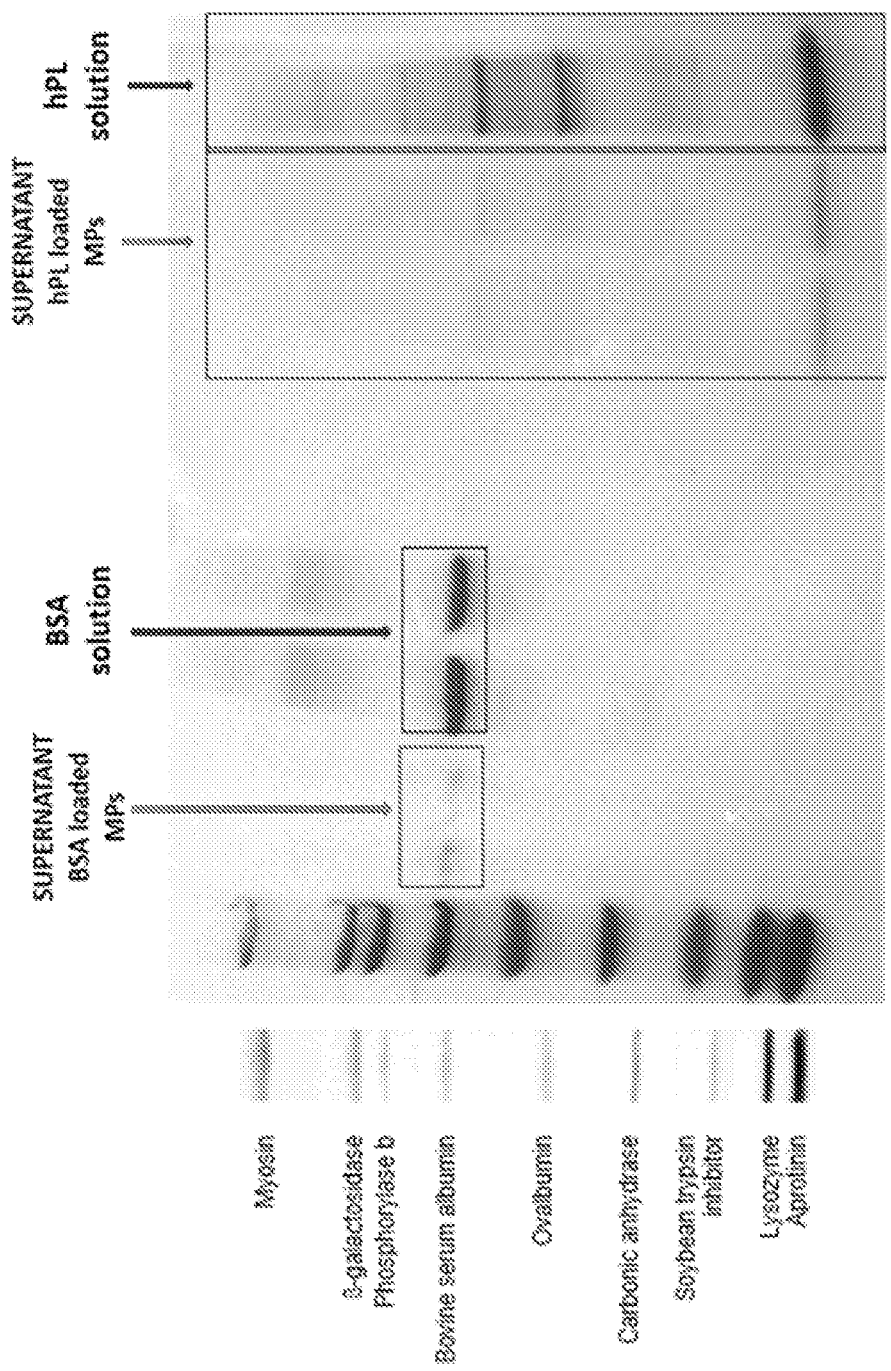
FIG. 20 illustrates SDS page analysis of supernatant of microparticles. The images is of the gel after staining showing qualitative protein content in supernatant of BSA-loaded and hPM-loaded microparticles and of the relative initial content loaded during microparticle preparation.

Results from SDS page were limited by the low concentration of protein contained in the supernatant collected and analyzed. However, analysis showed a uniform encapsulation of hPM in PLGA microparticles without any evidence of selective encapsulation for specific proteins. For both BSA-loaded and hPM-loaded microparticles, the analysis of the supernatant collected after microparticles hardening showed a similar protein content with lower concentration (FIG. 20).

Alginate-Hydrogel Based 3D Culture.

Figure 21:
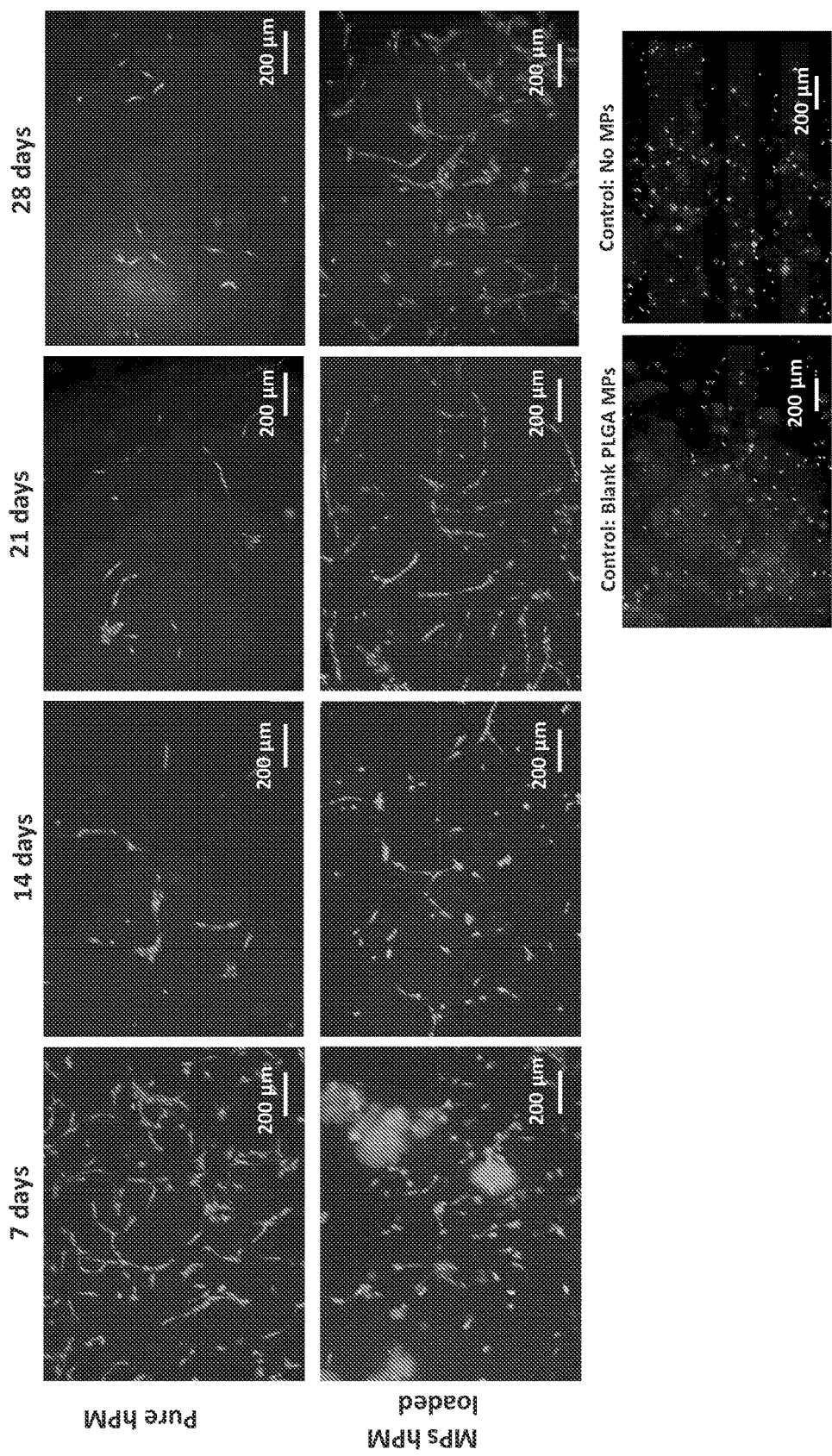
FIG. 21 is a series of images illustrating endothelial cells stained with Calcein AM after 7, 14, 21, and 28 days of culture to evaluate the difference between angiogenic network stability when pure hPM is added to Alginate matris (top row) vs. sustained release of hPM from PLGA microparticles embedded in the matrix (second row). The bottom row shows two controls: one with embedded blank PLGA microparticles in alginate matrix and the second with no microparticles. The HUVECS maintained a generally circular shape throughout all time points for both controls.

Results from the angiogenic assay showed that controlled release of hPM can improve the stability of capillary-like structures in endothelial cell seeded matrices. FIG. 21 illustrates that after 7 days of culture, only a few sprouts and tubular structures were observed in HUVECs cultured in Alginate hydrogels with embedded hPM-loaded microparticles (and no mature network were observed), whereas angiogenic formations in matrices containing pure hPM were comparatively more mature in the same timeframe, with average tubule lengths of 207.90±15.31 µm, with 1.27±0.84 meshes/mm$^2$, and with 9.60±0.70 branching points/mm$^2$. However, after 14 days of culture, alginate gels embedded with hPM-loaded MPs started to organize primary tubules with an average length of 137.41±9.77 µm and 6.66±0.47 branching points/mm², whereas matrices containing pure hPM showed degraded angiogenic networks, with no meshes observed and only isolated tubules with an average length of 226.58±25.64 µm. At 21 days, MP-embedded-gels showed immature mesh formation, an average tubule length of 204.07±12.75 µm and an average of 11±1.25 branching points/mm². Overall, after 21 days of culture, the angiogenic networks which formed remained stable with only minor changes in the number of branch points/mm² (FIG. 21). After 28 days culture, the average tubule length was 168.88±10.31 µm, the average number of branching points/mm² was 12.93±1.61, and the average number of meshes was 3.17±0.93 per mm².

Discussion

Protein encapsulated using PLGA microparticles is a drug delivery system for controlled release of growth factors, with a commonly employed fabrication technique being the water in oil in water method.[19,20,21] In this study, a complex human derived multiprotein mixture (placental matrix or hPM) containing over 2600 angiogenic and antifibrosis proteins was encapsulated into PLGA microparticles. Results show that using hPM-loaded-PLGA microparticles, the release of a multiprotein fusion containing pro-angiogenic and fibrotic proteins can be sustained and controlled overtime. When used with endothelial cells during in vitro culture, hPM-loaded-PLGA microparticles allow the formation of stable angiogenic networks.

These studies revealed that hPM had an influence on PLGA loading and microparticle morphology which results from the complex, multiprotein composition. In comparison to single protein (BSA) encapsulation, hPM-loaded microparticles showed an average size significantly bigger than BSA loaded ones. This is likely the result of the complex interactions between proteins in hPM and the PLGA polymer, which have a wide array of different molecular charges, pH's, and sizes in comparison to the BSA-loaded-microparticles. SDS-PAGE analysis revealed that despite the low concentration of proteins released from hPM-loaded-PLGA microparticles, a broad distribution could be observed in the supernatant with a composition similar to diluted hPM. These results suggested that the encapsulation of the protein mixture is homogeneous, not selective for specific proteins, and that the protein composition of hPM is not affected during microparticle preparation.

Both speed and duration of homogenization steps have been previously shown to affect microparticle size.[17,27] The present example revealed a correlation between hPM-loaded-PLGA microparticle size and the in vitro release rate. Although optimizing homogenization of the primary emulsion phase created microparticles with desired controlled release characteristics, the loading efficiency of hPM in these particles was somewhat low in comparison to other fabrication protocols assessed. Optimizing homogenization of the secondary emulsion phase produced microparticles in the desired size range and with increased encapsulation (up to 78%) of the protein solution. Interestingly, encapsulation efficiency did not correlate with the size of the microparticles, but instead was affected by the length of homogenization of the secondary emulsion, which is likely the result of the formation of fragmented incomplete particles caused by interactions between the heterogeneous protein mixture and the polymer.

Using the above-described optimized PLGA microparticles synthesis protocol (which allows for higher hPM encapsulation efficiency, optimized microparticle size, and linear release over 30 days in comparison to non-optimized protocols), hPM-loaded-microparticles were incorporated into an alginate-based angiogenesis assay to assess endothelial cells (HUVECS) response to controlled hPM release overtime. The 3D angiogenesis assay was created by embedding hPM-loaded-microparticles into alginate gel, which was chosen as the basis for the assay because its cost effective processability and overall good properties as an extracellular material[30,31] After 21 days of culture, HUVECS formed angiogenic tubules within the gel in regions close to the embedded hPM-loaded-PLGA microparticles, despite that the total amount of protein delivered from the microparticles (78 µg/cm²) was lower than the concentration delivered in previous 2D angiogenesis studies using bolus injections (263 µg/cm²). In comparison to bolus doses of hPM directly mixed in with the Alginate matrix, the use of hPM-loaded-microparticles allowed for an extended and sustained angiogenic network formation over 28 days. While cells formed angiogenic networks faster in alginate gels with directly mixed hPM, these networks degraded faster in comparison to gels using hPM-loaded-microparticles. After 28 days, hPM release from the microparticles was approximately zero-order, yet new formation of angiogenic meshes could still be observed, suggesting that the controlled release of hPM from PLGA microparticles improved the stability of angiogenic network formation.

Overall, this example describes the optimization of a PLGA microparticle synthesis protocol for applications to deliver complex, multiprotein mixtures with a low initial burst and a high encapsulation efficiency. The methods developed here were then applied to develop a novel angiogenesis assay, which allowed the formation of sustained angiogenic networks within alginate matrices. Importantly, the techniques developed have applications in the delivery of any complex serums and protein mixture, with applications in a wide range of tissue engineering and regenerative medicine systems. These techniques can be adapted to different materials (e.g. collagen, fibrin, laminin) with embedded serum-loaded PLGA microparticles to develop improved in vitro angiogenesis assays, and to gain a better understanding of the role played by the sustained serum delivery within cell seeded matrices.

Conclusion

This example describes an embodiment of a method for hPM encapsulation, and angiogenic structure formation was observed with an Alginate-based angiogenic assay. A sustained angiogenic response over an extended period of 21 days was observed within the 3D hydrogel culture system. This confirmed the effectiveness of the controlled hPM release approach to guide formation and maintenance of capillary networks.

References for Example 3

1. Laschke, M. W. et al. Angiogenesis in tissue engineering: breathing life into constructed tissue substitutes. Tissue Eng 12, 2093-2104 (2006).
2. Carmeliet, P. & Jain, R. K. Molecular mechanisms and clinical applications of angiogenesis. Nature 473, (2011).
3. Adair, T. H. Angiogenesis. (Morgan & Claypool Publishers, 2010). at <http://books.google.com/books?id=ykn66NeaPakC>
4. Chu, H. & Wang, Y. Therapeutic angiogenesis: controlled delivery of angiogenic factors. Ther Deliv 3, (2012).

5. Xie, J. et al. Induction of angiogenesis by controlled delivery of vascular endothelial growth factor using nanoparticles. Cardiovasc Ther 31, e12-18 (2013).
6. Chung, J. & Shum-Tim, D. Neovascularization in Tissue Engineering. Cells 1, 1246-1260 (2012).
7. Hughes, C. S., Postovit, L. M. & Lajoie, G. A. Matrigel: a complex protein mixture required for optimal growth of cell culture. Proteomics 10, 1886-1890 (2010).
8. Moore, M. C. Modulation of nutrient deficiences occuring in engineered ex vivo tissue scaffolds. (2013).
9. Pan, S.-C., Wu, L.-W., Chen, C.-L., Shieh, S.-J. & Chiu, H.-Y. Angiogenin expression in burn blister fluid: implications for its role in burn wound neovascularization. Wound Repair Regen 20, 731-739 (2012).
10. Shi, H., Han, C., Mao, Z., Ma, L. & Gao, C. Enhanced angiogenesis in porous collagen-chitosan scaffolds loaded with angiogenin. Tissue Eng Part A 14, 1775-1785 (2008).
11. Chan, O. C. M., So, K.-F. & Chan, B. P. Fabrication of nano-fibrous collagen microspheres for protein delivery and effects of photochemical crosslinking on release kinetics. Journal of Controlled Release 129, 135-143 (2008).
12. Jay, S. M. & Saltzman, W. M. Controlled delivery of VEGF via modulation of alginate microparticle ionic crosslinking. Journal of Controlled Release 134, 26-34 (2009).
13. Jay, S. M., Shepherd, B. R., Bertram, J. P., Pober, J. S. & Saltzman, W. M. Engineering of multifunctional gels integrating highly efficient growth factor delivery with endothelial cell transplantation. FASEB J 22, 2949-2956 (2008).
14. Chan, B. P. et al. Photochemical cross-linking for collagen-based scaffolds: a study on optical properties, mechanical properties, stability, and hematocompatibility. Tissue Eng 13, (2007).
15. Cohen, S., Yoshioka, T., Lucarelli, M., Hwang, L. & Langer, R. Controlled Delivery Systems for Proteins Based on Poly(Lactic/Glycolic Acid) Microspheres. Pharm Res 8, 713-720 (1991).
16. Lassalle, V. & Ferreira, M. L. PLA nano- and microparticles for drug delivery: an overview of the methods of preparation. Macromol Biosci 7, 767-783 (2007).
17. Lee, W. L. et al. Fabrication and drug release study of double-layered microparticles of various sizes. J Pharm Sci 101, 2787-2797 (2012).
18. Lee, W. L., Shi, W.-X., Low, Z. Y., Li, S. & Loo, S. C. J. Modeling of drug release from biodegradable triple-layered microparticles. J Biomed Mater Res A 100, 3353-3362 (2012).
19. Simón-Yarza, T. et al. PEGylated-PLGA microparticles containing VEGF for long term drug delivery. International Journal of Pharmaceutics 440, 13-18 (2013).
20. Kirby G T S, White L J, Rahman C V, Cox H C, Qutachi O, Rose FRAJ, Hutmacher D W, Shakesheff K M, Woodruff M A. PLGA-Based Microparticles for the Sustained Release of BMP-2. Polymers (2011). doi:3(1):571-586.
21. Wang, Y. et al. Degradable PLGA scaffolds with basic fibroblast growth factor: experimental studies in myocardial revascularization. Tex Heart Inst J 36, (2009).
22. Acharya, A. P., Lewis, J. S. & Keselowsky, B. G. Combinatorial co-encapsulation of hydrophobic molecules in poly(lactide-co-glycolide) microparticles. Biomaterials 34, 3422-3430 (2013).
23. Roman, B. S. et al. Co-encapsulation of an antigen and CpG oligonucleotides into PLGA microparticles by TROMS technology. European Journal of Pharmaceutics and Biopharmaceutics 70, 98-108 (2008).
24. Ravi, S. et al. Development and characterization of polymeric microspheres for controlled release protein loaded drug delivery system. 70, (2008).
25. Igartua, M. et al. Stability of BSA encapsulated into PLGA microspheres using PAGE and capillary electrophoresis. International Journal of Pharmaceutics 169, 45-54 (1998).
26. Bouyer, E., Mekhloufi, G., Rosilio, V., Grossiord, J.-L. & Agnely, F. Proteins, polysaccharides, and their complexes used as stabilizers for emulsions: alternatives to synthetic surfactants in the pharmaceutical field? Int J Pharm 436, 359-378 (2012).
27. Giteau, A., Venier-Julienne, M. C., Aubert-Pouëssel, A. & Benoit, J. P. How to achieve sustained and complete protein release from PLGA-based microparticles? International Journal of Pharmaceutics 350, 14-26 (2008).
28. Klose, D., Siepmann, F., Elkharraz, K. & Siepmann, J. PLGA-based drug delivery systems: Importance of the type of drug and device geometry. International Journal of Pharmaceutics 354, 95-103 (2008).
29. Acharya, G. et al. A study of drug release from homogeneous PLGA microstructures. Journal of Controlled Release 146, 201-206 (2010).
30. Rowley, J. A., Madlambayan, G. & Mooney, D. J. Alginate hydrogels as synthetic extracellular matrix materials. Biomaterials 20, 45-53 (1999).
31. Gandhi, J. K., Opara, E. C. & Brey, E. M. Alginate-based strategies for therapeutic vascularization. Ther Deliv 4, 327-341 (2013).
32. Zisch, A. H., Lutolf, M. P. & Hubbell, J. A. Biopolymeric delivery matrices for angiogenic growth factors. Cardiovasc Pathol 12, (2003).
33. Goodwin, A. M. In vitro assays of angiogenesis for assessment of angiogenic and anti-angiogenic agents. Microvascular Research 74, 172-183 (2007).

The invention claimed is:
1. A composition comprising:
    a human placental extract obtained from a human placental sample, wherein blood and solids have been substantially removed from the extract, and the extract comprises placental proteins including cytokines and growth factors, wherein the placental proteins were present in the placental sample, and the extract comprises less than 2% normalized protein abundance of collagen IV, less than 2% normalized protein abundance of laminin, or less than 2% normalized protein abundance of each of collagen IV and laminin; and
    biodegradable microparticles,
wherein the human placental extract is coupled to the microparticles such that the human placental extract is released from the microparticles over a period of time after exposure to cells in vivo or in vitro.
2. The composition of claim 1, wherein the placental extract is made by:
    removing blood from a sample obtained from the human placenta sample to produce a crude placental extract;
    mixing the crude placental extract with a protein solubilization agent to solubilize proteins in the crude extract;
    separating solid materials from the solubilized protein-placental extract mixture;
    performing dialysis on the solubilized protein-placental extract mixture to remove the protein solubilization agent from the mixture; and
    after dialysis, removing remaining solids from the extract to produce the human placental extract.

3. The composition of claim 2, wherein the protein solubilization agent is capable of reversibly denaturing proteins in the crude placental extract.

4. The composition of claim 1, wherein the placental extract includes at least 20 different cytokines.

5. The composition of claim 2, wherein the protein solubilization agent is urea.

6. The composition of claim 1, wherein the placental extract is capable of increasing angiogenesis.

7. The composition of claim 1, wherein the biodegradable microparticles comprise Poly(DL-lactide-co-glycolide) (PLGA) microparticles.

8. The composition of claim 7, wherein the PLGA microparticles are loaded with the human placental extract (hPE) and wherein the hPE loaded PLGA microparticles are made with an oil in water process that involves a dual homogenization.

9. The composition of claim 1, wherein the biodegradable microparticles comprise gelatin microparticles.

10. The composition of claim 1, wherein the biodegradable microparticles comprise different sizes of microparticles.

11. The composition of claim 1, wherein the human placental extract comprises less than 2% normalized protein abundance of collagen IV and less than 2% normalized protein abundance of laminin.

12. The composition of claim 1, wherein the human placental extract comprises less than 2% normalized protein abundance of collagen IV.

13. A method of inducing angiogenesis comprising:
contacting cells with a sustained release angiogenesis-modulating composition, the sustained release angiogenesis-modulating composition comprising:
biodegradable microparticles, and
a human placental extract coupled to the microparticles such that the human placental extract is released from the microparticles over a period of time after exposure of the microparticles to cells in vivo or in vitro, wherein the placental extract comprises an extract obtained from a human placental sample, wherein blood and solids have been substantially removed from the extract, and the extract comprises placental proteins including cytokines and growth factors, wherein the placental proteins were present in the placental sample, and wherein the extract comprises less than 2% normalized protein abundance of collagen IV, less than 2% normalized protein abundance of laminin, or less than 2% normalized protein abundance of each of collagen IV and laminin.

14. The method of claim 13, wherein the cells are endothelial cells.

15. The method of claim 13, wherein the placental extract is made by:
removing blood from a sample obtained from the human placenta sample to produce a crude placental extract;
mixing the crude placental extract with a protein solubilization agent to solubilize proteins in the crude extract;
separating solid materials from the solubilized protein-placental extract mixture;
performing dialysis on the solubilized protein-placental extract mixture to remove the protein solubilization agent from the mixture; and
after dialysis, removing remaining solids from the extract to produce the human placental extract.

16. The method of claim 15, wherein the protein solubilization agent is urea.

17. The method of claim 13, further comprising:
coupling the sustained release angiogenesis-modulating composition to a biomaterial.

18. The method of claim 17, further comprising inducing vascularization of the biomaterial in vivo by implanting the biomaterial in a subject.

19. The method of claim 18, wherein the subject is a human.

20. The method of claim 17, wherein the biomaterial is an engineered bioscaffold comprising human derived substrate material.

21. The method of claim 17, wherein the bioscaffold comprises a decellularized human umbilical vein scaffold seeded with human endothelial cells.

22. The method of claim 21, wherein the human endothelial cells are human umbilical vein endothelial cells (HUVECs).

23. A method of reducing inflammation in a subject comprising:
administering to the subject a composition comprising biodegradable microparticles and a human placental extract obtained from a human placental sample, wherein blood and solids have been substantially removed from the extract, and the extract comprises placental proteins including cytokines and growth factors, wherein the placental proteins were present in the placental sample, and wherein the extract comprises less than 2% normalized protein abundance of collagen IV, less than 2% normalized protein abundance of laminin, or less than 2% normalized protein abundance of each of collagen IV and laminin,
wherein the human placental extract is coupled to the microparticles such that the human placental extract is released from the microparticles over a period of time after exposure to cells.

24. A composition comprising:
biodegradable microparticles; and
a human placental extract coupled to the microparticles such that the human placental extract is released from the microparticle over a period of time after exposure of the microparticles to cells in vivo or in vitro, wherein the placental extract comprises an extract obtained from a human placental sample and made by:
removing blood from a sample obtained from the human placental sample to produce a crude extract;
mixing the crude placental extract with a protein solubilization agent to solubilize proteins in the crude extract;
separating solid materials from the solubilized protein-placental extract mixture;
performing dialysis on the solubilized protein-placental extract mixture to remove the protein solubilization agent from the mixture; and
after dialysis, removing polymerized solids from the extract to produce the human placental extract,
wherein the placental extract includes at least 20 different cytokines; and
wherein the placental extract increases angiogenesis.

25. The composition of claim 24, wherein removal of polymerized solids from the extract after dialysis produces a human placental extract having less than 2% normalized protein abundance of collagen IV, less than 2% normalized protein abundance of laminin, or less than 2% normalized protein abundance of each of collagen IV and laminin.

26. The composition of claim 24, wherein the protein solubilization agent is urea.

27. The composition of claim 24, wherein the biodegradable microparticles comprise Poly(DL-lactide-co-glycolide) (PLGA) microparticles or gelatin microparticles.

28. The composition of claim 27, wherein the biodegradable microparticles comprise PLGA microparticles, and wherein the PLGA microparticles are made and coupled to the human placental extract with an oil in water process that comprises combining the human placental extract with water and oil in a first homogenization step to produce a primary emulsion, combining the primary emulsion with a water and alcohol solution in a second homogenization step to produce a secondary emulsion to produce PLGA microparticles loaded with the human placental extract.

29. The composition of claim 28, wherein the first homogenization step comprises homogenizing the oil and water for greater than 1 minute.

* * * * *